(12) United States Patent
Lee et al.

(10) Patent No.: US 12,676,236 B2
(45) Date of Patent: Jul. 7, 2026

(54) BIOMARKER FOR EARLY DETECTION OF ALZHEIMER DISEASE

(71) Applicant: National Cheng Kung University, Tainan City (TW)

(72) Inventors: Gwo-Giun Lee, Tainan City (TW); Te-Han Kung, Tainan City (TW); Tzu-Cheng Chao, Tainan City (TW); Yu-Min Kuo, Tainan City (TW)

(73) Assignee: National Cheng Kung University, Tainan City (TW)

( * ) Notice: Subject to any disclaimer, the term of this patent is extended or adjusted under 35 U.S.C. 154(b) by 218 days.

(21) Appl. No.: 18/351,583

(22) Filed: Jul. 13, 2023

(65) Prior Publication Data

US 2024/0079143 A1     Mar. 7, 2024

Related U.S. Application Data

(63) Continuation-in-part of application No. 16/724,293, filed on Dec. 22, 2019, now Pat. No. 11,712,192.

(30) Foreign Application Priority Data

Dec. 19, 2019     (EP) .................................... 19218311

(51) Int. Cl.
*G16H 50/20* (2018.01)
*G06N 3/08* (2023.01)
(52) U.S. Cl.
CPC .............. *G16H 50/20* (2018.01); *G06N 3/08* (2013.01)

(58) Field of Classification Search
None
See application file for complete search history.

(56) References Cited

U.S. PATENT DOCUMENTS 8,452,373 B2     5/2013   Wyrwicz et al.
9,125,580 B2     9/2015   Lee et al.

OTHER PUBLICATIONS

Lee et al., "Predicting Alzheimer's disease progression using multi-modal deep learning approach," (Feb. 13, 2019), Scientific Reports vol. 9, Article No. 1952. (Year: 2019).*
Li et al., "A deep learning model for early prediction of Alzheimer's disease dementia based on hippocampal magnetic resonance imaging data," (Jun. 11, 2019), Alzheimers Dement. Jun. 11, 2019;15(8):1059-1070. (Year: 2019).*

(Continued)

*Primary Examiner* — Keith M Raymond
*Assistant Examiner* — Ashish S. Jasani
(74) *Attorney, Agent, or Firm* — RABIN & BERDO, P.C.

(57) ABSTRACT

The present disclosure relates to a method for providing biomarker for early detection of Alzheimer's Disease (AD), and particularly to a method that is able to enhance the accuracy of predicting AD from Mild Cognitive Impairment (MCI) patients using the Hippocampus magnetic resonance imaging (MRI) scans and Mini-Mental State Examination (MMSE) data. The providing MRI images containing the anatomical structure of Hippocampus biomarker and MMSE data as a training data set; training a processor using the training data set, and the training comprising acts of receiving MRI images and MMSE data as a testing data set from a target; and classifying the test data by the trained processor to include aggregating predictions.

6 Claims, 38 Drawing Sheets

(56)　　　　　References Cited

OTHER PUBLICATIONS

Da Silva et al. ("Distinguishing Healthy Ageing from Dementia: a Biomechanical Simulation of Brain Atrophy using Deep Networks," Aug. 18, 2021, https://doi.org/10.48550/arXiv.2108.08214. (Year: 2021).*

Tabarestani et al., "Longitudinal Prediction Modeling of Alzheimer Disease using Recurrent Neural Networks," (May 19, 2019), 2019 IEEE EMBS International Conference on Biomedical & Health Informatics (BHI). (Year: 2019).*

Wang et al., "Detection of Alzheimer's Disease by Three-Dimensional Displacement Field Estimation in Structural Magnetic Resonance Imaging," (Dec. 1, 2015), Journal of Alzheimer's Disease 50 (2016) 233-248 (Year: 2015).*

Dong et al., "DeepAtrophy: Teaching a neural network to detect progressive changes in longitudinal MRI of the hippocampal region in Alzheimer's disease," (Nov. 2021), NeuroImage 243 (2021) 118514. (Year: 2021).*

Dadar et al., "A comparison of publicly available linear MRI stereotaxic registration techniques," (Jul. 1, 2018) Neuroimage, vol. 174, pp. 191-200. (Year: 2018).

Dalton et al., "Segmenting subregions of the human hippocampus on structural magnetic resonance image scans: An illustrated tutorial," (Apr. 6, 2017) Brain Neurosci Adv. Jan.-Dec. 2017; 1:2398212817701448. (Year: 2017).

DeKraker et al., "Unfolding the hippocampus: an intrinsic coordinate system for subfield segmentations and quantitative mapping," (Jun. 7, 2017) bioRxiv 146878. (Year: 2017).

Fischl et al., "Whole Brain Segmentation: Automated Labeling of Neuroanatomical Structures in the Human Brain" (Jan. 31, 2002) Neuron 33, 341-355. (Year: 2002).

Freesurfer Citations (Year: NA), Internet URL: https://surfer.nmr.mgh.harvard.edu/fswiki/FreeSurferMethodsCitation.

Freesurfer ColorLUT (Year: 2015), Internet URL: https://surfer.nmr.mgh.harvard.edu/fswiki/FsTutorial/AnatomicalROI/FreeSurferColorLUT.

Freesurfer Hippocampal Subfields (Year: NA), Internet URL: https://surfer.nmr.mgh.harvard.edu/fswiki/HippocampalSubfields.

Freesurfer Intensity Normalization (Year: 2008), Internet URL: https://surfer.nmr.mgh.harvard.edu/fswiki/IntensityNormalization.

Freesurfer MRI_mask (Year: 2018), Internet URL: https://surfer.nmr.mgh.harvard.edu/fswiki/mri_mask.

Freesurfer Normalization (Year: 2009), Internet URL: https://surfer.nmr.mgh.harvard.edu/fswiki/normalization.

Freesurfer Normalization2 (Year: 2009), Internet URL: https://surfer.nmr.mgh.harvard.edu/fswiki/normalization2.

Freesurfer Release Notes (Year: NA), Internet URL: https://surfer.nmr.mgh.harvard.edu/fswiki/ReleaseNotes.

Freesurfer Support (Year: NA), Internet URL: https://surfer.nmr.mgh.harvard.edu/fswiki/FreeSurferSupport.

Freesurfer Talairach (Year: 2009), Internet URL: https://surfer.nmr.mgh.harvard.edu/fswiki/talairach.

Freesurfer Wiki (Year: NA), Internet URL: https://surfer.nmr.mgh.harvard.edu/fswiki/.

Gwo Giun (Chris) Lee, "Skin Cancer Detection via Deep Analytics of Harmonically Generated Microscopy (HGM) Images", 2018 Spring Dermatology & Skin Care Expo Conference, Montreal, Canada, May 14-15, 2018.

Gwo Giun Lee et al., "Gabor Feature Extraction for Electrocardiogram Signals," 2012 IEEE Biomedical Circuits and Systems Conference (BioCAS), Hsinchu, Taiwan, pp. 304-307, Nov. 2012.

Iglesias et al., "A computational atlas of the hippocampal formation using ex vivo, ultra-high resolution MRI: Application to adaptive segmentation of in vivo MRI," (Jul. 15, 2015), Neuroimage, vol. 115, pp. 117-137. (Year: 2015).

Kim et al., "Disentangling hippocampal shape anomalies in epilepsy," (Sep. 11, 2013) Front. Neurol., vol. 4, article 131, pp. 1-6. (Year: 2013).

Platero et al., "Discrimination Alzheimer's disease progression using a new hippocampal marker from T1-weighted MRI: The local surface roughness," (Oct. 19, 2018), Wiley Periodicals, Hum Brain Mapp. 2019; 40:1666-1676. (Year: 2018).

Platero et al., "Longitudinal Neuroimaging Hippocampal Markers for Diagnosing Alzheimer's Disease," (May 21, 2018) Neuroinform 17, 43-61. (Year: 2018).

Raut et al., "A machine learning based approach for detection of alzheimer's disease using analysis of hippocampus region from MRI scan," (Jul. 18, 2017) 2017 International Conference on Computing Methodologies and Communication (ICCMC), 2017, pp. 236-242. (Year: 2017).

Re:[Freesurfer] Cortical surface tessellation and smoothing (Year: 2007), Internet URL: https://www.mail-archive.com/freesurfer@nmr.mgh.harvard.edu/msg05413.html.

Shi et al., "Hippocampal subfields segmentation in brain MR images using generative adversarial networks," (Jan. 21, 2019) BioMedical Engineering Online vol. 18, Article No. 5. (Year: 2019).

Wisse et al., "A critical appraisal of the hippocampal subfield segmentation package in FreeSurfer," (Sep. 25, 2014) Front Aging Neurosci. (Year: 2014).

* cited by examiner

Hippocampal
subfields-labeled MRI

Whole hippocampus
boundary

Hippocampal subfields
boundary

Hippocampus surface

Hippocampal subfields
labeling surface

Curvature surface

Input layer          Hidden layer          Output layer

701

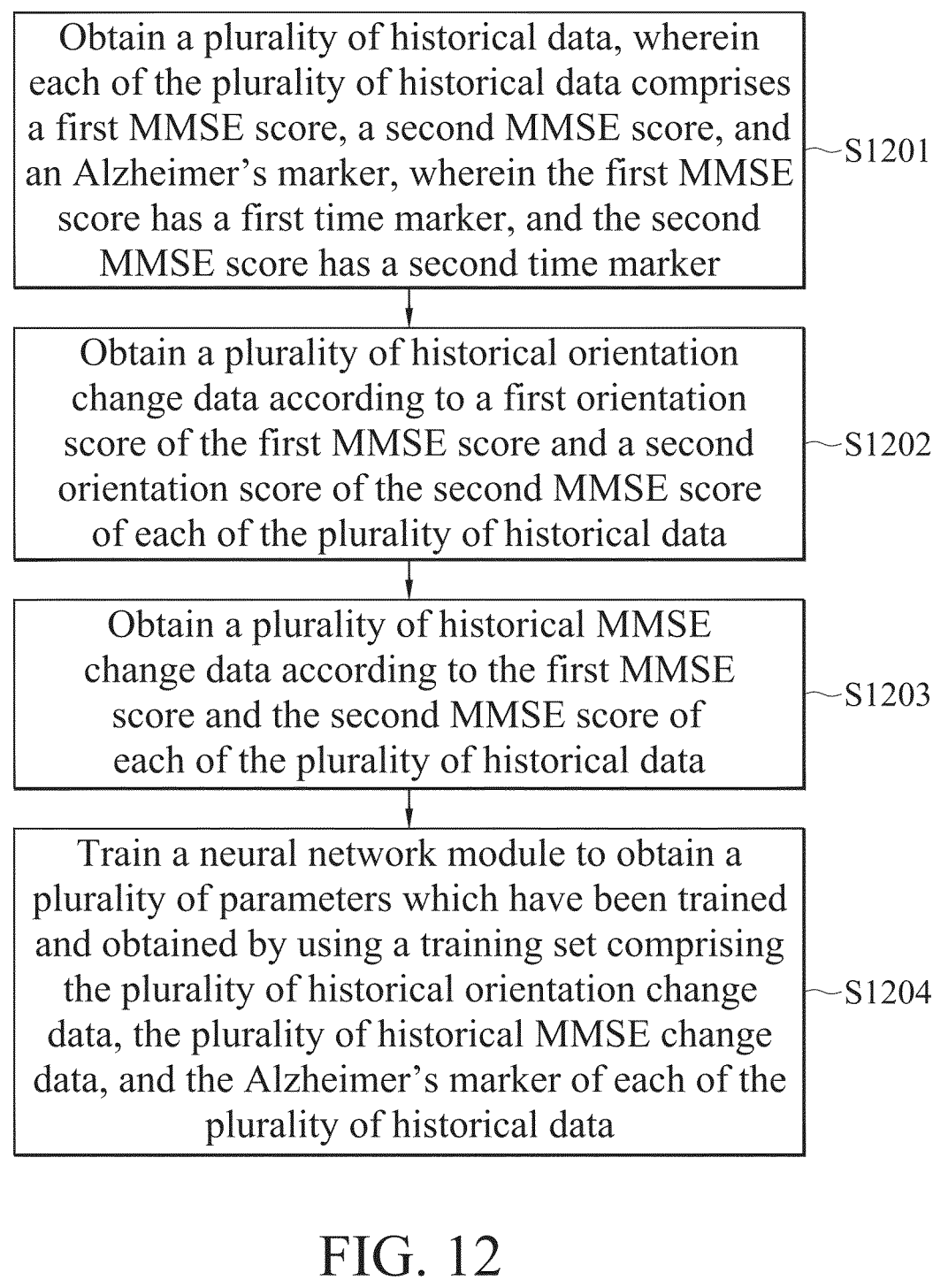

Obtain a plurality of historical data, wherein each of the plurality of historical data comprises a first MMSE score, a second MMSE score, and an Alzheimer's marker, wherein the first MMSE score has a first time marker, and the second MMSE score has a second time marker ~S1201

Obtain a plurality of historical orientation change data according to a first orientation score of the first MMSE score and a second orientation score of the second MMSE score of each of the plurality of historical data ~S1202

Obtain a plurality of historical MMSE change data according to the first MMSE score and the second MMSE score of each of the plurality of historical data ~S1203

Train a neural network module to obtain a plurality of parameters which have been trained and obtained by using a training set comprising the plurality of historical orientation change data, the plurality of historical MMSE change data, and the Alzheimer's marker of each of the plurality of historical data ~S1204

FIG. 12

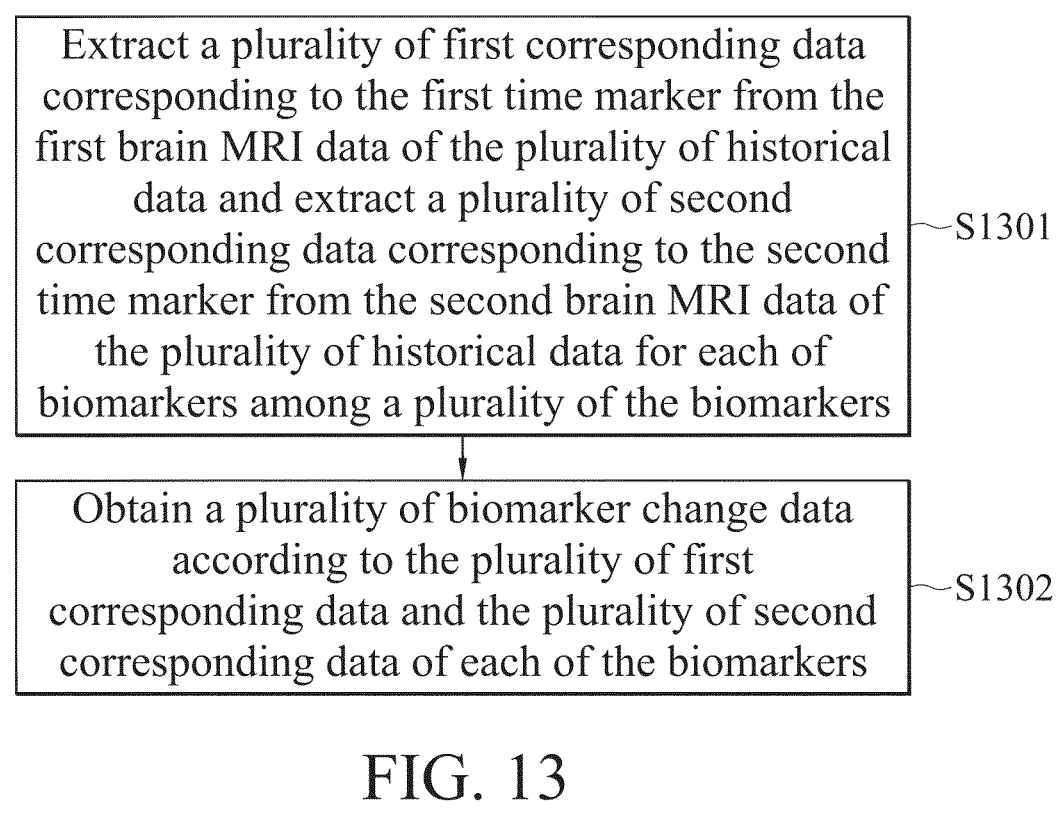

Extract a plurality of first corresponding data corresponding to the first time marker from the first brain MRI data of the plurality of historical data and extract a plurality of second corresponding data corresponding to the second time marker from the second brain MRI data of the plurality of historical data for each of biomarkers among a plurality of the biomarkers ~S1301

Obtain a plurality of biomarker change data according to the plurality of first corresponding data and the plurality of second corresponding data of each of the biomarkers ~S1302

FIG. 13

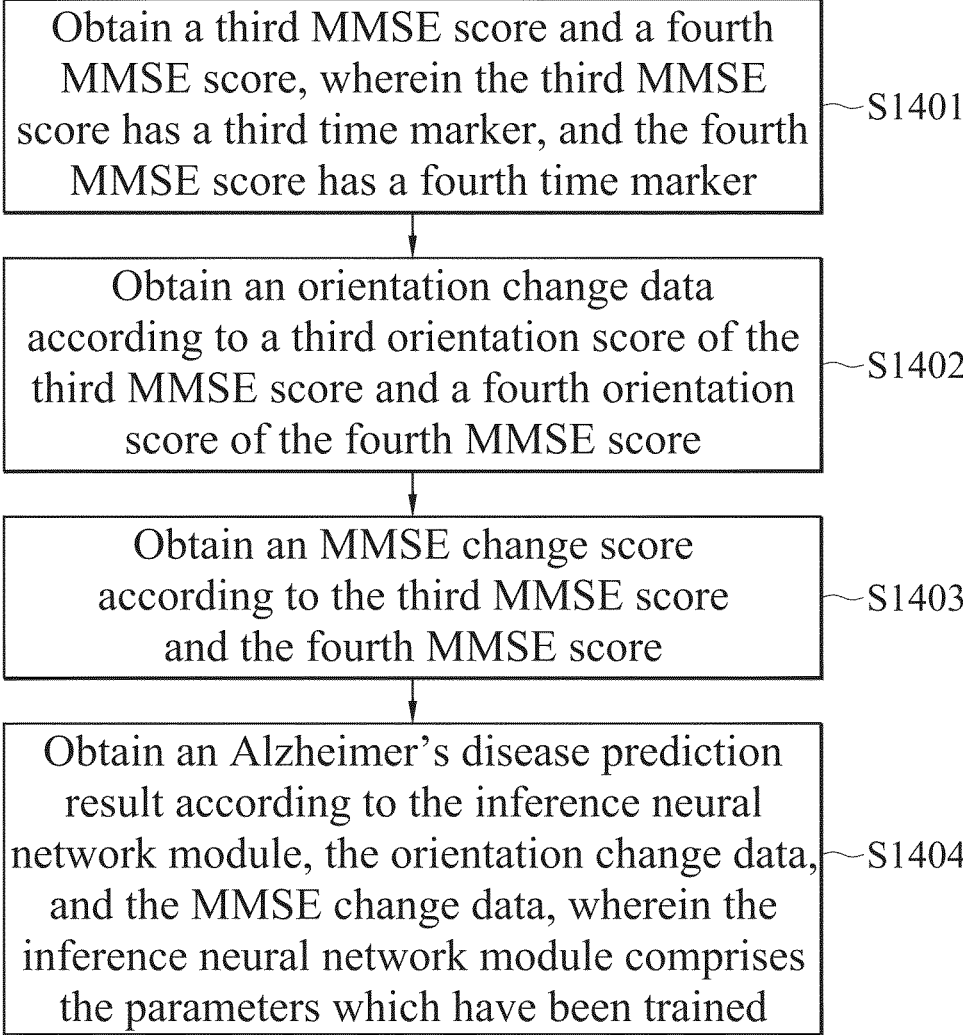

Obtain a third MMSE score and a fourth MMSE score, wherein the third MMSE score has a third time marker, and the fourth MMSE score has a fourth time marker ~S1401

Obtain an orientation change data according to a third orientation score of the third MMSE score and a fourth orientation score of the fourth MMSE score ~S1402

Obtain an MMSE change score according to the third MMSE score and the fourth MMSE score ~S1403

Obtain an Alzheimer's disease prediction result according to the inference neural network module, the orientation change data, and the MMSE change data, wherein the inference neural network module comprises the parameters which have been trained ~S1404

FIG. 14

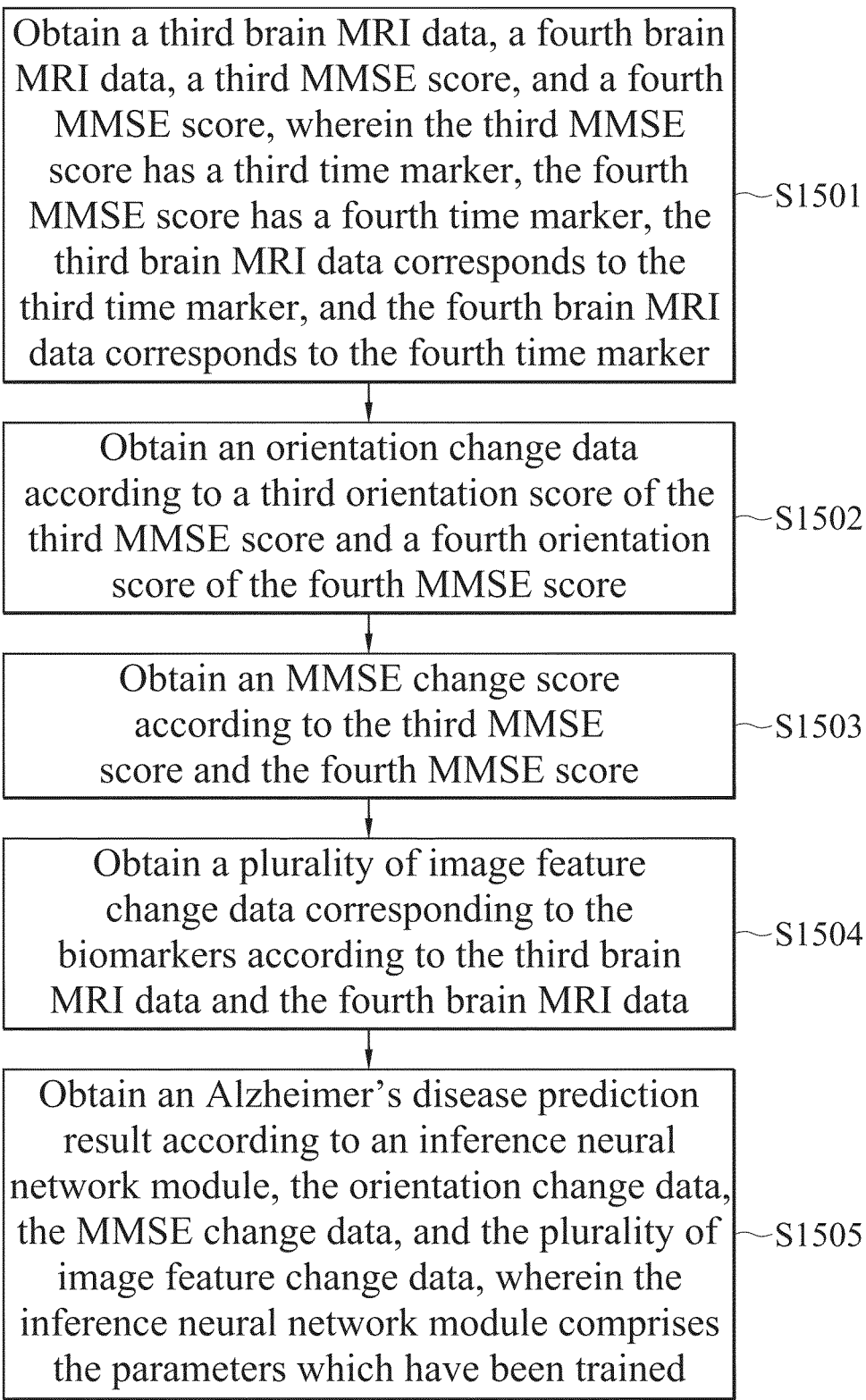

Obtain a third brain MRI data, a fourth brain MRI data, a third MMSE score, and a fourth MMSE score, wherein the third MMSE score has a third time marker, the fourth MMSE score has a fourth time marker, the third brain MRI data corresponds to the third time marker, and the fourth brain MRI data corresponds to the fourth time marker ~S1501

Obtain an orientation change data according to a third orientation score of the third MMSE score and a fourth orientation score of the fourth MMSE score ~S1502

Obtain an MMSE change score according to the third MMSE score and the fourth MMSE score ~S1503

Obtain a plurality of image feature change data corresponding to the biomarkers according to the third brain MRI data and the fourth brain MRI data ~S1504

Obtain an Alzheimer's disease prediction result according to an inference neural network module, the orientation change data, the MMSE change data, and the plurality of image feature change data, wherein the inference neural network module comprises the parameters which have been trained ~S1505

FIG. 15

BIOMARKER FOR EARLY DETECTION OF ALZHEIMER DISEASE

CROSS-REFERENCES TO RELATED APPLICATIONS

This application is a continuation-in-part (cip) of application Ser. No. 16/724,293, filed on 2019 Dec. 22, with claiming foreign priority of EP19218311.9, filed on 2019 Dec. 19. The prior applications are herewith incorporated by reference in its entirety.

COPYRIGHT NOTICE

FIELD OF THE INVENTION

The present disclosure relates to a method for predicting Alzheimer's Disease (AD), and particularly to a method that is able to enhance the accuracy of predicting AD from Mild Cognitive Impairment (MCI) patients by providing biomarker.

BACKGROUND OF THE INVENTION

Cognitive decline is one of the most concerning behavioral symptoms such as AD. Seamless changes in the AD continuum take years if not decades to progress from normal cognition (NC) to MCI, with gradual evolution of clinically probable AD to confirmed AD. Early detection and accurate diagnosis of AD require careful medical assessment, including patient history as well as physical and neurological examinations.

The MMSE is a brief cognitive assessment tool commonly used to screen for dementia. Neuroimaging modalities such as MRI that provides biologic evidences which cognitive decline is neurodegenerative as they contain detailed information regarding the subcortical structures, good contrast of the gray matter, and the integrity of the brain tissue.

Machine learning techniques have been widely used over the past few years for the analysis of biomedical images, and more particularly to frameworks known as deep learning, which is based on artificial neural networks, which has received increased attention because of its remarkable success in predicting various clinical outcomes of interest. The convolutional neural network (CNN) models are considered to be efficient deep learning techniques for object recognition and classification.

However, MRI scans are characterized as complex, unstructured data structures and thus require sophisticated means by which to perform an efficiently quantitative analysis. The most common neurological examination for predicting AD is to monitor the overall volume of Hippocampus from MRI scans.

Accordingly, there's a need to combine the structural information derived from neuroimaging data (i.e., MRI scans) and functional information (i.e., MMSE) derived from screening tools and cognitive assessment methods can result in a better combined metric of predicting AD.

SUMMARY

In view of this, some embodiments of the present disclosure provide a neural network training system, an Alzheimer's disease prediction system using the parameters which have been trained obtained from the neural network training system, a neural network training method, and an Alzheimer's disease prediction method using the parameters which have been trained obtained from the neural network training method so as to address issues currently encountered.

In some embodiments of the present disclosure, a neural network training system is provided. The neural network training system includes a neural network module and a processor. The neural network module has a plurality of parameters. The processor is configured to: obtain a plurality of historical data, wherein each of the plurality of historical data comprises a first Mini-Mental State Examination (MMSE) score, a second MMSE score, and an Alzheimer's marker, wherein the first MMSE has a first time marker, and the second MMSE has a second time marker; obtain a plurality of historical orientation change data according to a first orientation score of the first MMSE score and a second orientation score of the second MMSE score of each of the plurality of historical data; obtain a plurality of MMSE change data according to the first MMSE score and the second MMSE score of each of the plurality of historical data; and train the neural network module to obtain parameters which have been trained by using a training set comprising the historical orientation change data, the historical MMSE change data, and the Alzheimer's marker of each of the plurality of historical data.

In some embodiments of the present disclosure, an Alzheimer's disease prediction system using the parameters which have been trained obtained from the aforementioned neural network training system is provided. The Alzheimer's disease prediction system comprises an inference processor and an inference neural network module. The inference processor is configured to obtain a third MMSE score and a fourth MMSE score, wherein the third MMSE score has a third time marker, and the fourth MMSE score has a fourth time marker; the inference neural network module comprises the parameters which have been trained. The inference processor is configured to obtain an orientation change data according to a third orientation score of the third MMSE score and a fourth orientation score of the fourth MMSE score; obtain an MMSE change score according to the third MMSE score and the fourth MMSE score; and obtain an Alzheimer's disease prediction result according to the inference neural network module, the orientation change data, and the MMSE change data.

In some embodiments of the present disclosure, a neural network training method is provided. The neural network training method is performed by a processor and includes obtaining a plurality of historical data, wherein each of the plurality of historical data comprises a first MMSE score, a second MMSE score, and an Alzheimer's marker, wherein the first MMSE has a first time marker, and the second MMSE has a second time marker; obtaining a plurality of historical orientation change data according to a first orientation score of the first MMSE score and a second orientation score of the second MMSE score of each of the plurality of historical data; obtaining a plurality of MMSE change data according to the first MMSE score and the second MMSE score of each of the plurality of historical data; and training a neural network module to obtain parameters which have been trained by using a training set comprising the historical orientation change data, the historical MMSE change data, and the Alzheimer's marker of each of the plurality of historical data.

In some embodiments of the present disclosure, an Alzheimer's disease prediction method using the parameters which have been trained obtained from the aforementioned neural network training method is provided. The Alzheimer's disease prediction method is performed by an inference processor and includes obtaining a third MMSE score and a fourth MMSE score, wherein the third MMSE score has a third time marker, and the fourth MMSE score has a fourth time marker; obtaining an orientation change data according to a third orientation score of the third MMSE score and a fourth orientation score of the fourth MMSE score; obtaining an MMSE change score according to the third MMSE score and the fourth MMSE score; and obtaining an Alzheimer's disease prediction result according to an inference neural network module, the orientation change data, and the MMSE change data, wherein the inference neural network module comprises the parameters which have been trained.

Based on the above, according to the neural network training system, the Alzheimer's disease prediction system using the parameters which have been trained obtained from the neural network training system, the neural network training method, and the Alzheimer's disease prediction method using the parameters which have been trained obtained from the neural network training method of one or some embodiments of the present disclosure, the orientation score of the MMSE score is introduced to reduce (or even to omit) the use of the brain MRI data for the Alzheimer's disease prediction.

BRIEF DESCRIPTION OF THE DRAWINGS

Embodiments of the invention are described in more details hereinafter with reference to the drawings, in which:

FIG. 12 is a flowchart of a neural network training method in accordance with an embodiment of the present invention.

FIG. 13 is a flowchart of a neural network training method in accordance with an embodiment of the present invention.

FIG. 14 is a flowchart of an Alzheimer's disease prediction method in accordance with an embodiment of the present invention.

FIG. 15 is a flowchart of an Alzheimer's disease prediction method in accordance with an embodiment of the present invention.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of particular elements, the term "includes/comprises" means includes but not limited to, the term "including/comprising" means including but not limited to, and the term "based on" means based at least in part on.

Figure 1:
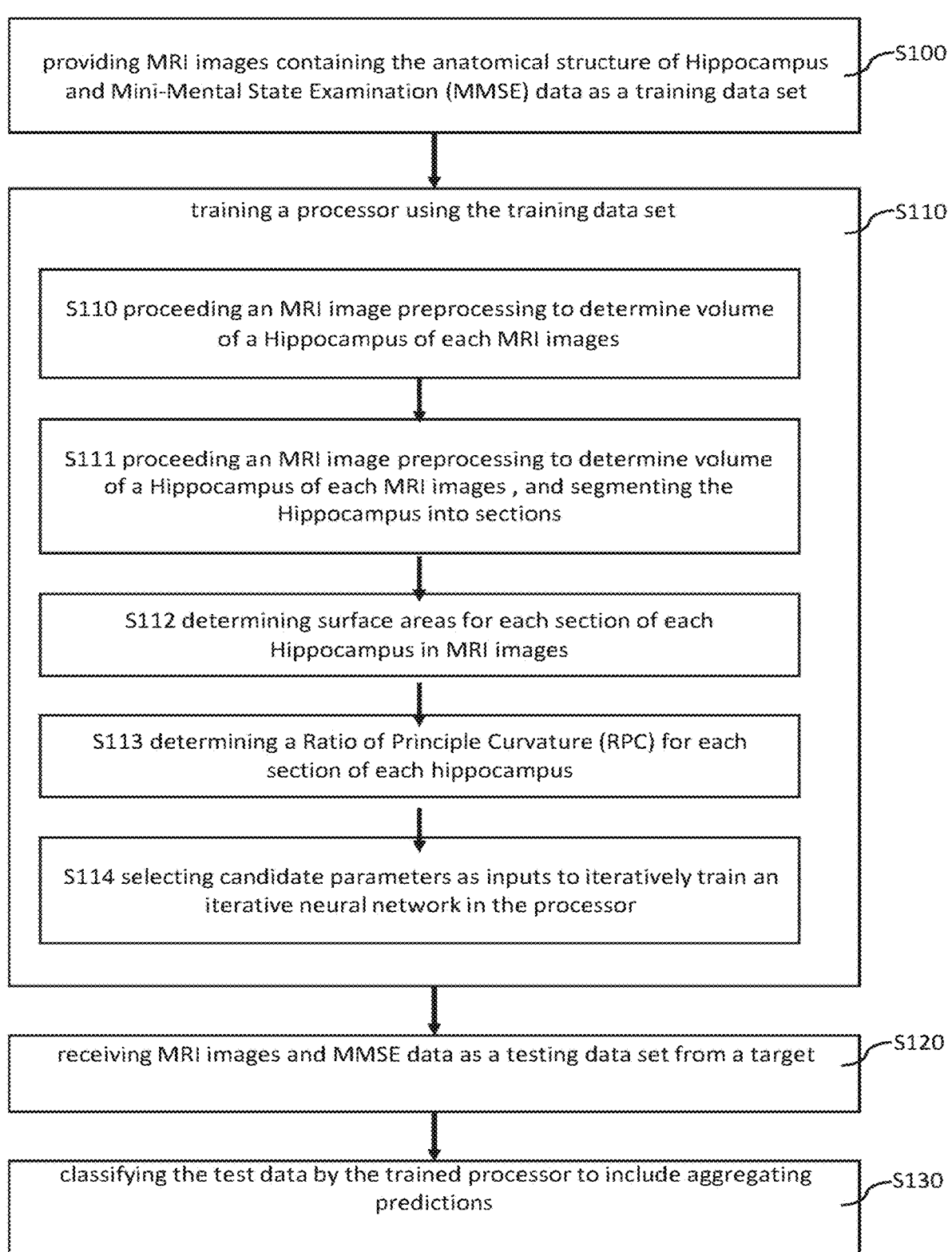
FIG. 1 is a flowchart illustrating a method for predicting Alzheimer's Disease (AD) in accordance with an embodiment of the present invention.
Figure 2:
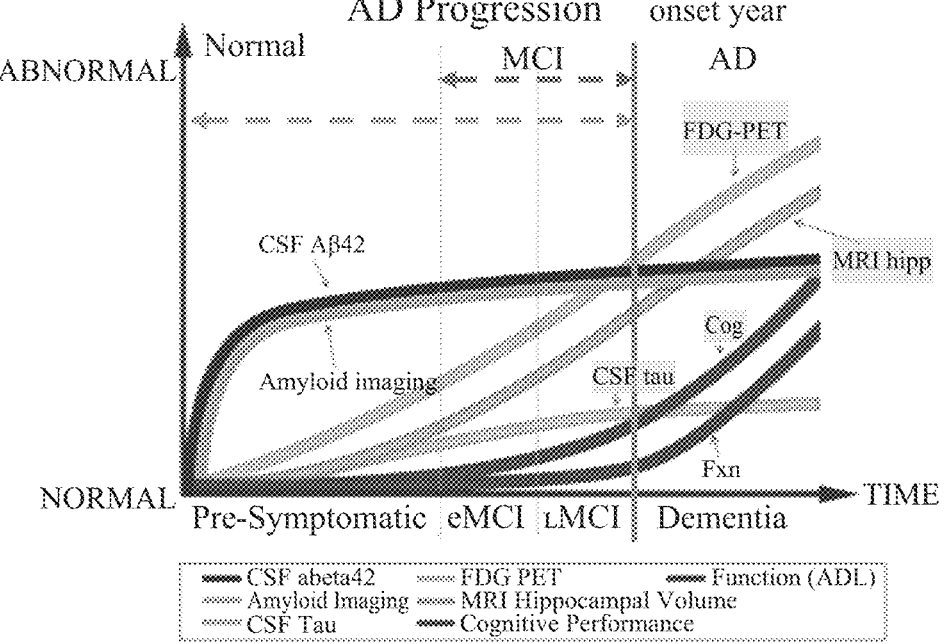
FIG. 2 is an exemplary diagram illustrating the observing factors in the AD progression.

With reference to FIGS. 1 and 2, FIG. 1 is a flowchart illustrating a method for predicting AD in accordance with an embodiment of the present invention; and FIG. 2 is an exemplary diagram illustrating the observing factors in the AD progression. As shown in FIG. 2, the Hippocampus volume is considered the most important and crucial factor to distinguish individuals with AD, especially from the ones who have MCI is crucial within the realm of early detection of AD.

The objective of the present invention is to create a predictive computing model of AD by considering detailed structural and anatomic information contained within the MRI images as well as cognitive function assessed using the MMSE.

Accordingly, as shown in FIG. 1, in an embodiment, Aa method for predicting Alzheimer's Disease comprising acts of S100 providing MRI images containing the anatomical structure of Hippocampus and MMSE data as a training data set, S110 training a processor using the training data set, S120 receiving MRI images and MMSE data as a testing data set from a target, and S130 classifying the test data by the trained processor to include aggregating predictions.

The acts of S110 training of the processor using the training data set is comprising acts of S111 proceeding an MRI image preprocessing to determine volume of a Hippocampus of each MRI images, and segmenting the Hippocampus into sections (or called sub-region), S112 determining surface areas for each section of each Hippocampus in MRI images, S113 determining a Ratio of RPC for each section of each Hippocampus, and S114 selecting candidate parameters as inputs to iteratively train an iterative neural network in the processor. The candidate parameters are selected from the volume of Hippocampus, the surface areas and PRC of sections of Hippocampus, and scores of the MMSE data.

Figure 3A:
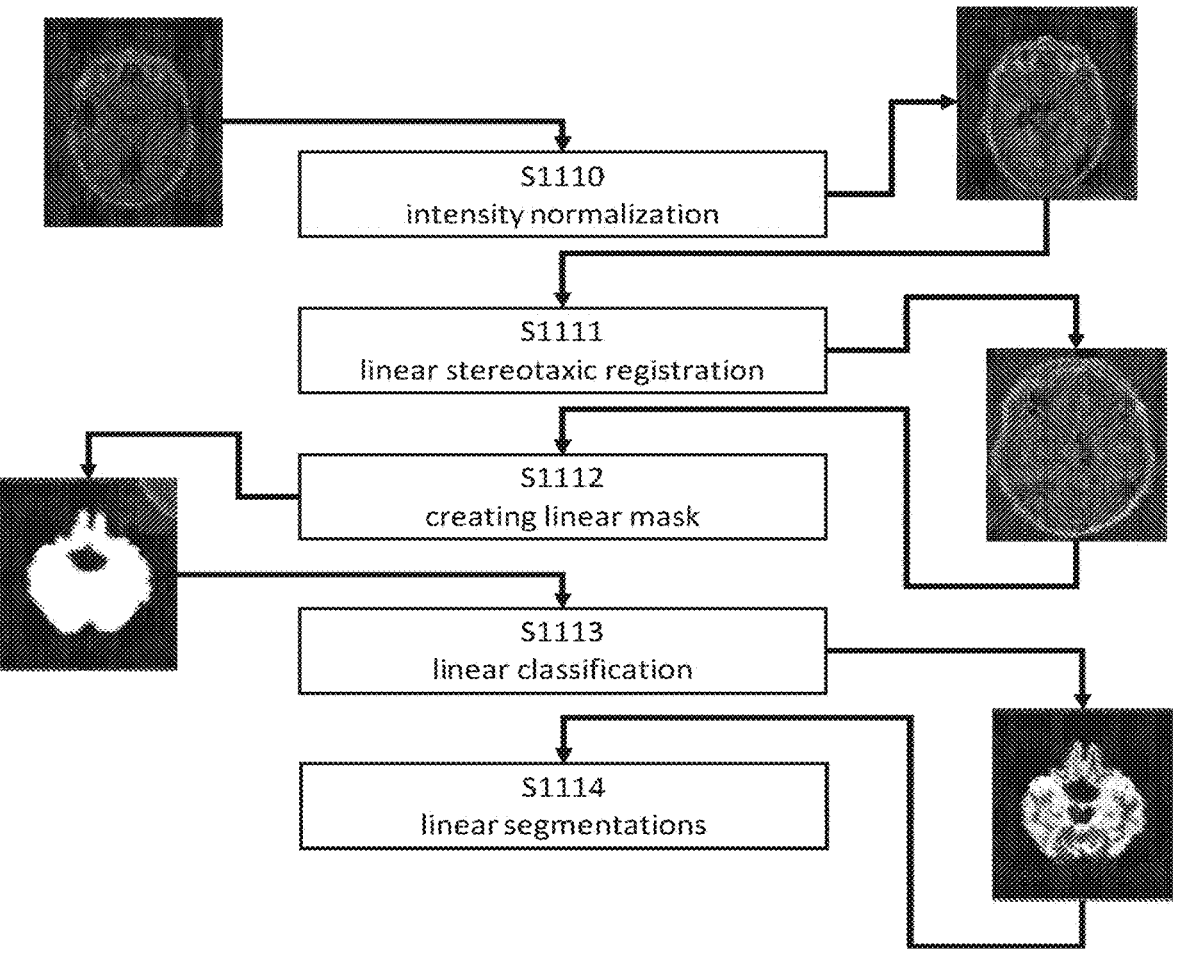
FIG. 3A is a flowchart illustrating the acts of S111 with corresponding MRI images for each of steps in accordance with an embodiment of the present invention.
Figure 3B:
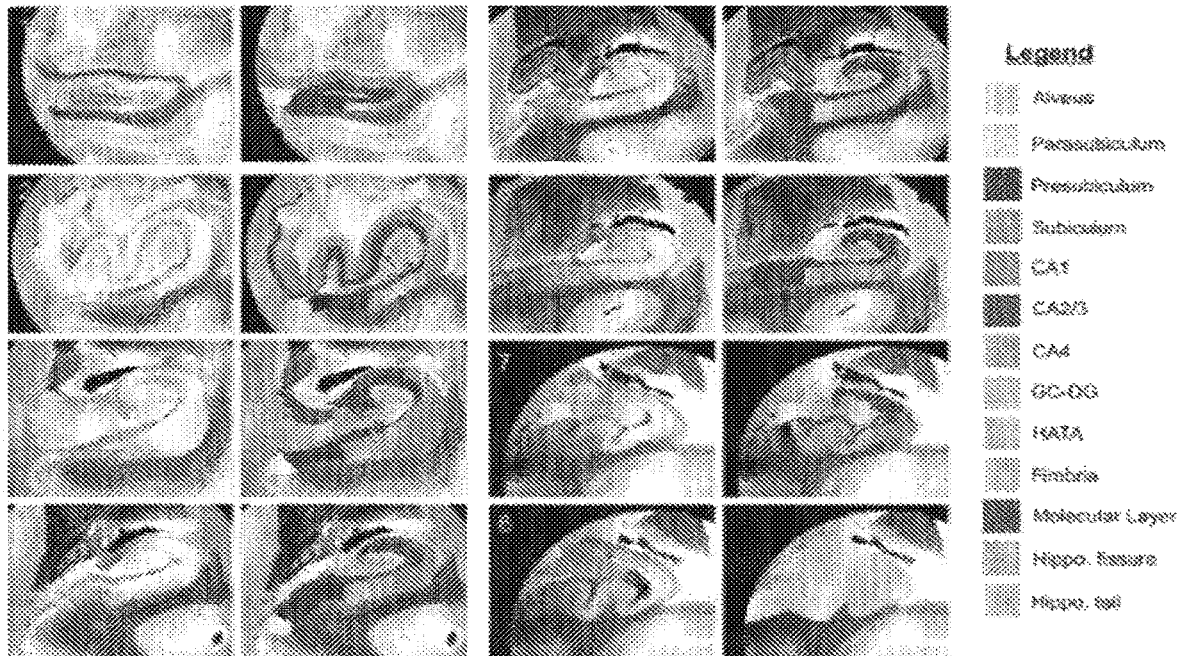
FIG. 3B is an exemplary diagram illustrating the sections of the Hippocampus.

With further reference to FIGS. 3A and 3B, FIG. 3A is a flowchart illustrating the acts of S111 with corresponding MRI images for each of steps in accordance with an embodiment of the present invention; and FIG. 3B is an exemplary diagram illustrating the sections of the Hippocampus. As shown in FIG. 3A, in this embodiment, the MRI image preprocessing S111 comprising acts of S1110 an intensity normalization, S1111 linear stereotaxic registration, S1112 creating linear mask, S1113 linear classification and S1114 linear segmentations.

In the present disclosure, the acts of S1110 to S1114 for preprocessing and segmenting the MRI images are proceed by a computer using FreeSurfer. FreeSurfer is a software for the analysis and visualization of structural and functional neuroimaging data from cross-sectional or longitudinal studies. It is developed by the Laboratory for Computational Neuroimaging at the Athinoula A. Martinos Center for Biomedical Imaging at Massachusetts General Hospital. For structural MRI image, FreeSurfer provides a cortical and subcortical full processing pipeline describing as following:

1. Intensity correction, noise filtering, artifact correction, skull stripping and gray-white matter segmentation;

The surface-based stream

2. Reconstruction of cortical surface models (gray-white boundary surface);

3. Nonlinear registration of the cortical surface of an individual with a stereotaxic atlas (MNI305 atlas);

The volume-based stream

4. Labeling of cortical regions and subcortical regions;

5. Statistical analysis of group morphometry differences; and

6. Subfields of Hippocampus segmentation.

Therefore, the volume and the sections of Hippocampus is able to obtained by using the MRI image through Free-Surfer. As shown in FIG. 3B, the sections of Hippocampus at least comprise alveus, parasubiculum, presubiculum, subiculum, CA1, CA2/3, CA4, GC-DG, HATA, fimbria, molecular layer, Hippocampus fissure and Hippocampus tail.

Figure 4A:
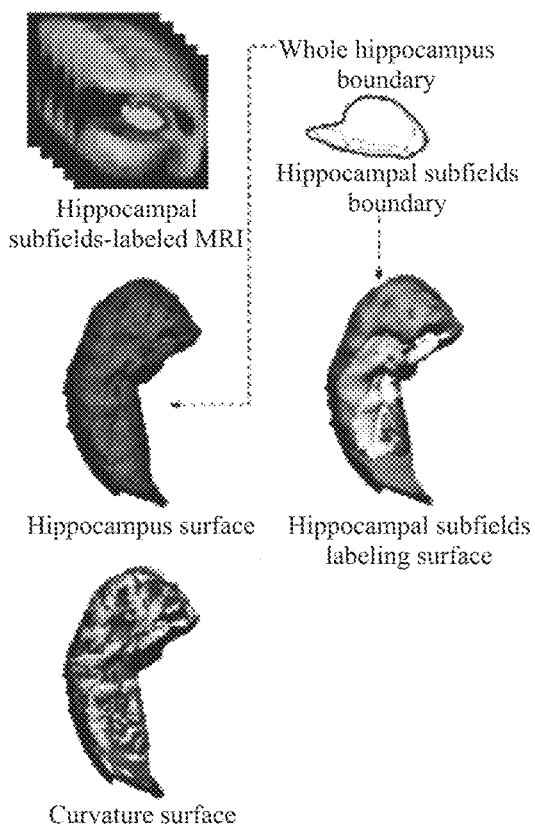
FIG. 4A is an exemplary diagram of a 3D Hippocampus model in accordance with an embodiment of the present invention.
Figure 4B:
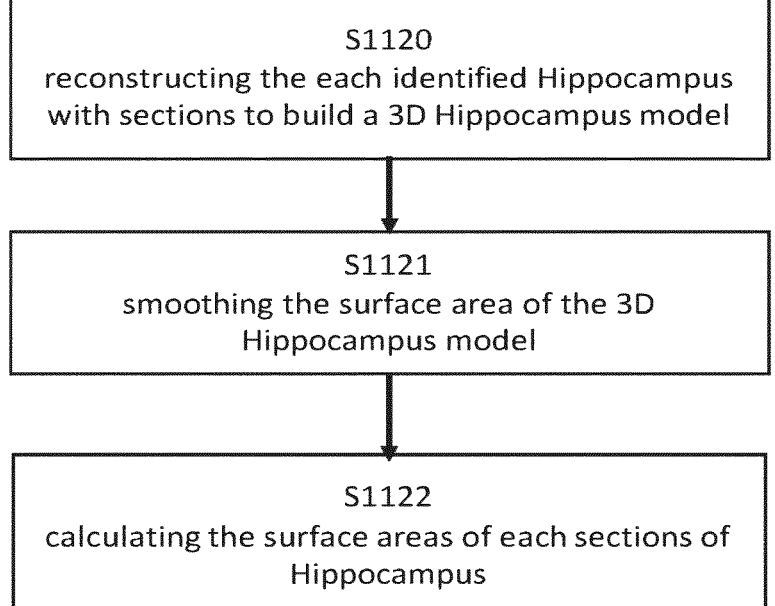
FIG. 4B is a flowchart illustrating the step of S112 in accordance with an embodiment of the present invention.

With reference to FIGS. 4A and 4B, FIG. 4A is an exemplary diagram of a 3 Dimensions (3D) Hippocampus model in accordance with an embodiment of the present invention; and FIG. 4B is a flowchart illustrating the step of S112 in accordance with an embodiment of the present invention. In act of S112, the Hippocampus is built in a 3D Hippocampus model with each identical section. In this embodiment, the 3D Hippocampus model is built by Marching cubes. The "marching cubes" described here is the technique directing to a patent, U.S. Pat. No. 4,710,876 "System And Method For The Display Of Surface Structures Contained Within The Interior Region Of A Solid Body" by Harvey E. Cline and William E. Lorensen, issued on Dec. 1, 1987, the entire contents of which are hereby incorporated by reference.

As shown in FIG. 4A, a block of volumetric data is displayed, it determines interfaces between adjacent data values indicating a change in the measured value, and then models the surfaces with triangular elements having a vector normal to the surface at each of the vertices of the triangle.

Laplacian smoothing is then applied to the 3D Hippocampus model which is configured for improving the quality of the triangulation while remaining faithful to the original surface geometry. The Hippocampus surface and each surface areas of the sections are obtained after the surface smoothing. Therefore, as shown in FIG. 4B, the act of 112 further comprises acts of S1120 reconstructing the each identified Hippocampus with sections to build a 3D Hippocampus model, S1121 smoothing the surface area of the 3D Hippocampus model; and S1122 calculating the surface areas of each sections of Hippocampus. The function of FreeSurfer provides a function of calculating a volume and a surface area of a brain subfield.

Figure 6A:
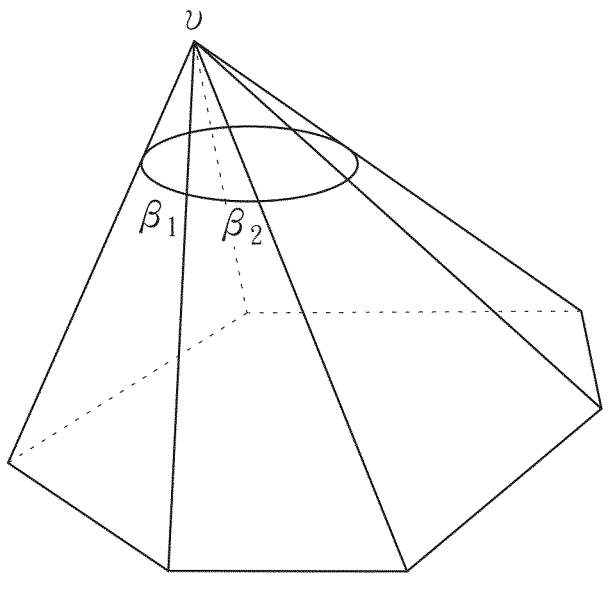
FIG. 6A is an exemplary diagram illustrating the curvature calculation on the discrete surface in accordance with some embodiments of the present invention.
Figure 6B:
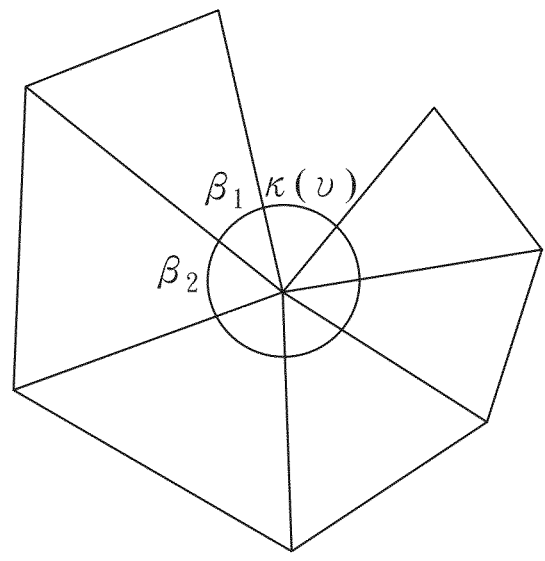
FIG. 6B is an exemplary diagram illustrating the curvature calculation on the discrete surface in accordance with some embodiments of the present invention.

In act of S113, a curvature analysis to the 3D Hippocampus model is proceeded to determine an average of a Ratio of Principle Curvature (RPC) for each section of the hippocampus. In the following, the definition and the calculation of the maximum principal curvature, the minimum principal curvature, and the ratio of principal curvatures for each section of the hippocampus are discussed. The discretizing mesh on discrete surface is not smooth enough for defining curvature. It is not differentiable along the edges. However, if the mesh is fine enough, you can use difference schemes to approximate the derivatives, and also the curvatures. This technique belongs to numerical analysis. Under certain assumption including the smoothness via derivatives, and the resolution of the mesh, we can approximate the Gaussian curvature and the mean curvature on a discrete surface by the Gauss-Bonnet theorem. FIG. 6A and FIG. 6B are diagrams illustrating the curvature calculation on the discrete surface in accordance with some embodiments of the present invention. Please refer to FIG. 6A and FIG. 6B, the approximated value of the Gaussian curvature, K(v), at vertex v is equal to the angle defect, d(v), of vertices v:

$$K(v) = d(v) = 2\pi - \sum_{i=0}^{N} \beta_i \qquad \text{(eq1)}$$

where, N is the number of faces containing v, and is the interior angle of v. In this embodiment, the mean curvature, H(v), can also be calculated:

$$H(e) = \frac{1}{N} \sum_{i}^{N} \text{length } (e) * \Psi(e) \qquad \text{(eq2)}$$

where edge e is incident to vertex v, and v is the number of incident edges. Here, length(e) denotes the length of edge e, and Ψ(e) denotes the dihedral angle of e as shown in FIG. 6A and FIG. 6B.

In this embodiment, according to (eq1) and (eq2), discrete maximum curvature and discrete minimum curvature (hereinafter, discrete maximum curvature and discrete minimum curvature are referred to as maximum curvature and minimum curvature, respectively) could be defined as follows:

$$C_{max}(v) = H(v) + \sqrt{(H(v))^2 - K(v)} \qquad \text{(eq3)}$$

$$C_{min}(v) = H(v) - \sqrt{(H(v))^2 - K(v)} \qquad \text{(eq4)}$$

The ratio of principal curvatures is defined as follows. Given a point P on a closed surface S, we can define the principal curvatures by the maximum curvature $C_{max}$, and the minimum curvature $C_{min}$. Now, we can define two new curvatures, $$C_{absolute\_max} = \text{Max}\{|C_{max}|, |C_{min}|\} \qquad \text{(eq5)}$$

$$C_{absolute\_min} = \text{Min}\{|C_{max}|, |C_{min}|\} \qquad \text{(eq6)}$$

The ratio of principal curvatures is defined as:

$$RPC = \frac{C_{absolute\_max}}{C_{absolute\_min}} \qquad \text{(eq6)}$$

Figure 7:
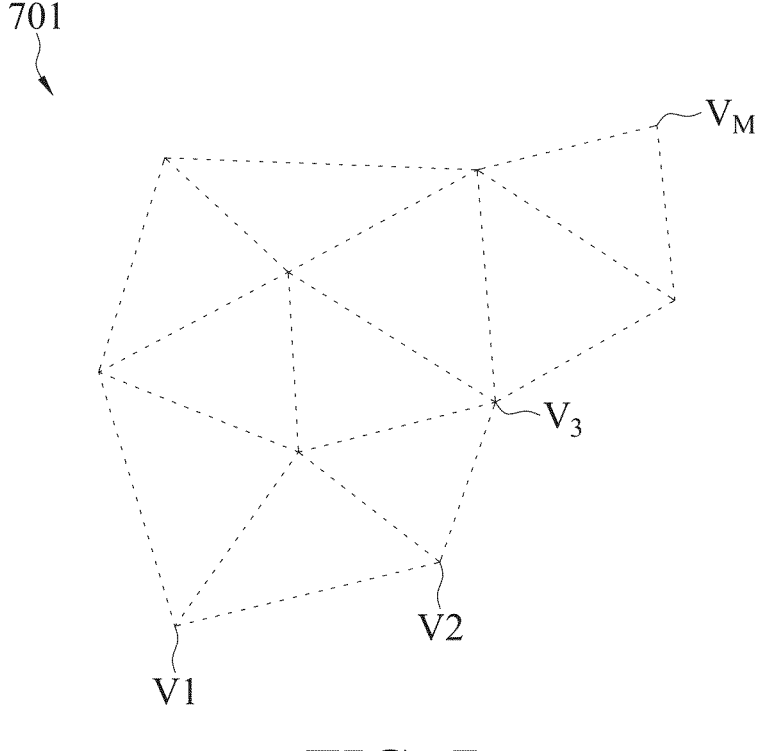
FIG. 7 is an exemplary diagram illustrating meshes of a 3D model surface in accordance with some embodiments of the present invention.
Figure 8A:
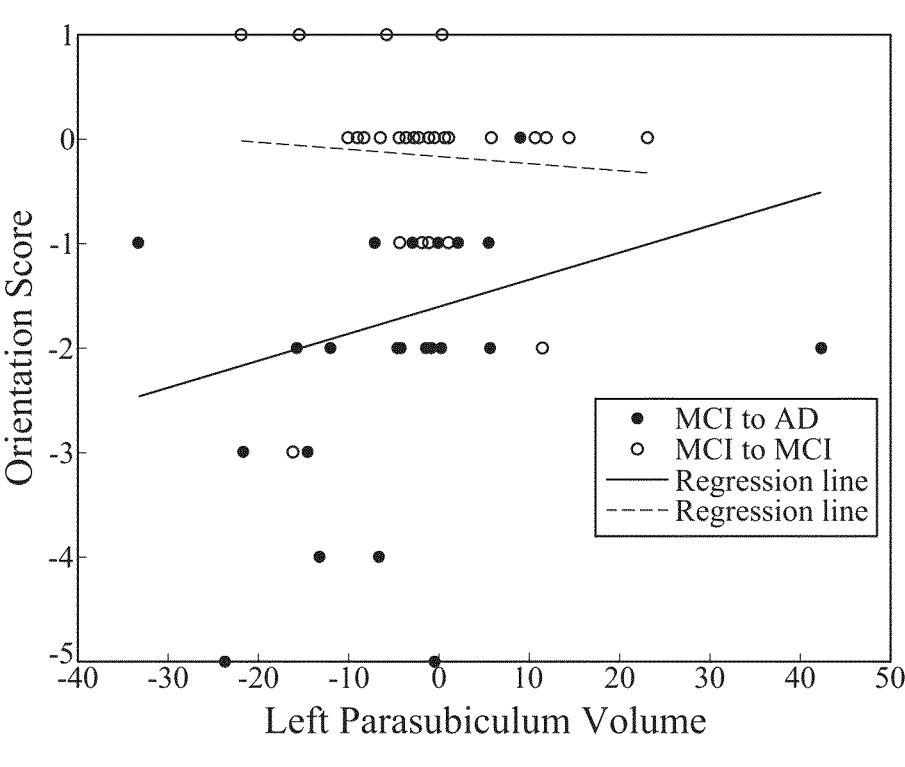
FIG. 8A is an exemplary scatterplot of hippocampal sub-regions' volume vs. orientation in accordance with some embodiments of the present invention.
Figure 8A:
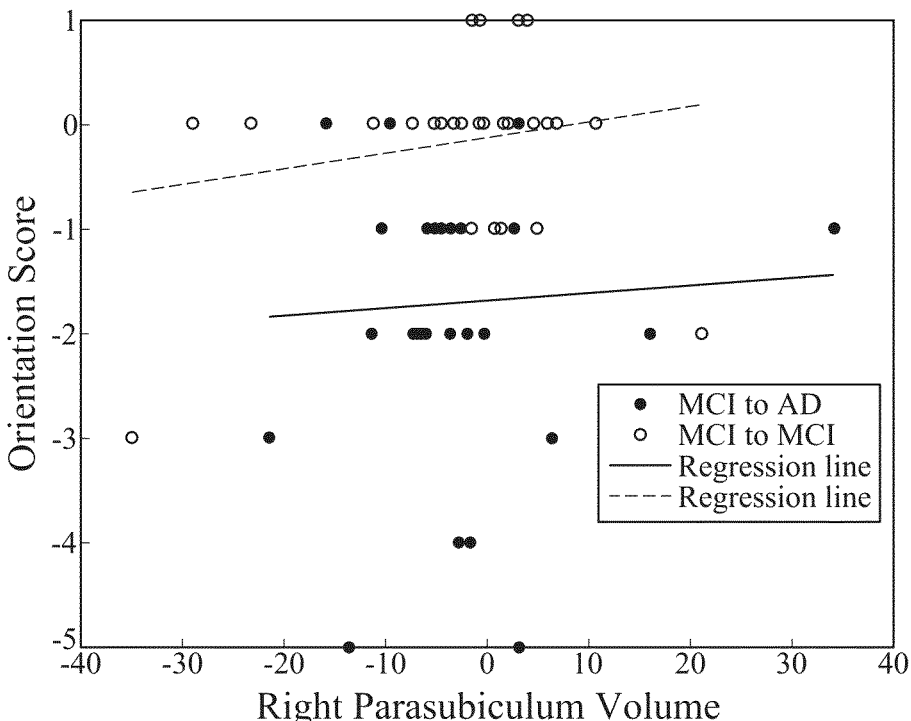
Figure 8B:
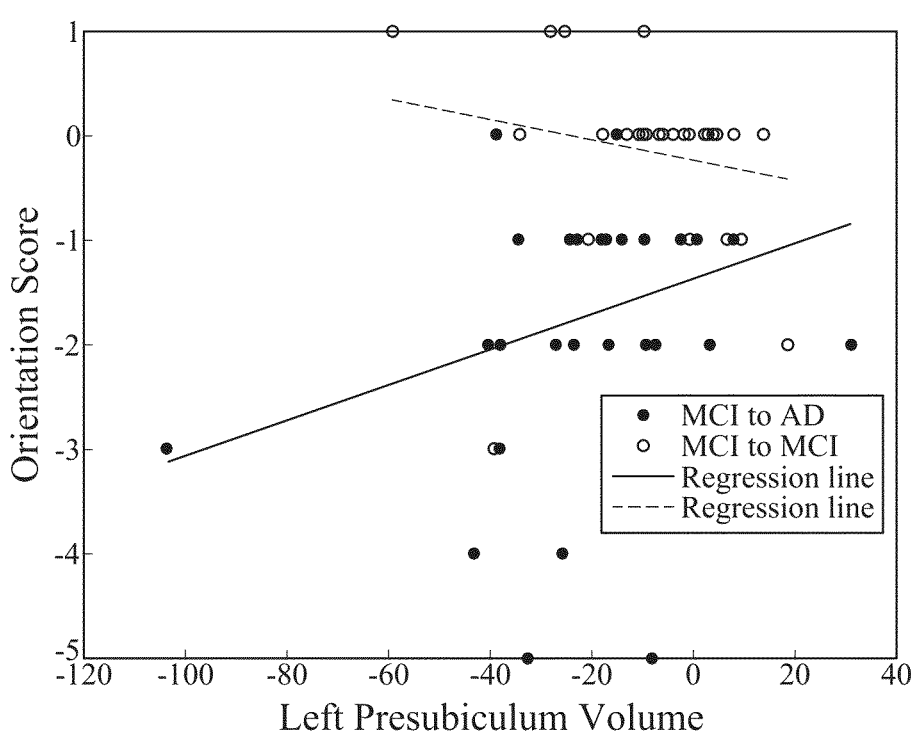
FIG. 8B is an exemplary scatterplot of hippocampal sub-regions' volume vs. orientation in accordance with some embodiments of the present invention.
Figure 8B:
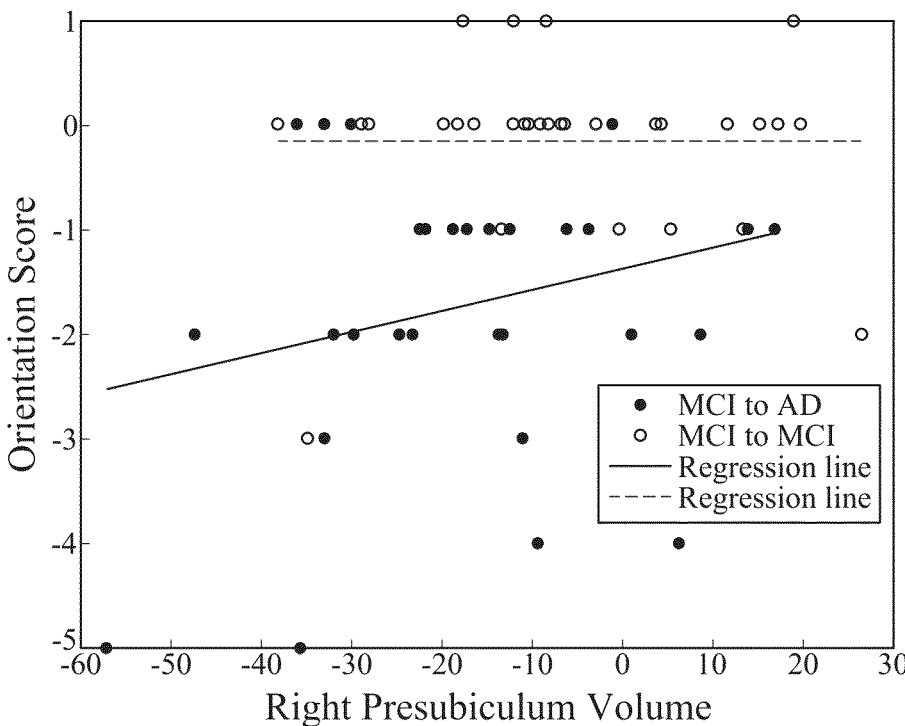
Figure 8C:
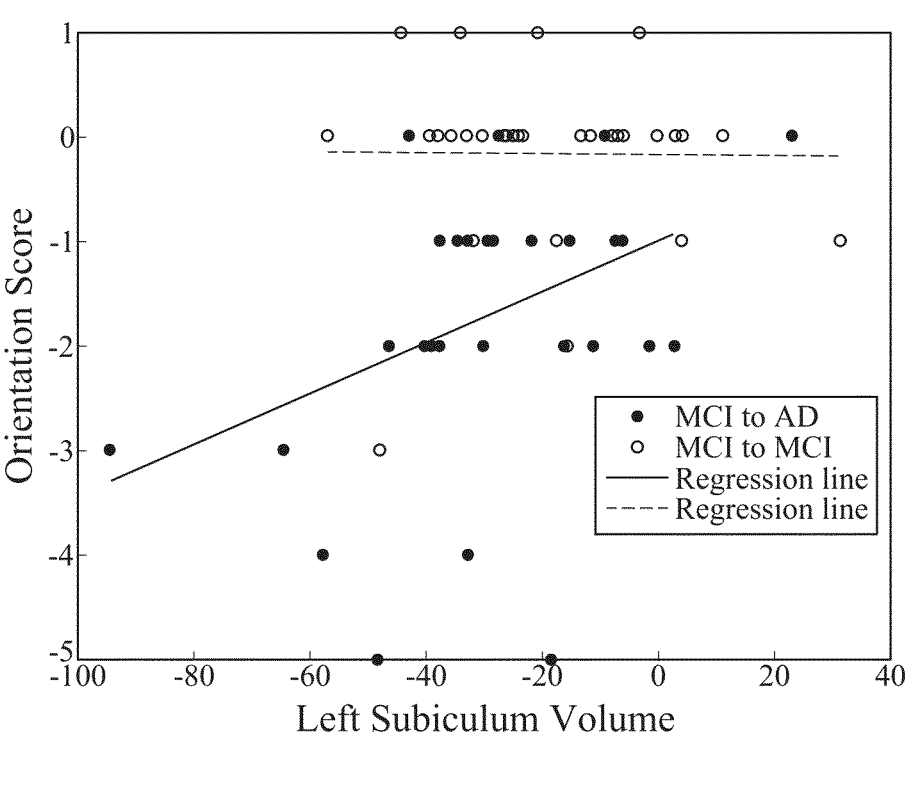
FIG. 8C is an exemplary scatterplot of hippocampal sub-regions' volume vs. orientation in accordance with some embodiments of the present invention.
Figure 8C:
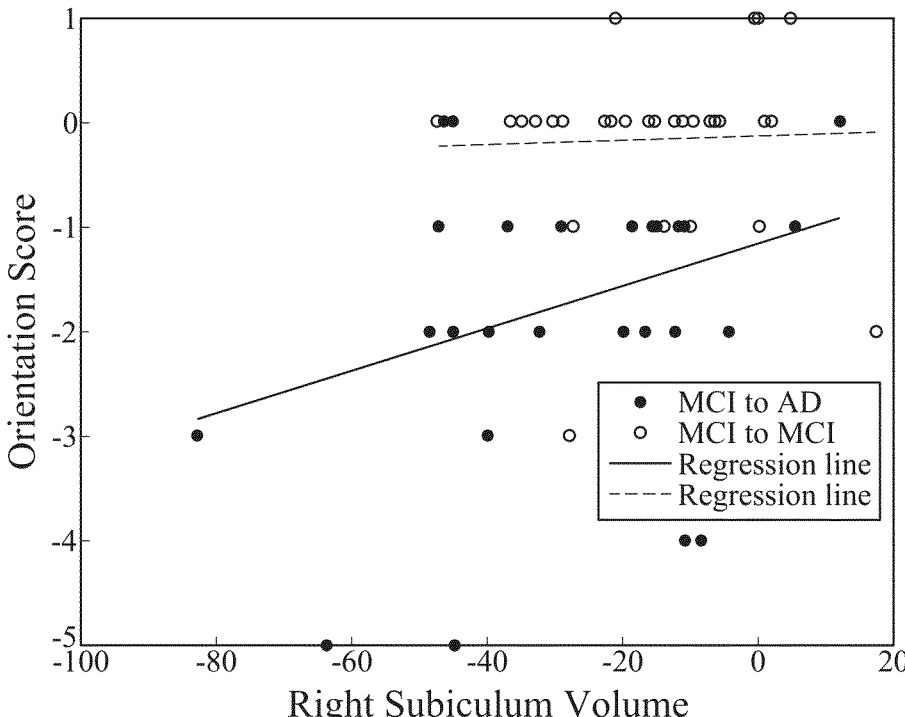
Figure 8D:
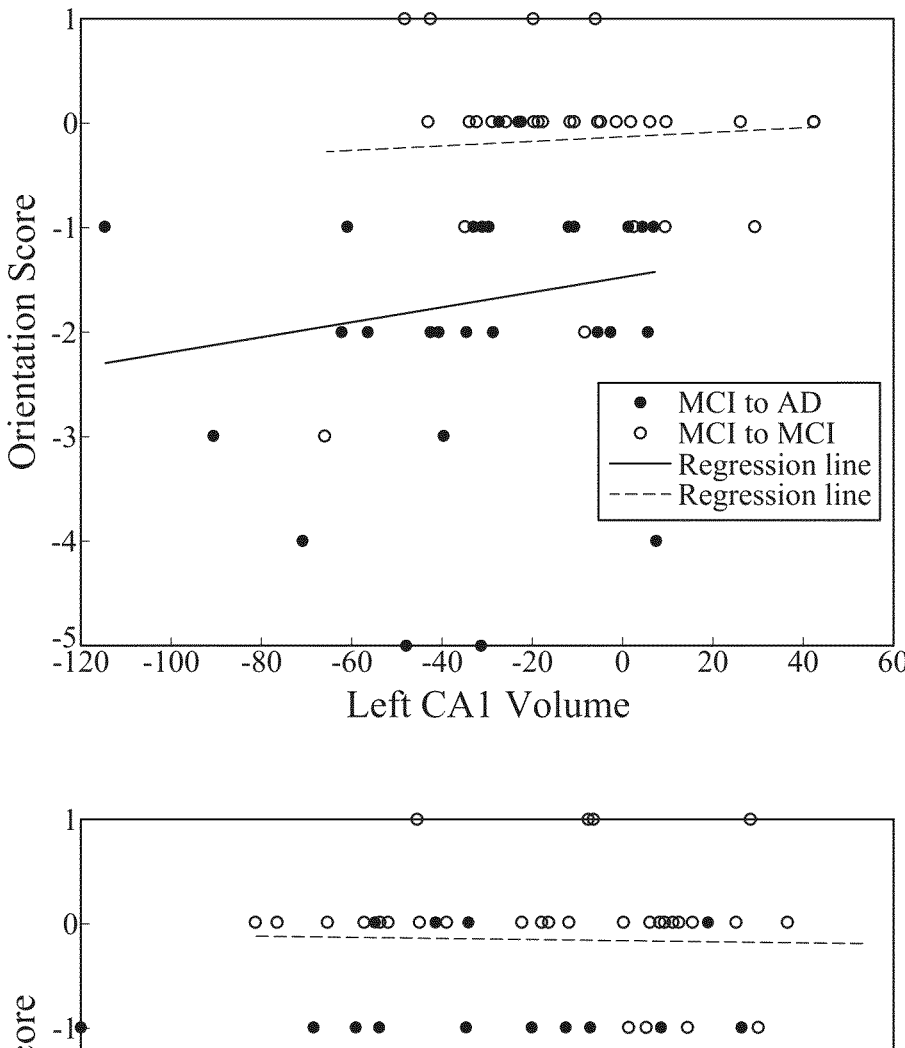
FIG. 8D is an exemplary scatterplot of hippocampal sub-regions' volume vs. orientation in accordance with some embodiments of the present invention.
Figure 8E:
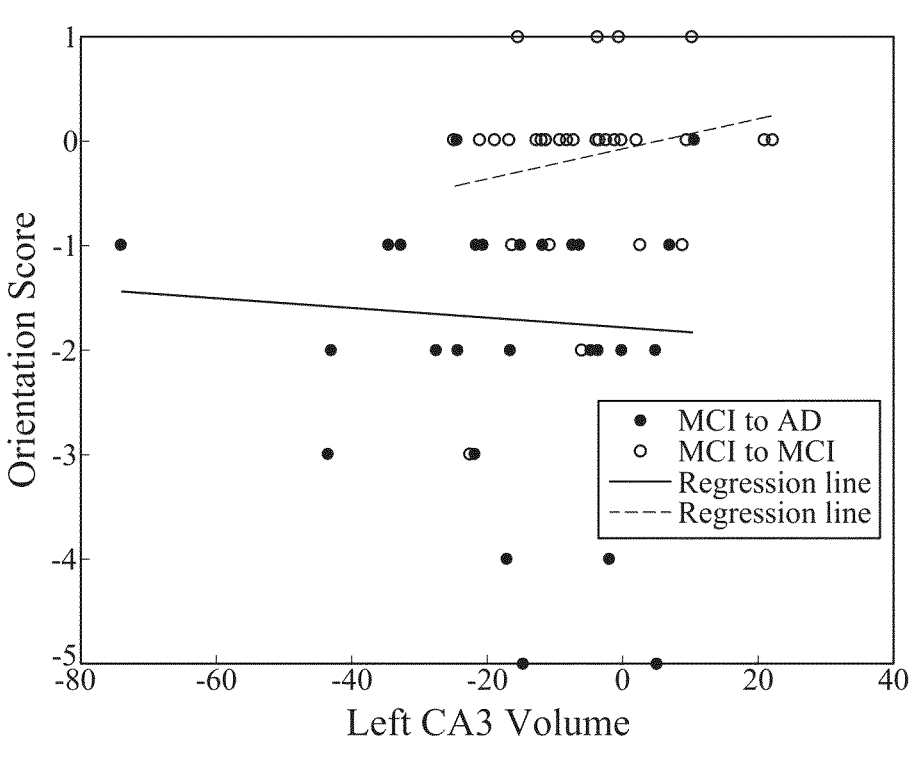
FIG. 8E is an exemplary scatterplot of hippocampal sub-regions' volume vs. orientation in accordance with some embodiments of the present invention.
Figure 8E:
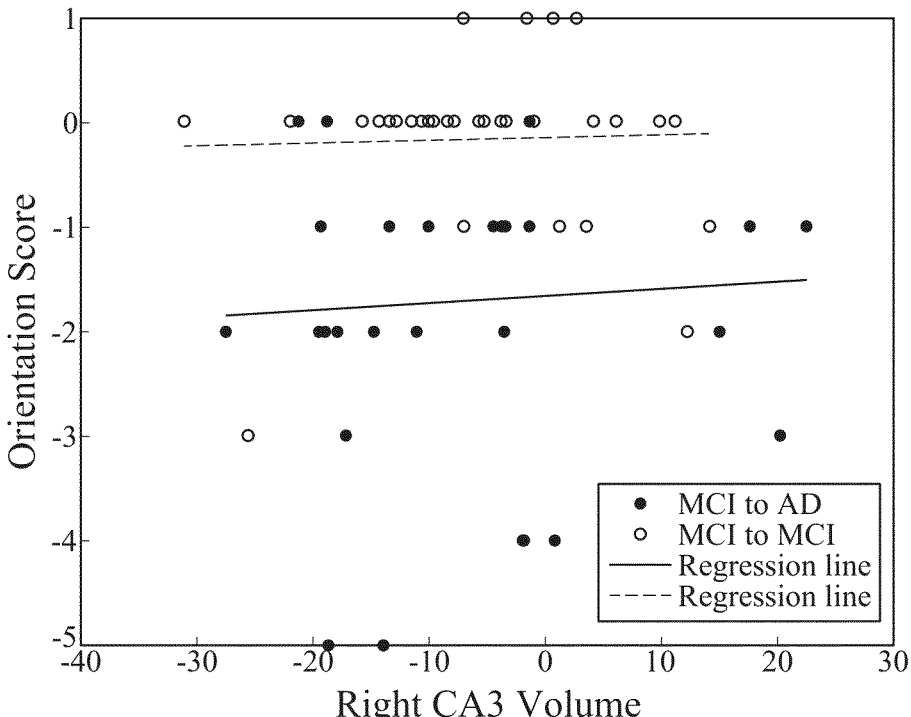
Figure 8F:
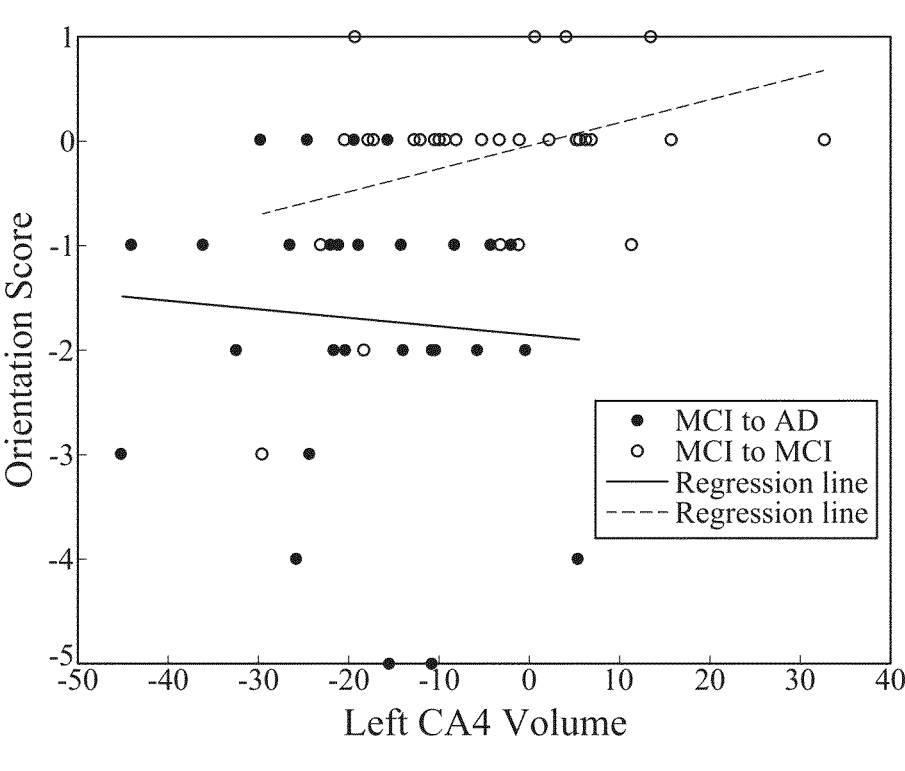
FIG. 8F is an exemplary scatterplot of hippocampal sub-regions' volume vs. orientation in accordance with some embodiments of the present invention.
Figure 8F:
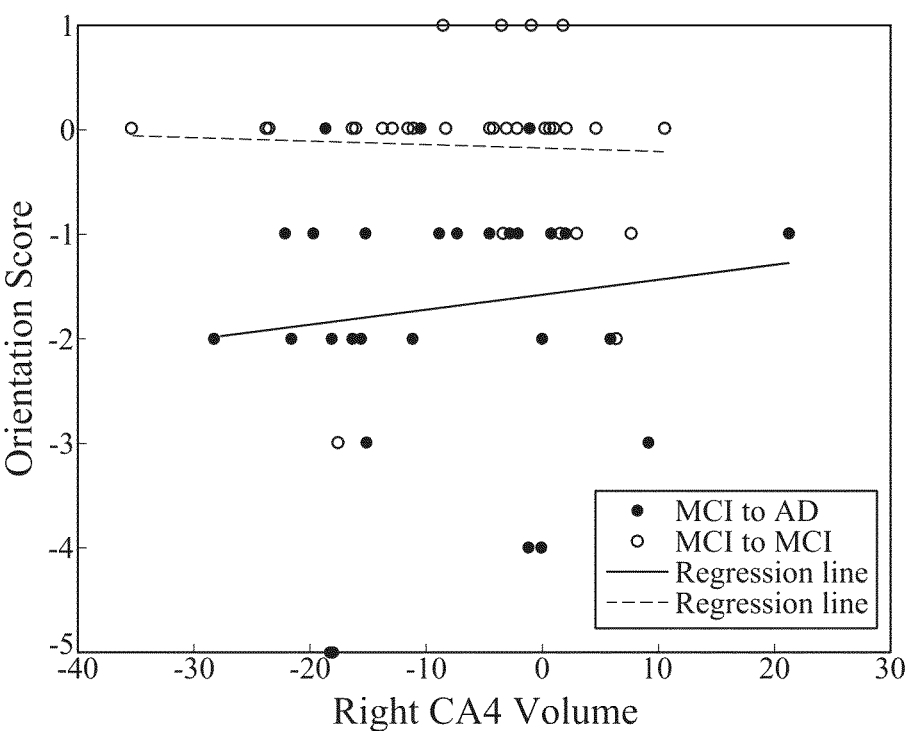
Figure 8G:
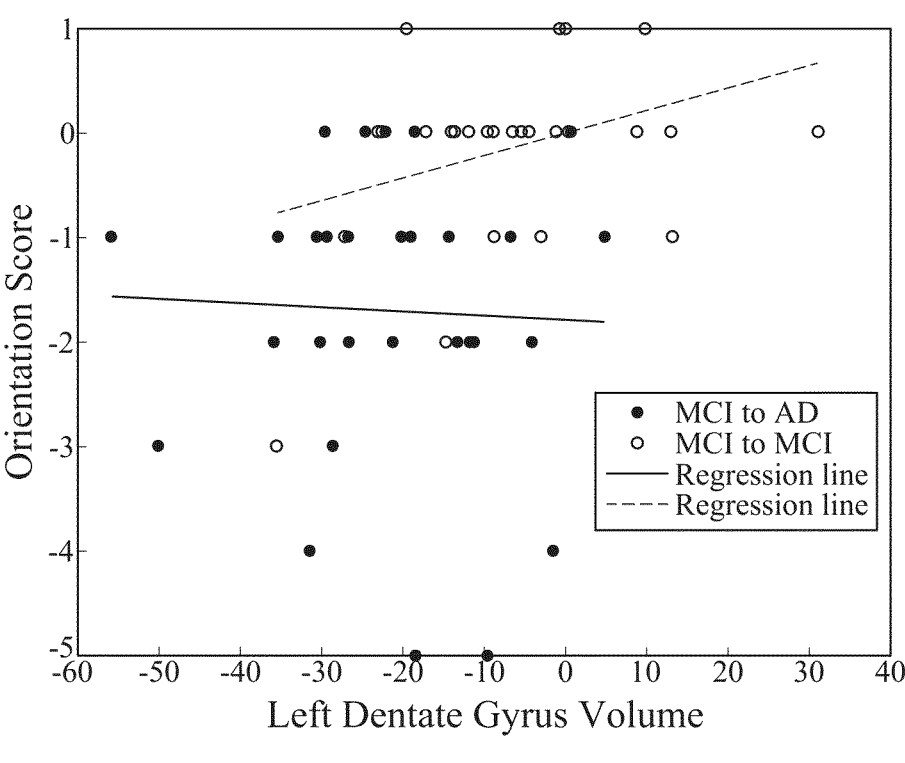
FIG. 8G is an exemplary scatterplot of hippocampal sub-regions' volume vs. orientation in accordance with some embodiments of the present invention.
Figure 8G:
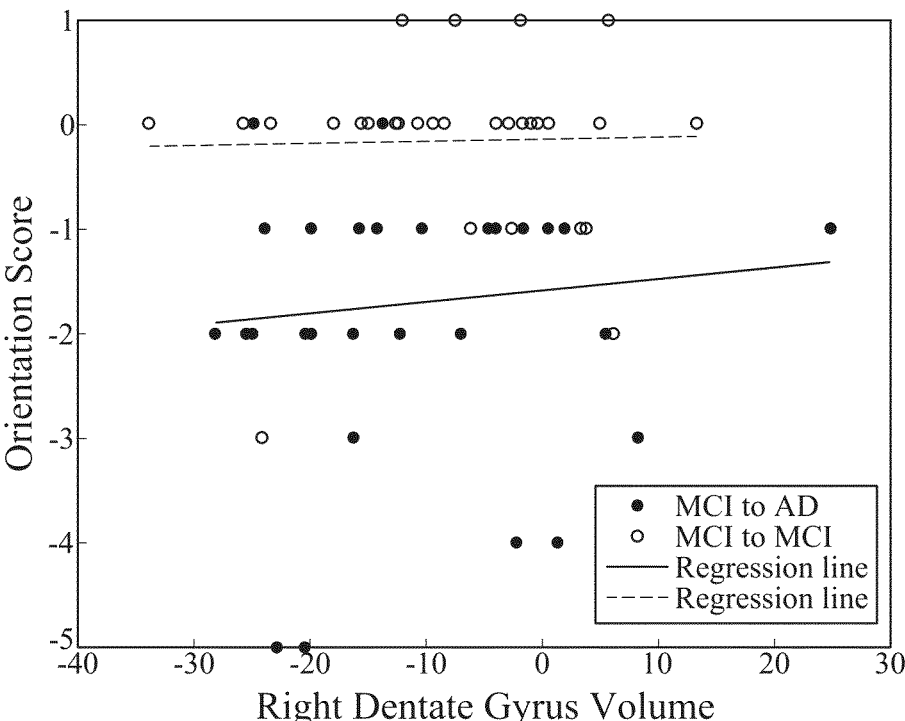
Figure 8H:
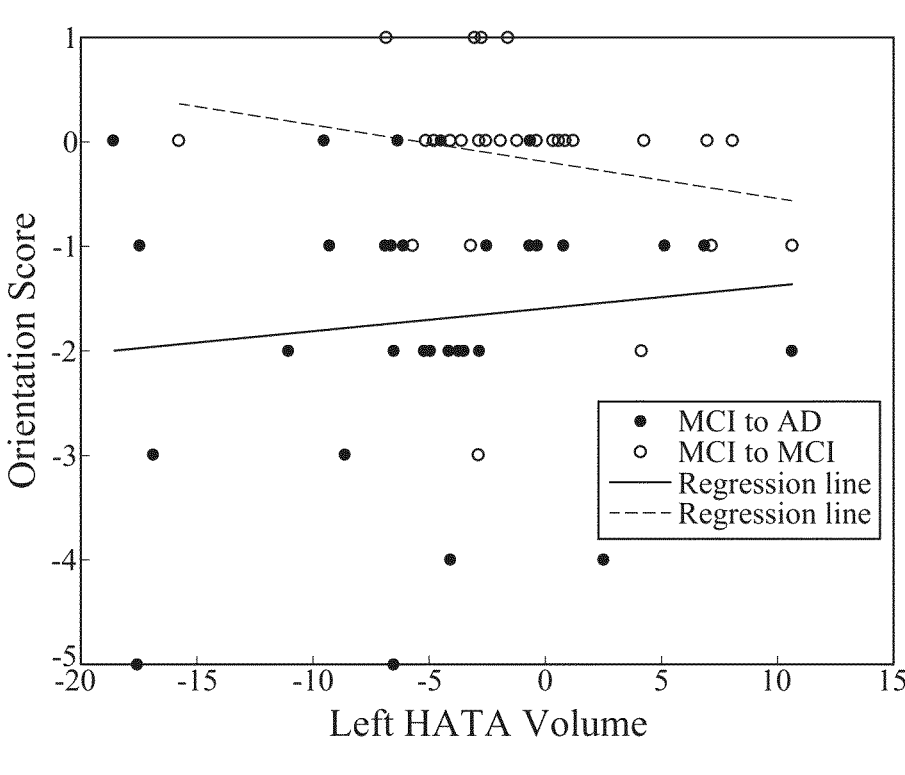
FIG. 8H is an exemplary scatterplot of hippocampal sub-regions' volume vs. orientation in accordance with some embodiments of the present invention.
Figure 8H:
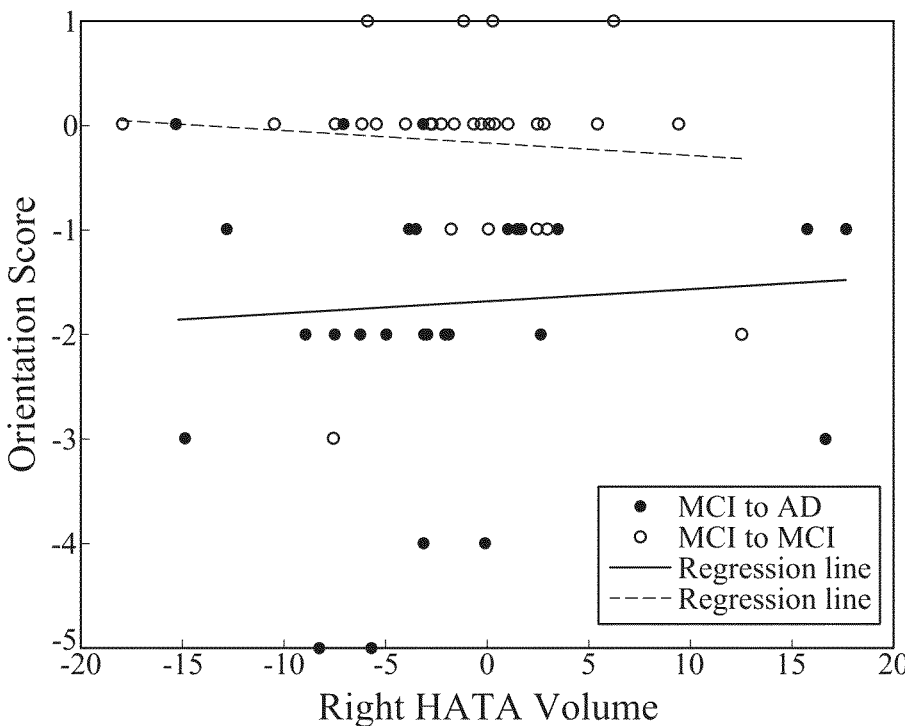
Figure 8I:
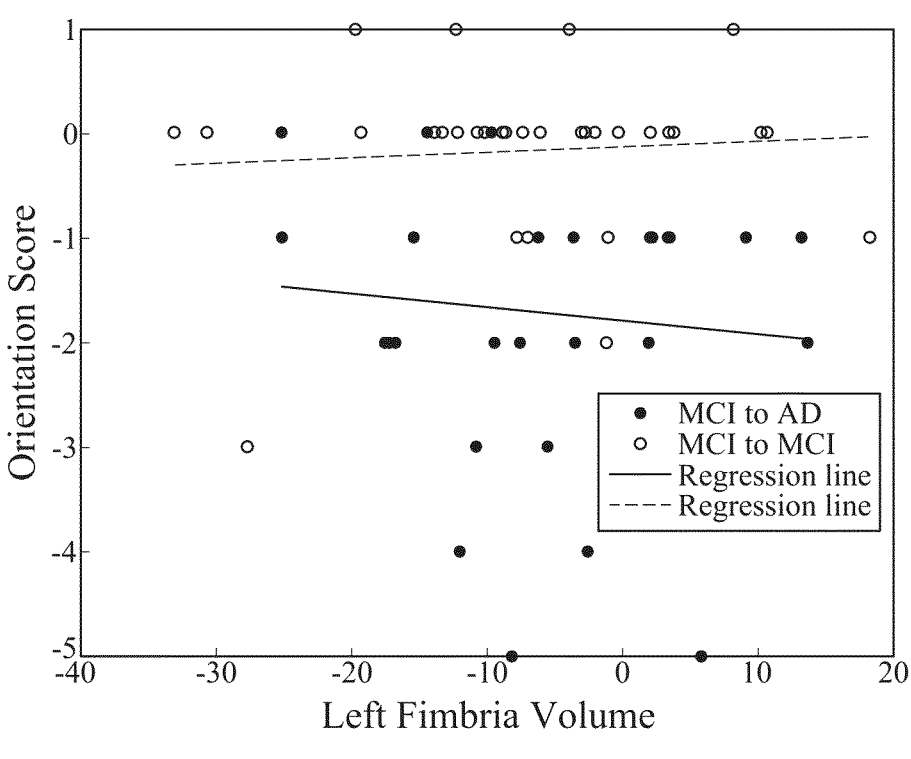
FIG. 8I is an exemplary scatterplot of hippocampal sub-regions' volume vs. orientation in accordance with some embodiments of the present invention.
Figure 8I:
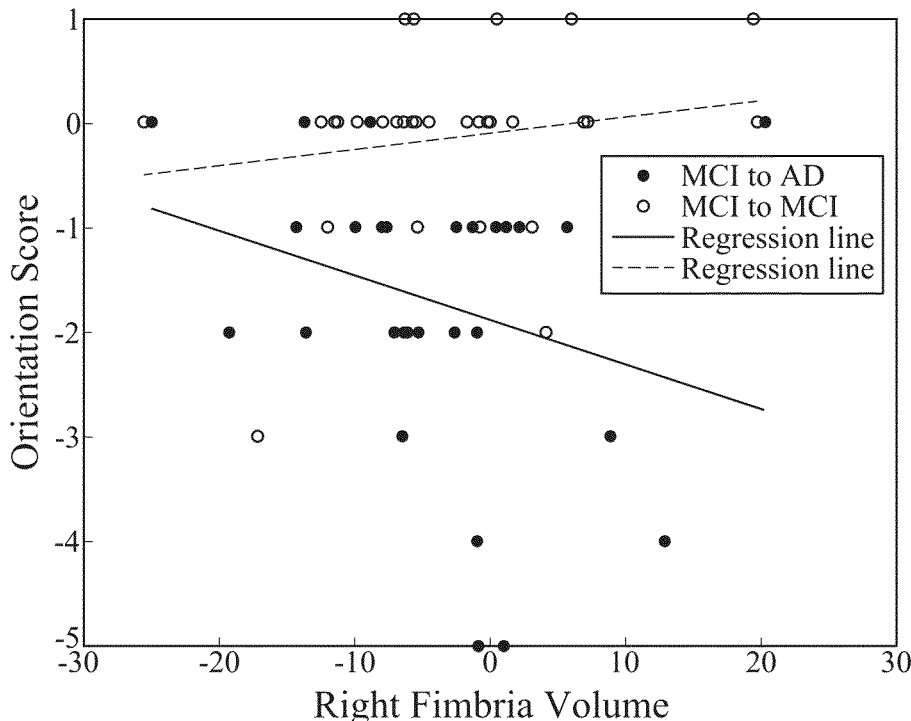
Figure 8J:
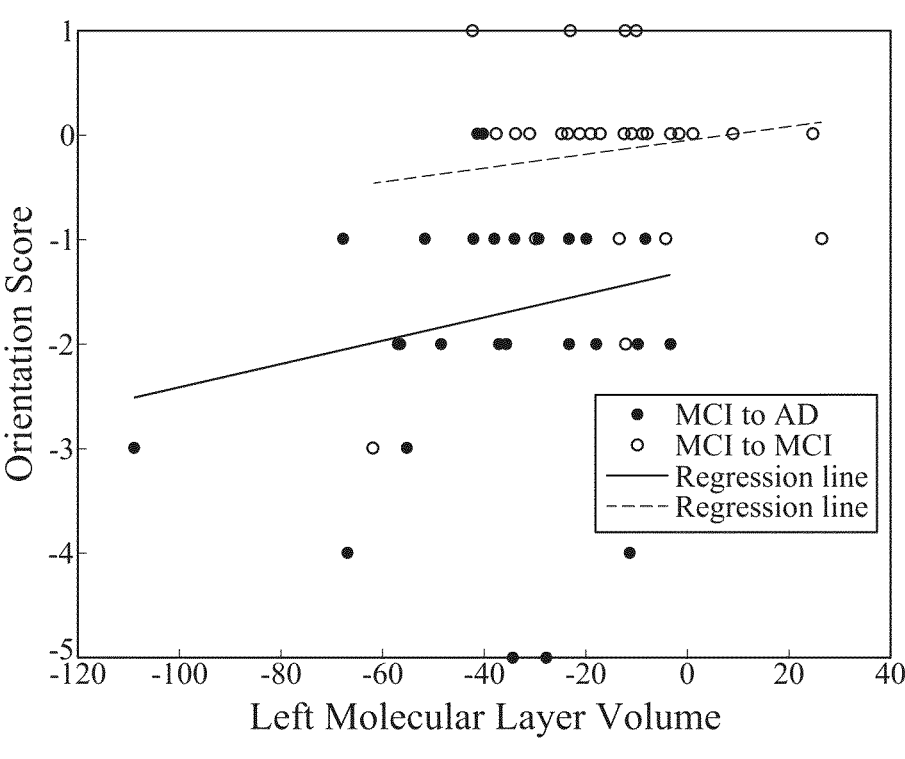
FIG. 8J is an exemplary scatterplot of hippocampal sub-regions' volume vs. orientation in accordance with some embodiments of the present invention.
Figure 8J:
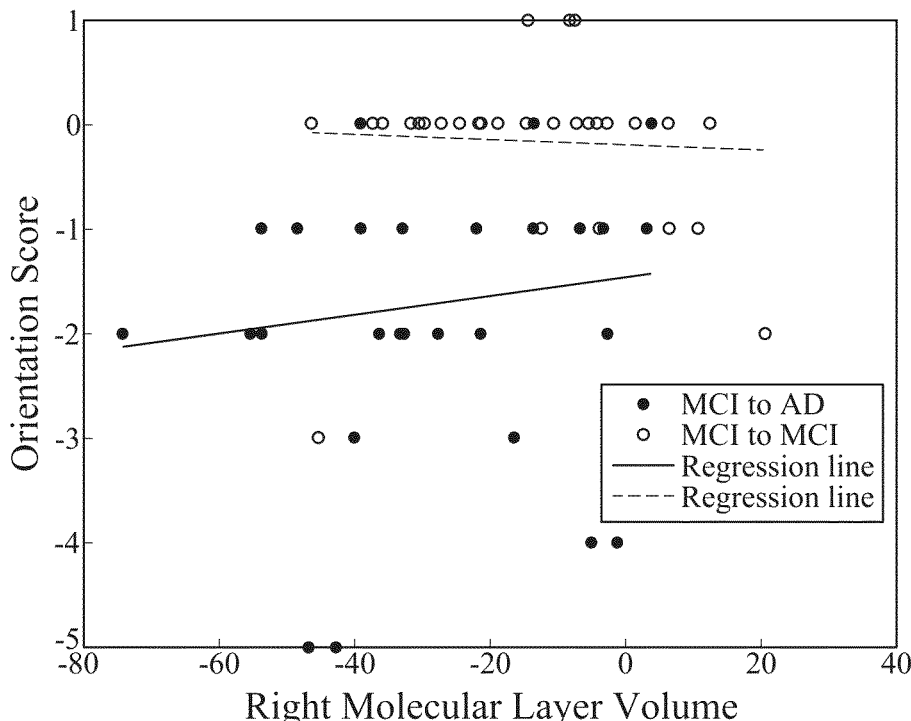
Figure 8K:
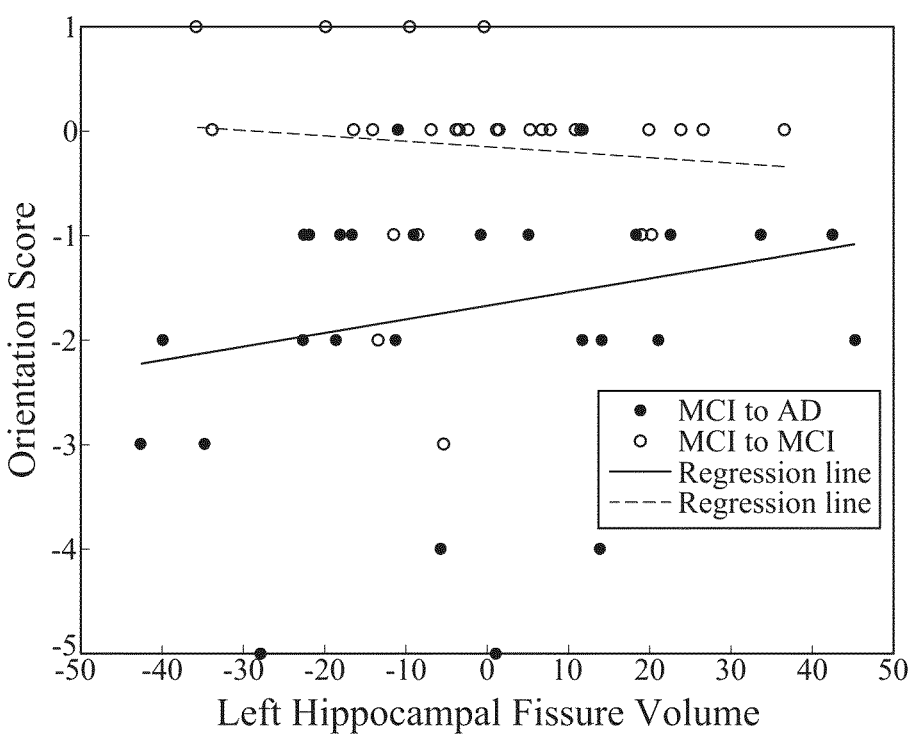
FIG. 8K is an exemplary scatterplot of hippocampal sub-regions' volume vs. orientation in accordance with some embodiments of the present invention.
Figure 8K:
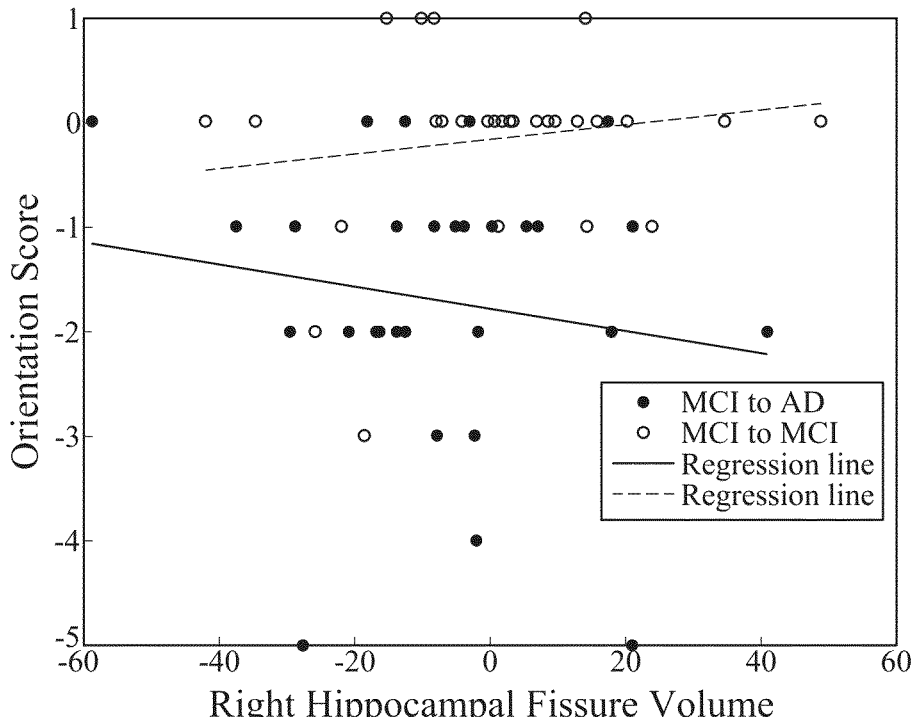
Figure 8L:
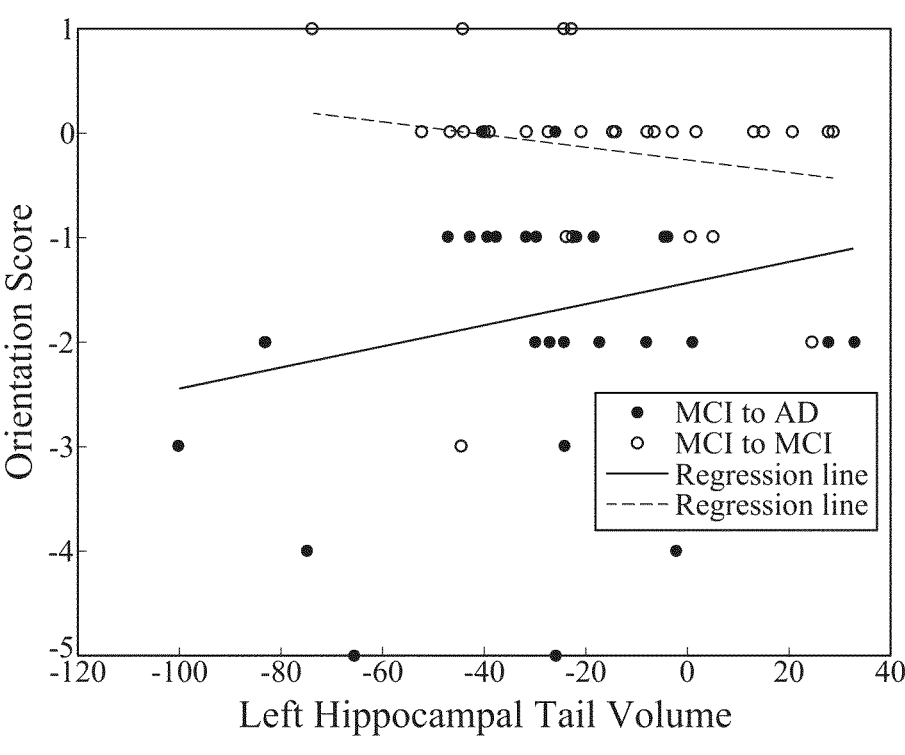
FIG. 8L is an exemplary scatterplot of hippocampal sub-regions' volume vs. orientation in accordance with some embodiments of the present invention.
Figure 8L:
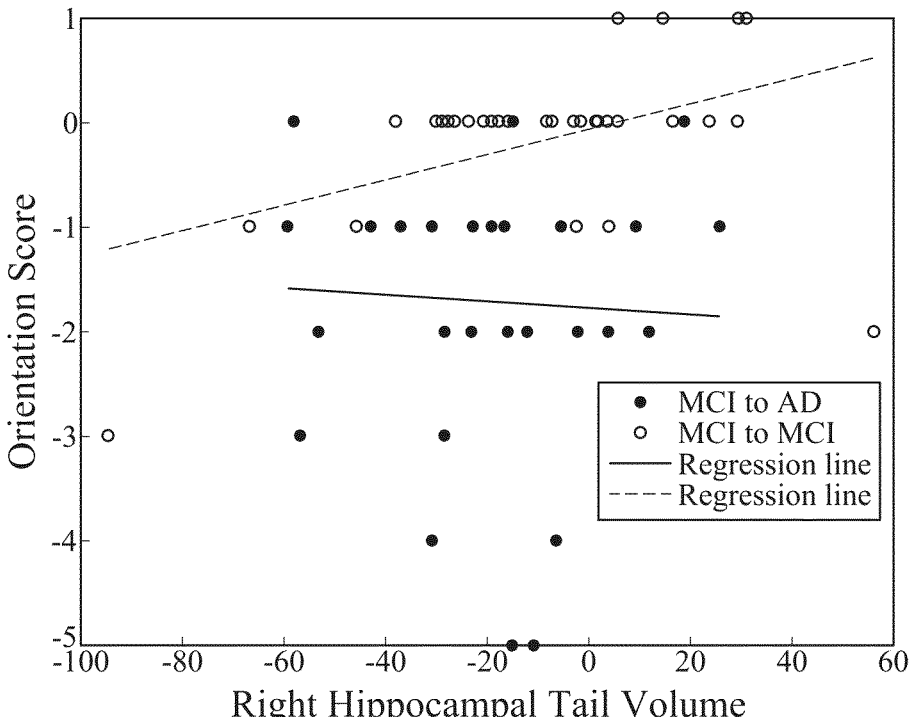
Figure 9A:
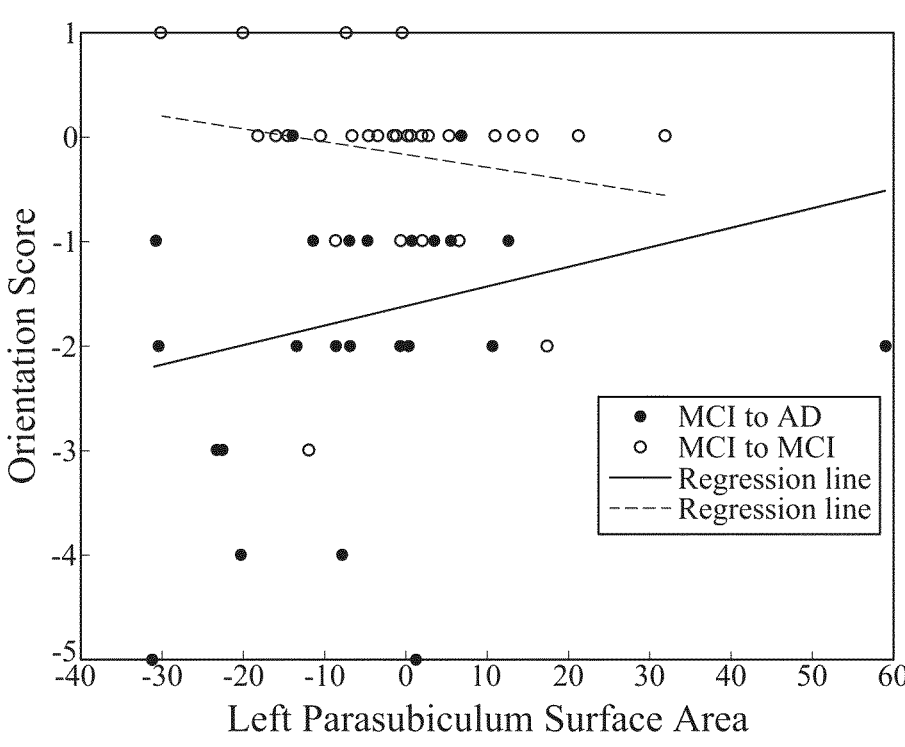
FIG. 9A is an exemplary scatterplot of hippocampal sub-regions' surface area vs. orientation in accordance with some embodiments of the present invention.
Figure 9A:
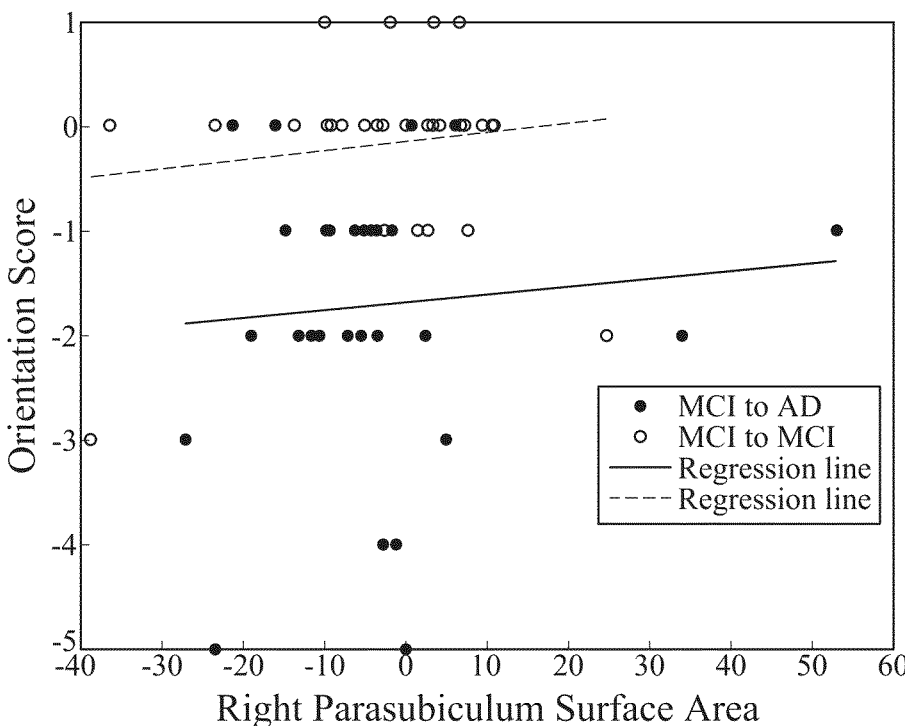
Figure 9B:
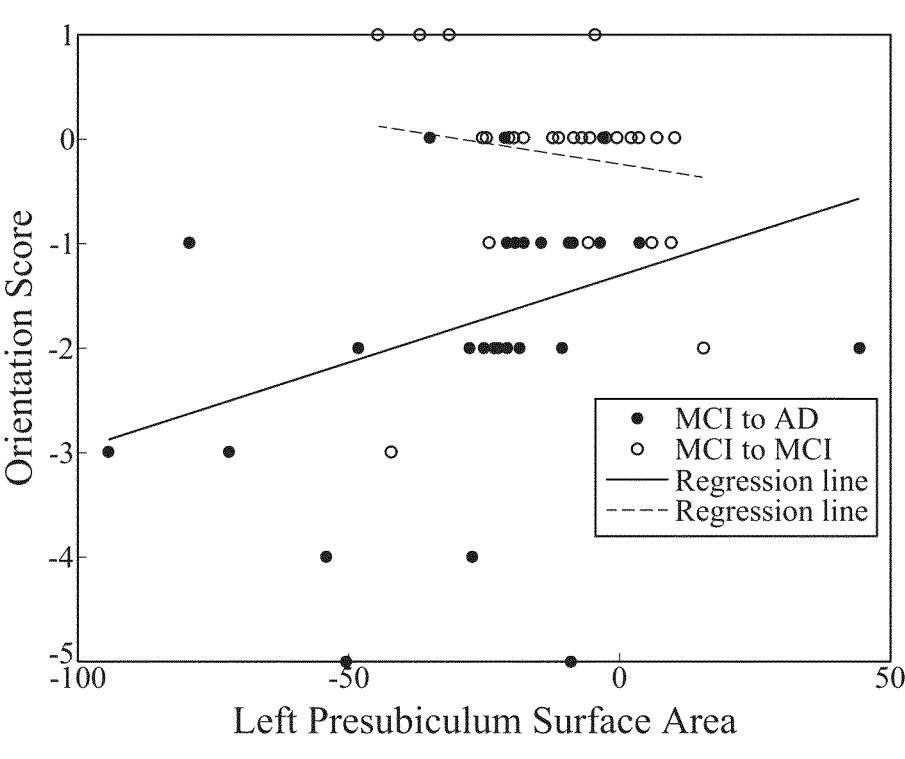
FIG. 9B is an exemplary scatterplot of hippocampal sub-regions' surface area vs. orientation in accordance with some embodiments of the present invention.
Figure 9B:
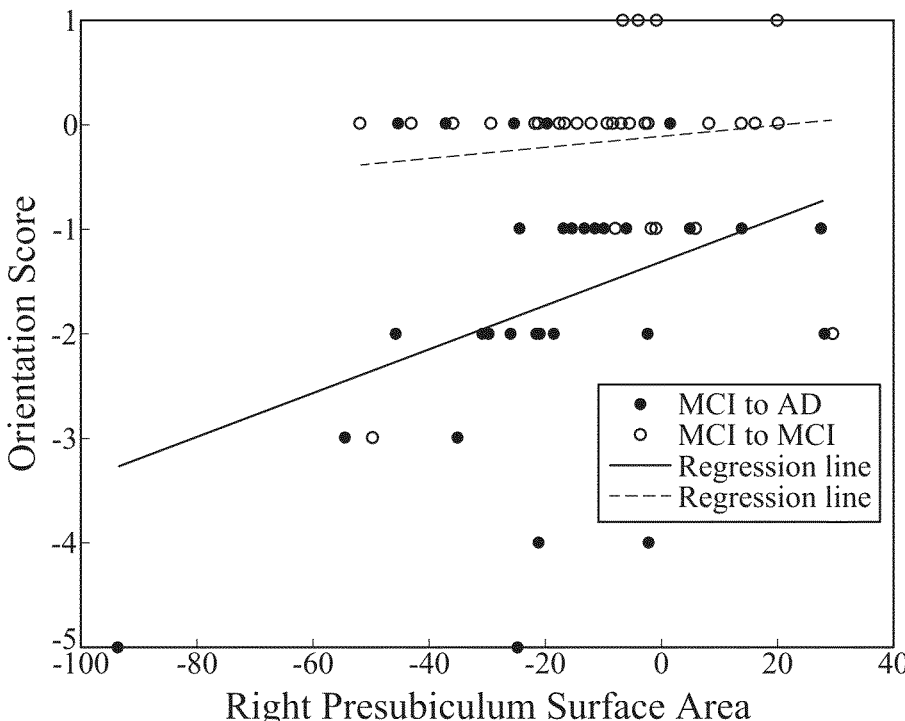
Figure 9C:
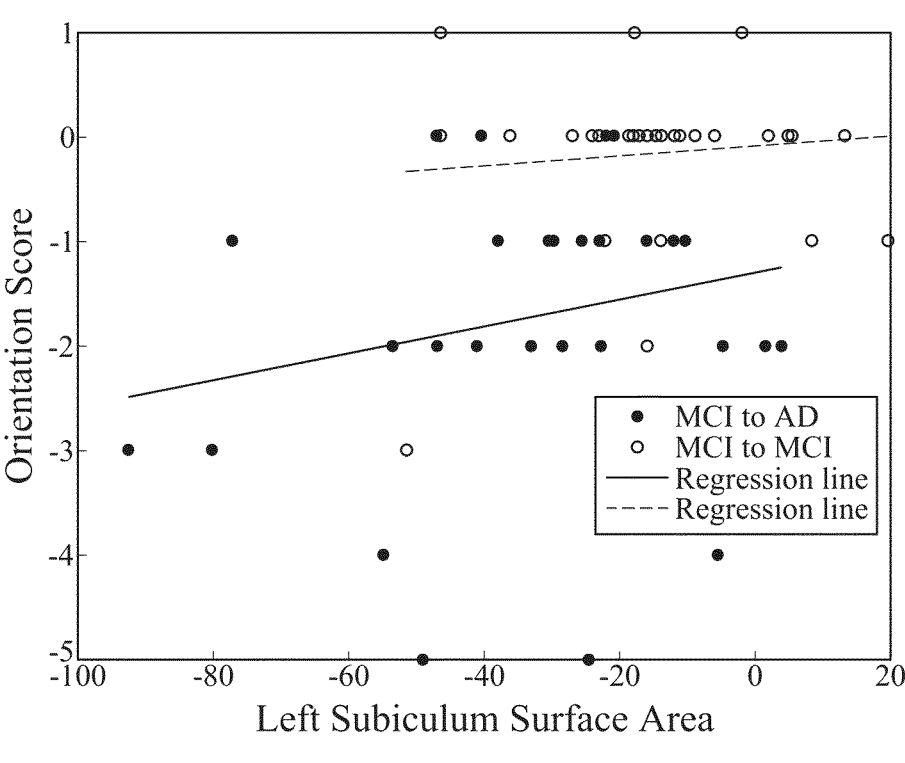
FIG. 9C is an exemplary scatterplot of hippocampal sub-regions' surface area vs. orientation in accordance with some embodiments of the present invention.
Figure 9C:
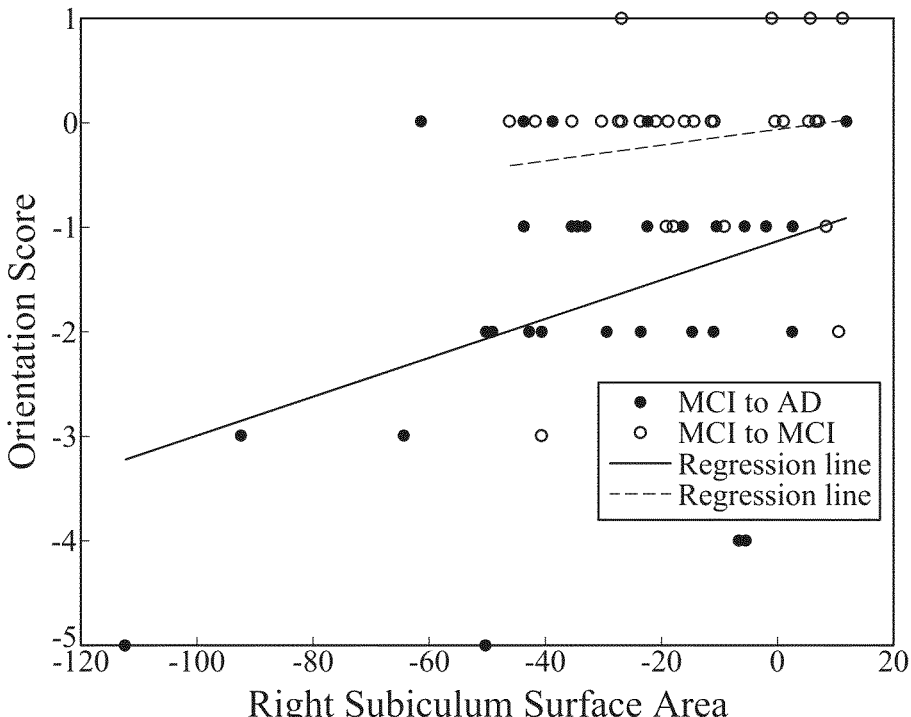
Figure 9D:
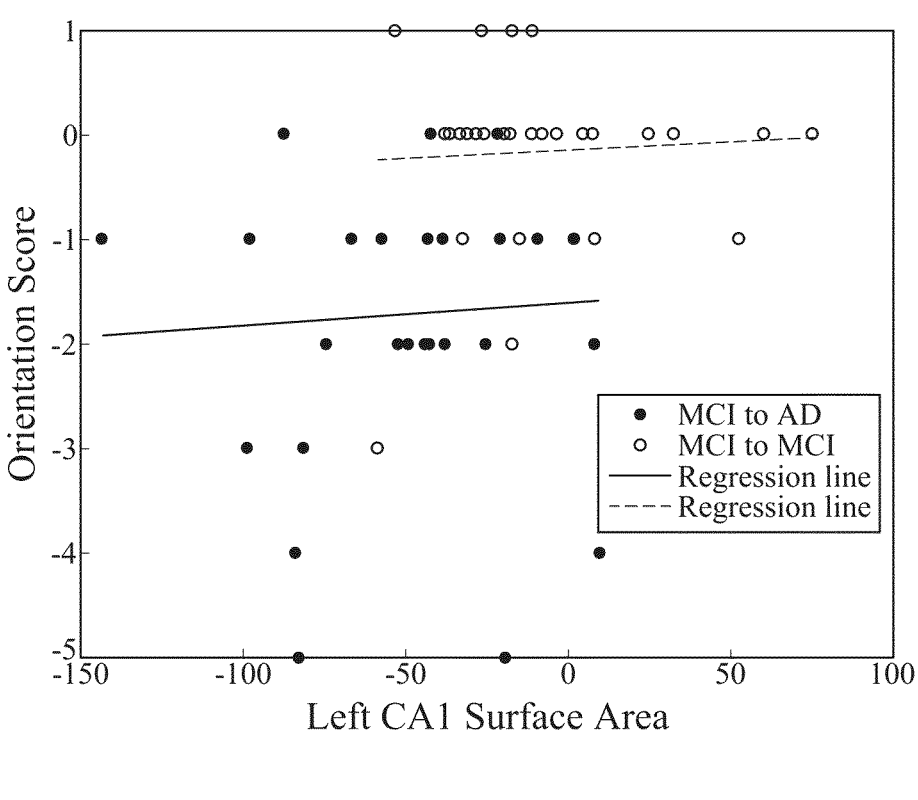
FIG. 9D is an exemplary scatterplot of hippocampal sub-regions' surface area vs. orientation in accordance with some embodiments of the present invention.
Figure 9D:
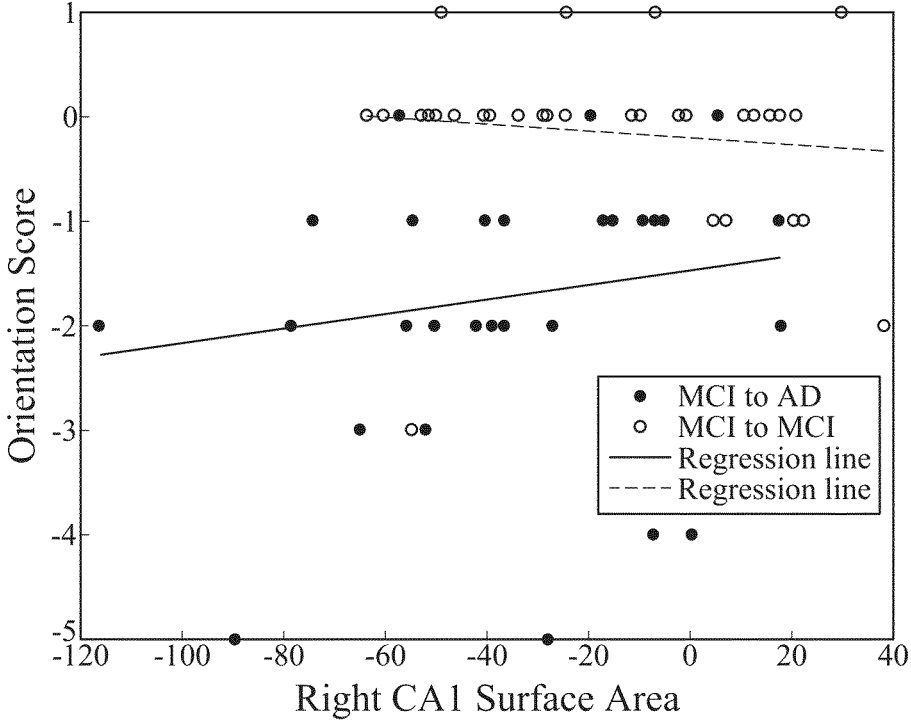
Figure 9E:
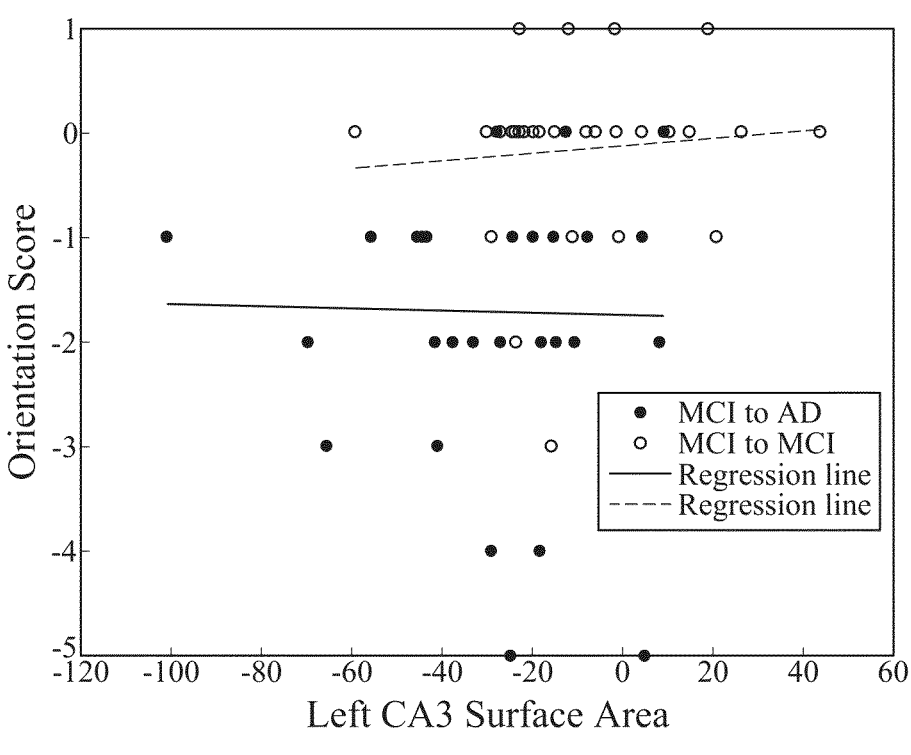
FIG. 9E is an exemplary scatterplot of hippocampal sub-regions' surface area vs. orientation in accordance with some embodiments of the present invention.
Figure 9E:
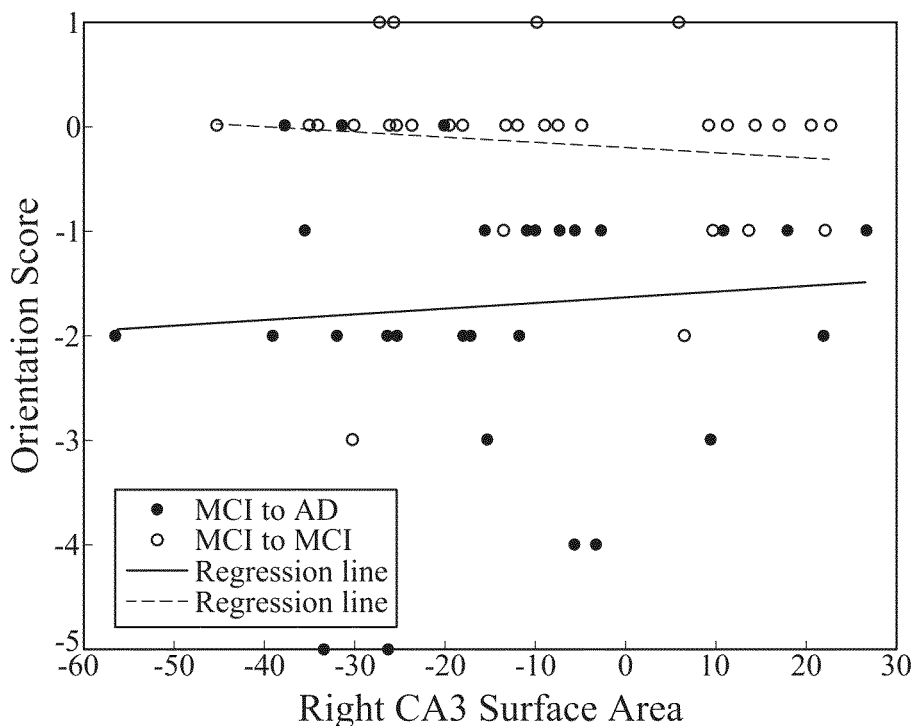
Figure 9F:
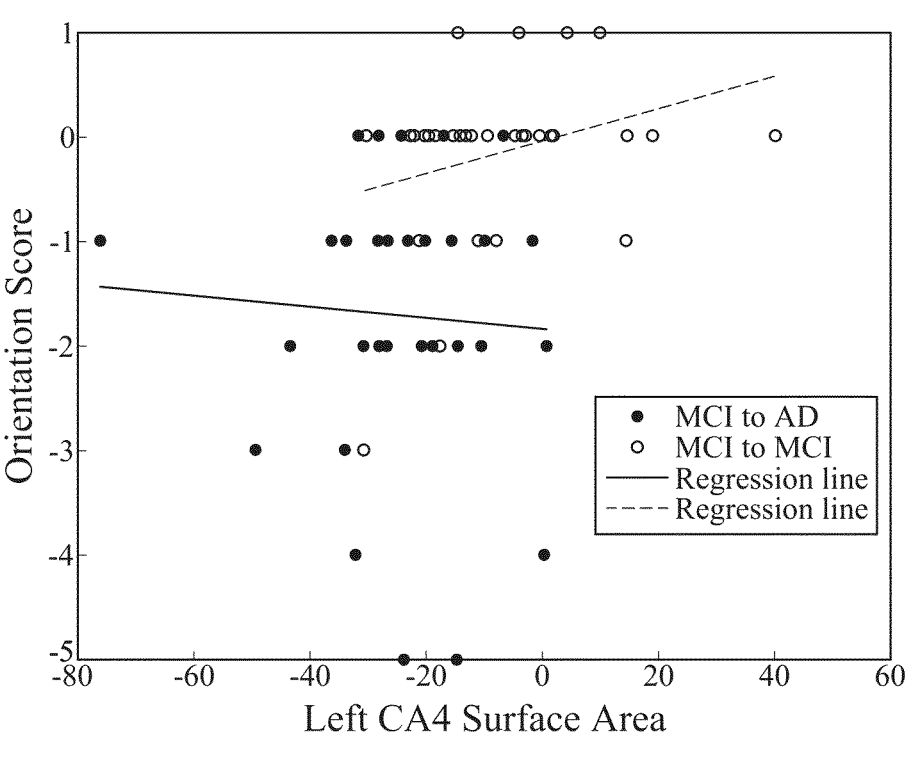
FIG. 9F is an exemplary scatterplot of hippocampal sub-regions' surface area vs. orientation in accordance with some embodiments of the present invention.
Figure 9F:
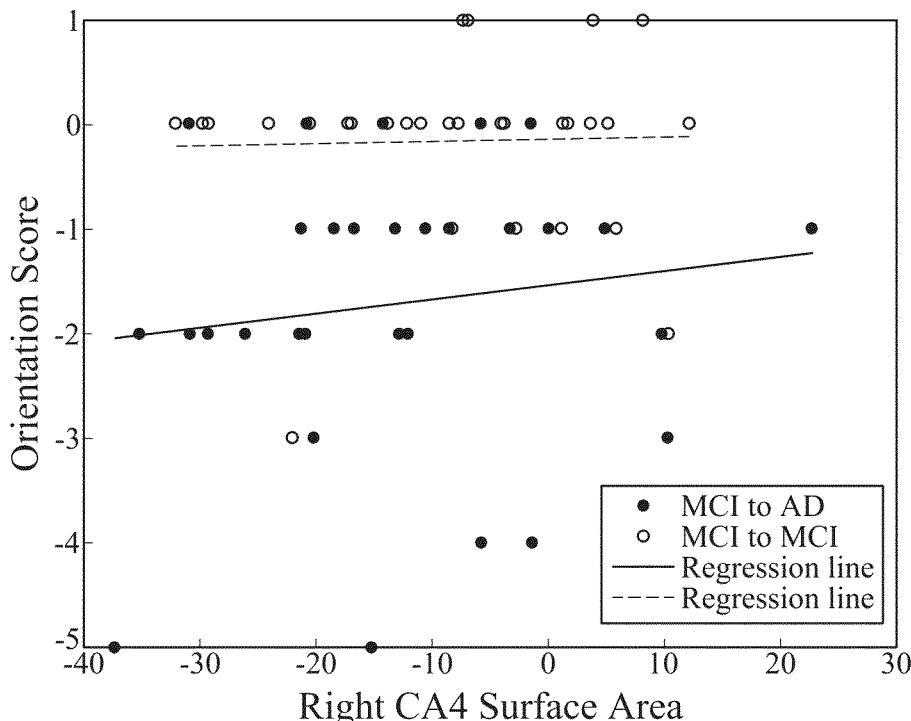
Figure 9G:
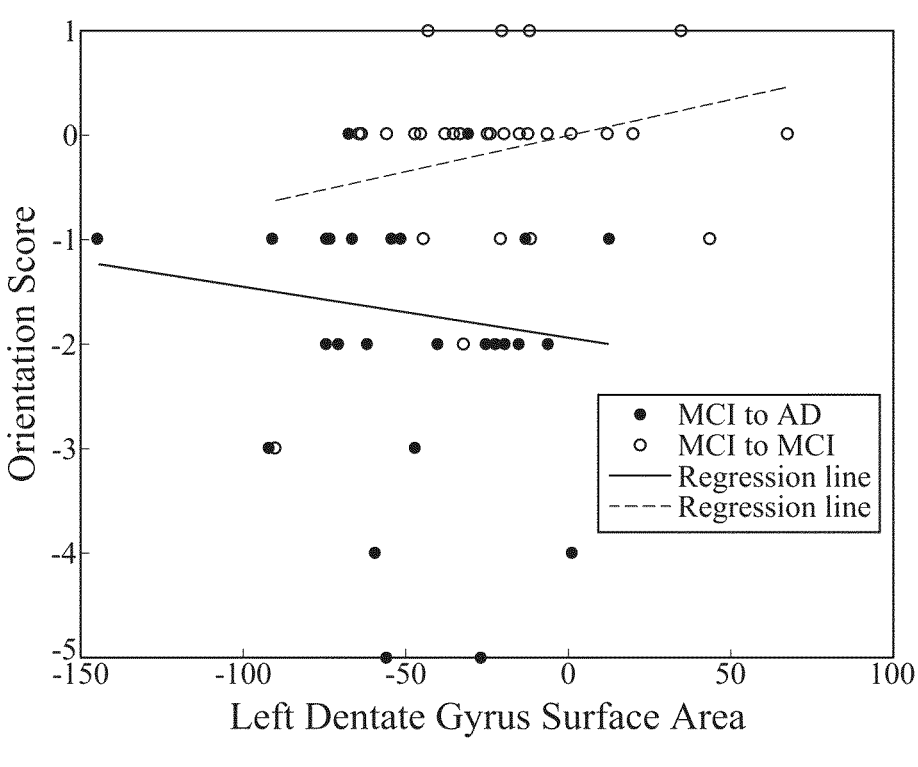
FIG. 9G is an exemplary scatterplot of hippocampal sub-regions' surface area vs. orientation in accordance with some embodiments of the present invention.
Figure 9G:
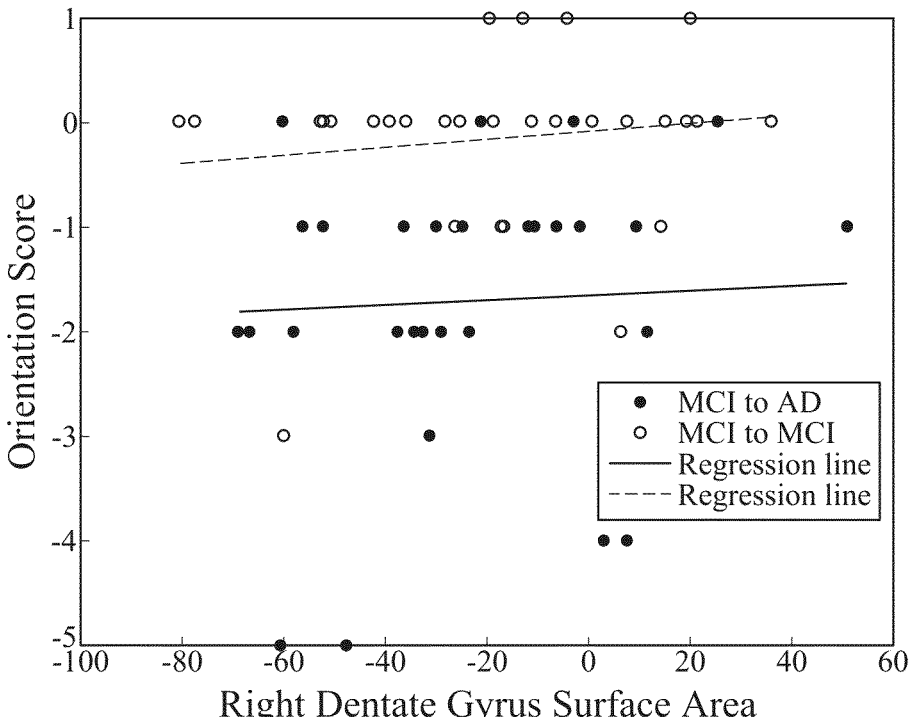
Figure 9H:
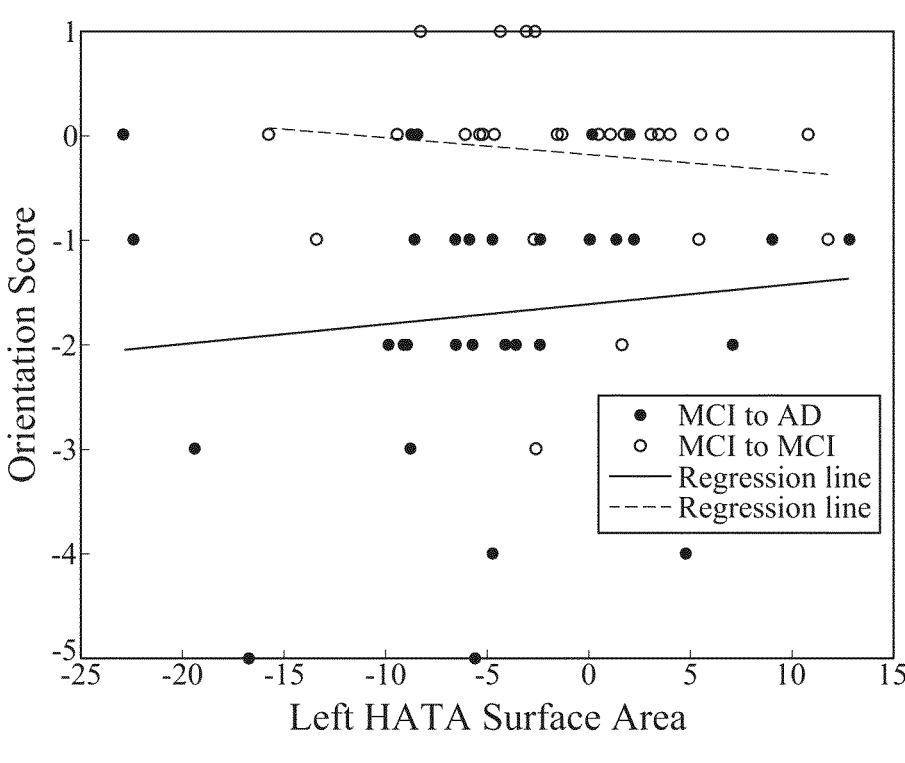
FIG. 9H is an exemplary scatterplot of hippocampal sub-regions' surface area vs. orientation in accordance with some embodiments of the present invention.
Figure 9H:
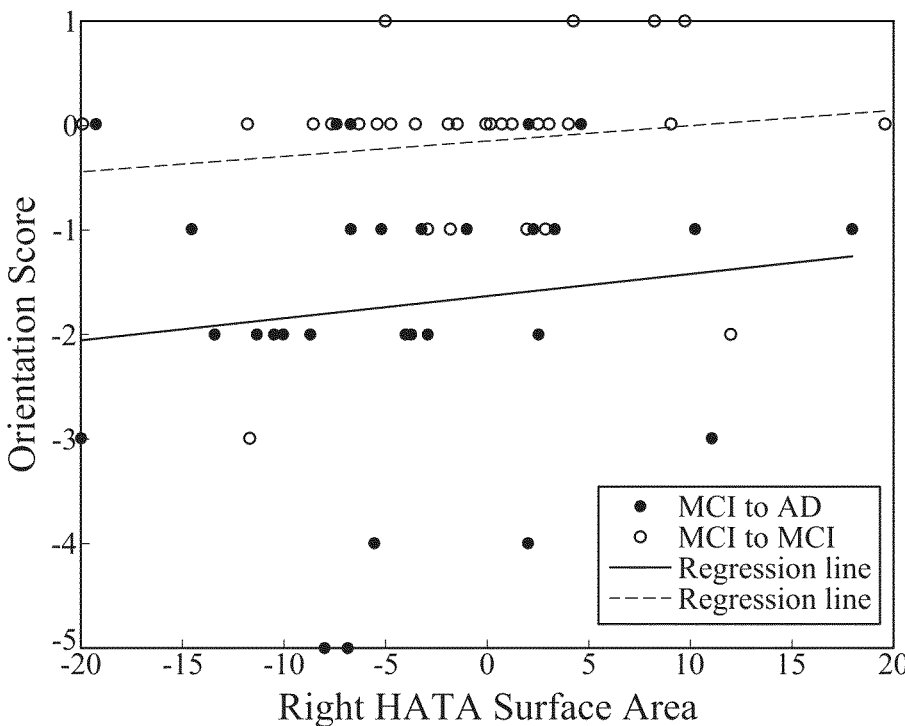
Figure 9I:
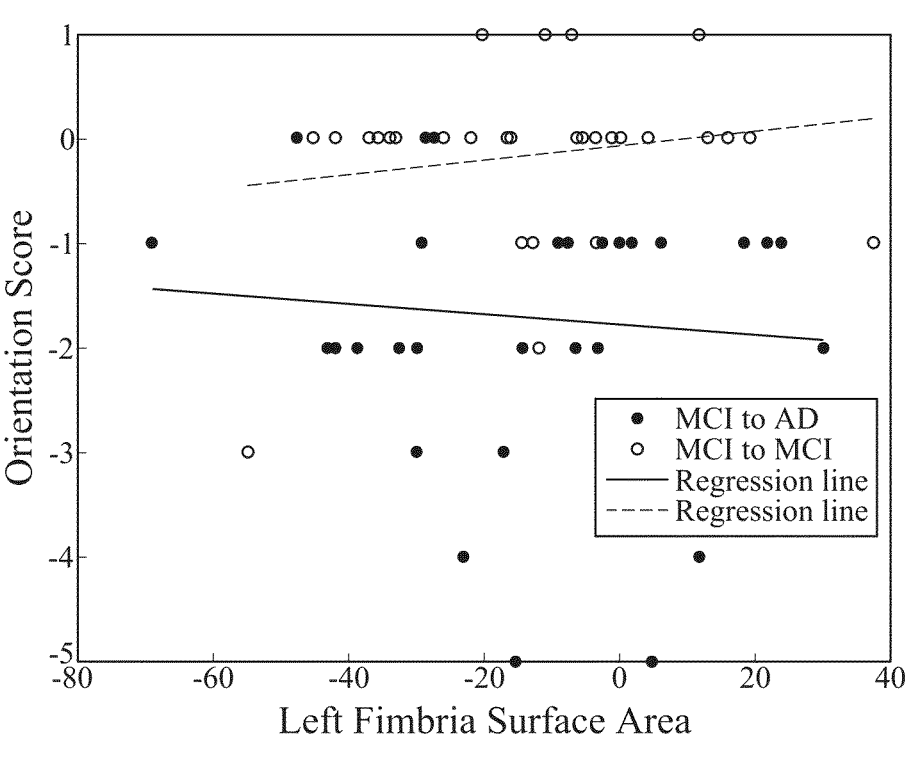
FIG. 9I is an exemplary scatterplot of hippocampal sub-regions' surface area vs. orientation in accordance with some embodiments of the present invention.
Figure 9I:
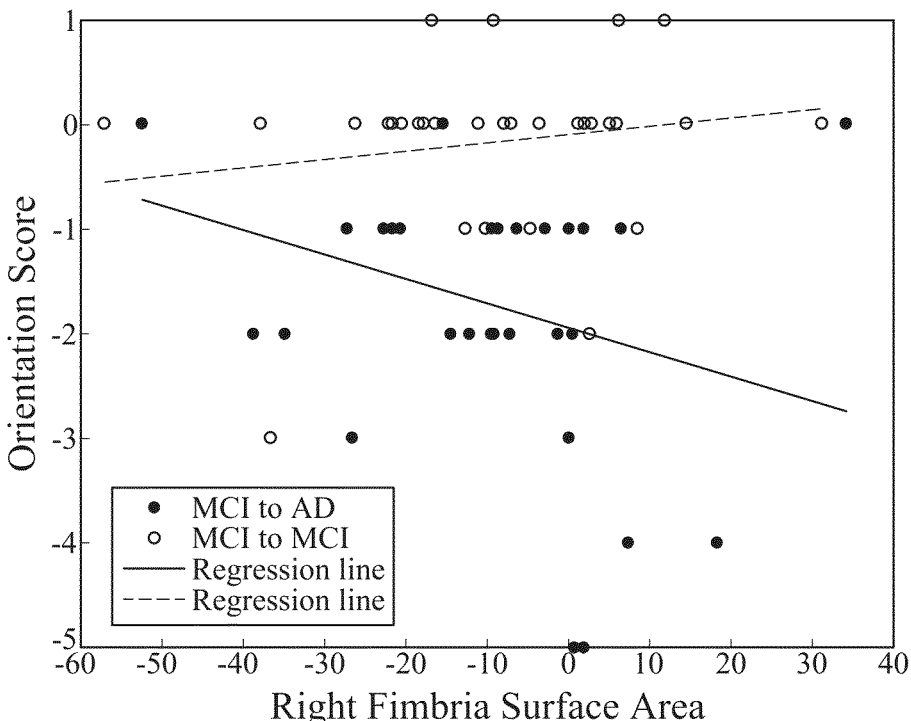
Figure 9J:
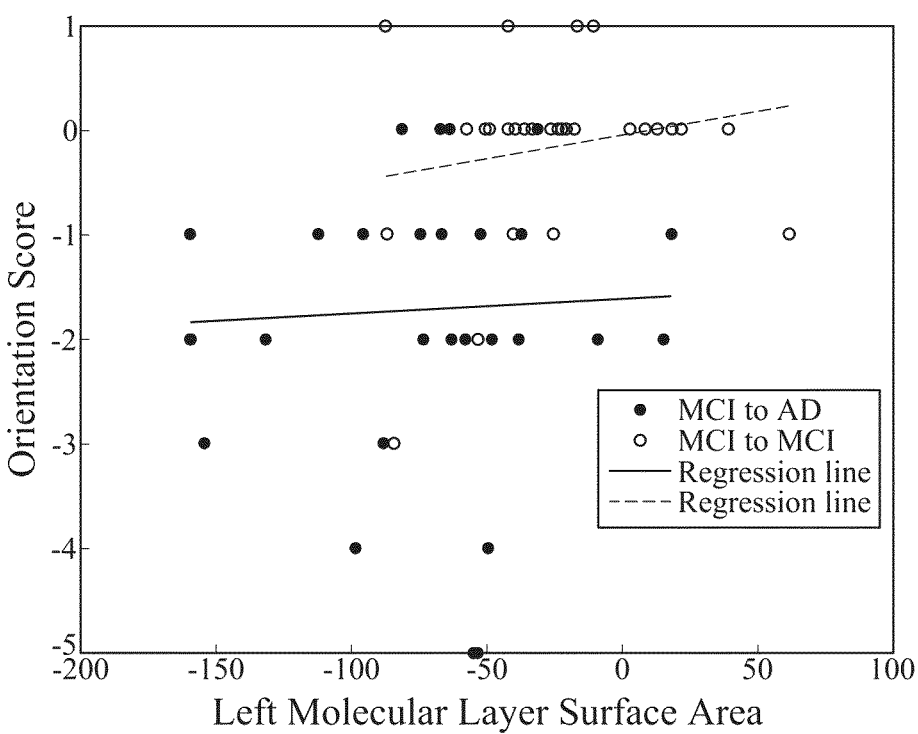
FIG. 9J is an exemplary scatterplot of hippocampal sub-regions' surface area vs. orientation in accordance with some embodiments of the present invention.
Figure 9J:
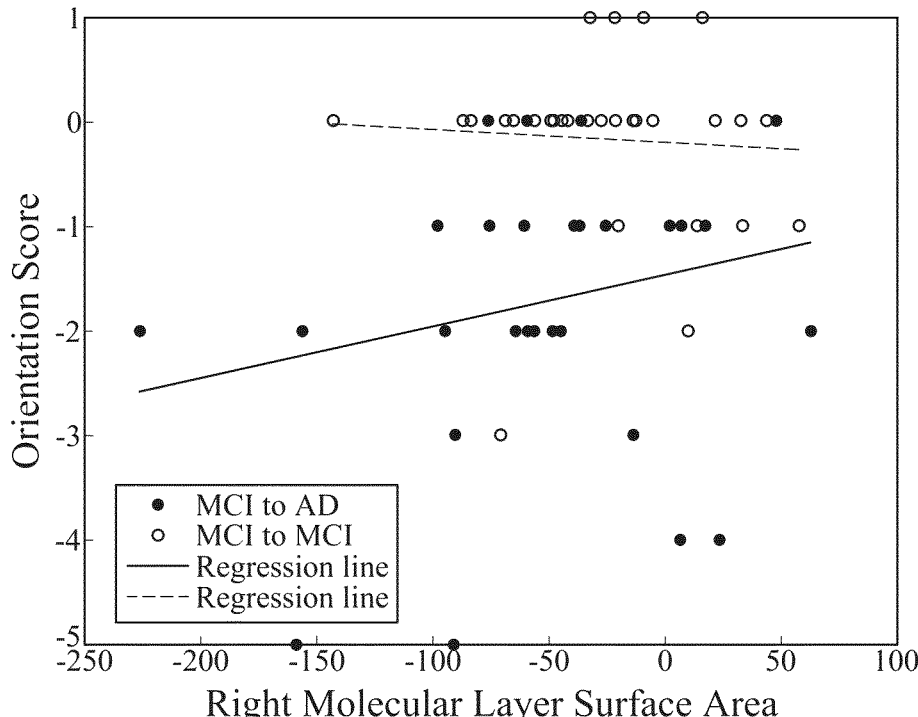
Figure 9K:
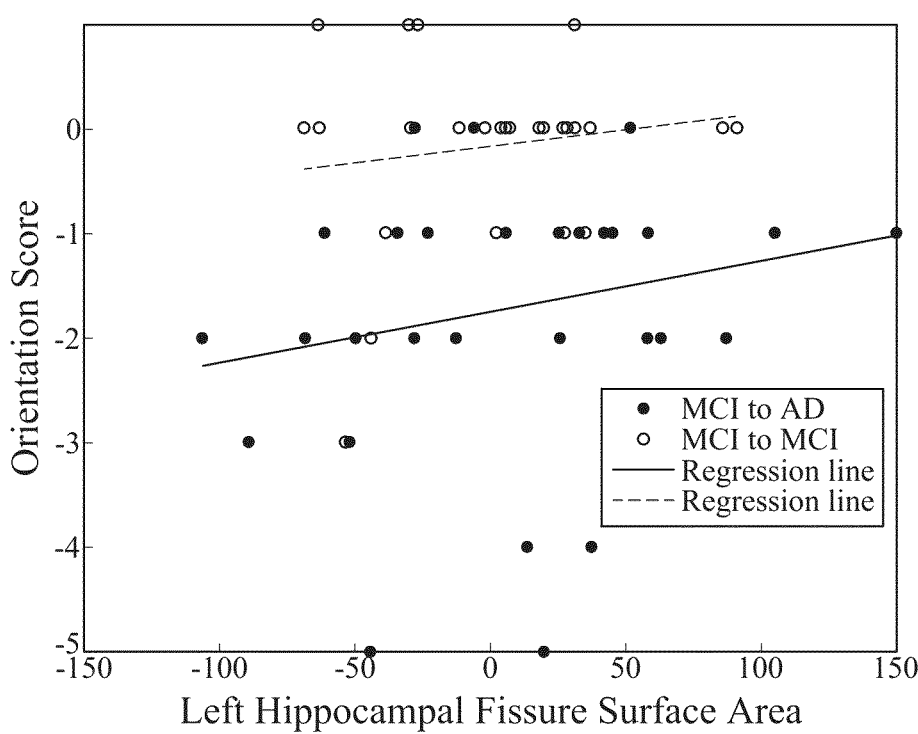
FIG. 9K is an exemplary scatterplot of hippocampal sub-regions' surface area vs. orientation in accordance with some embodiments of the present invention.
Figure 9K:
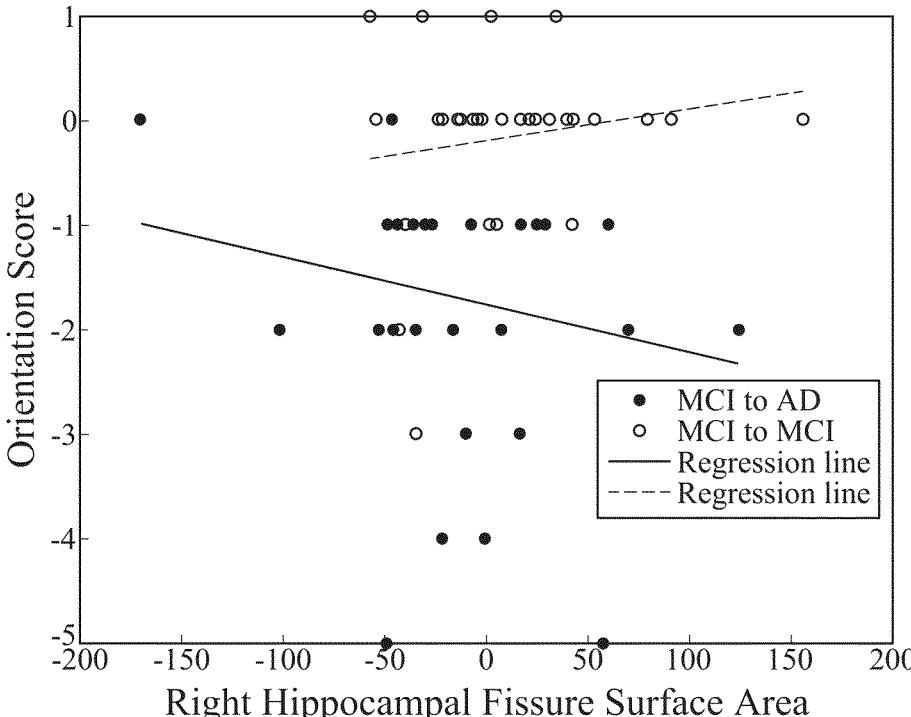
Figure 9L:
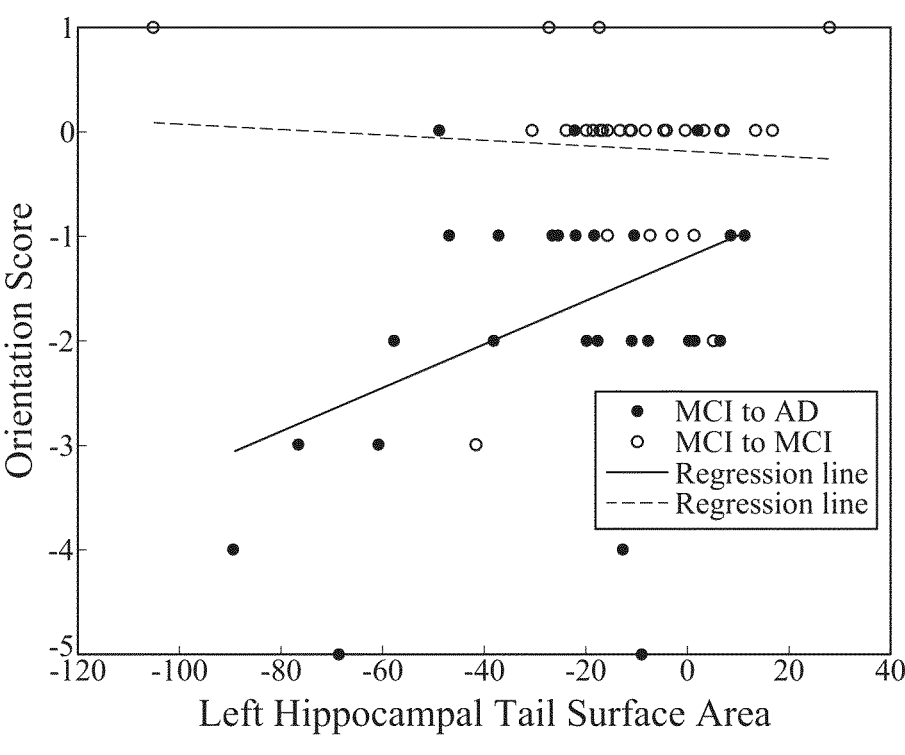
FIG. 9L is an exemplary scatterplot of hippocampal sub-regions' surface area vs. orientation in accordance with some embodiments of the present invention.
Figure 9L:
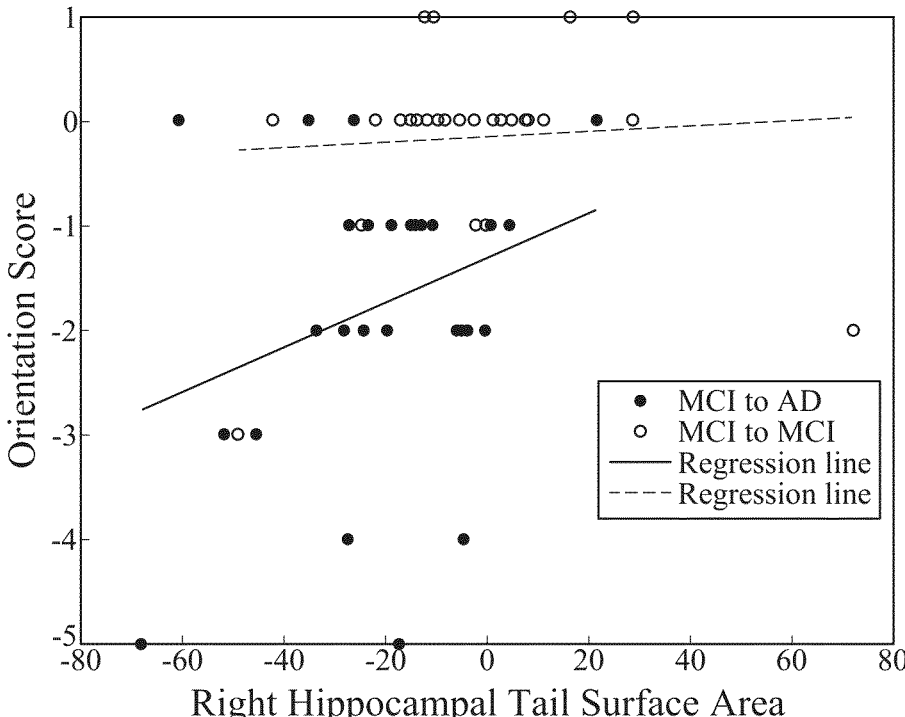

The curvature defined a point P on a closed surface S now includes the maximum curvature, the minimum curvature, and the ratio of principal curvatures which are calculated from equation (eq3), (eq4), and (eq6). FIG. 7 is an exemplary diagram illustrating meshes of a 3D model surface in accordance with some embodiments of the present invention. Please refer to FIG. 7, the 3D model surface of each sections of Hippocampus may be extended to a mesh map 701 as shown in FIG. 7. The mesh map 401 has grid points $V_1$, $V_2$, . . . , and $V_M$. In this embodiment, a maximum principal curvature of a sections of Hippocampus is defined as an average value of maximum principal curvatures of the grid points $V_1$, $V_2$, . . . , and $V_M$; a minimum principal curvature of a sections of Hippocampus is defined as an average value of minimum principal curvatures of the grid points $V_1$, $V_2$, . . . , and $V_M$; a ratio of principal curvatures of a sections of Hippocampus is defined as an average value of ratios of principal curvatures of the grid points $V_1$, $V_2$, . . . , and $V_M$.

For example, the ratio of principal curvatures of the grid points $V_1$, $V_2$, . . . , and $V_M$ are respectively $C_1$, $C_2$, . . . , and $C_N$, and the ratio of principal curvatures C of a section of the Hippocampus where the grid points $V_1$, $V_2$, . . . , and $V_N$ are located is:

$$Calct = \frac{C_1 + C_2 + \ldots + C_N}{M}$$

C is also referred to as average of a Ratio of Principal Curvature (RPC) for a section of the Hippocampus. In other words, in this embodiment, the ratio of principal curvatures C of a section of the Hippocampus is defined as an average of a Ratio of Principal Curvature (RPC) for the section of the Hippocampus.

Figure 5:
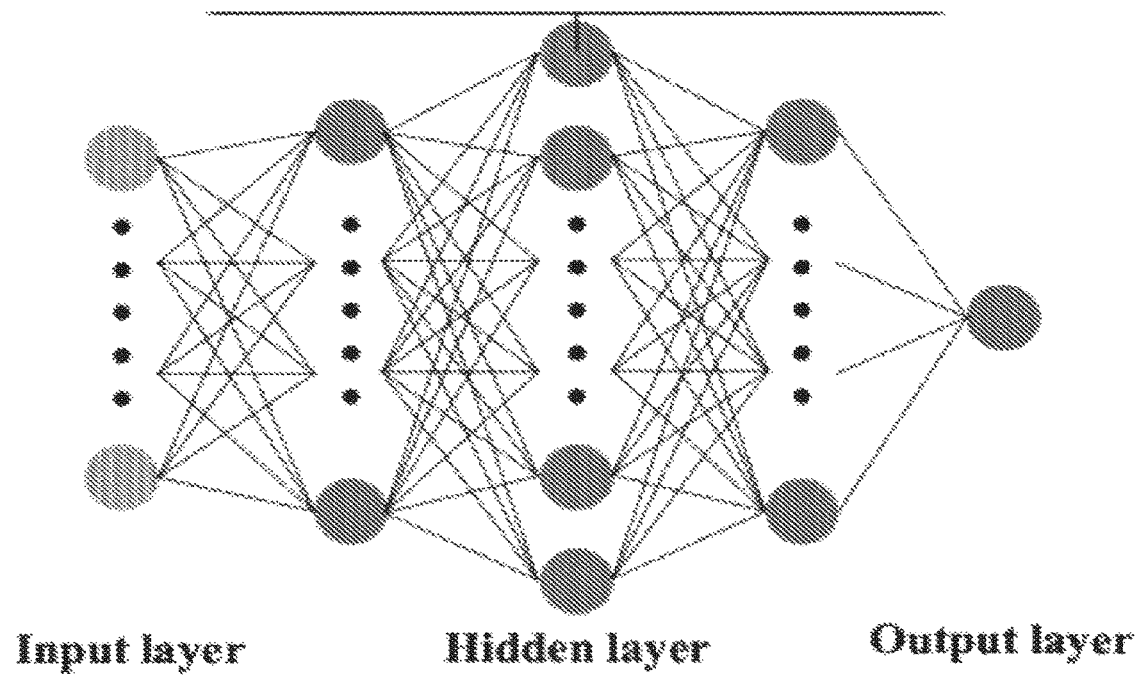
FIG. 5 is an exemplary diagram of an iterative neural network in accordance with an embodiment of the present invention.

With reference to FIG. 5, FIG. 5 is an exemplary diagram of an iterative neural network in accordance with an embodiment of the present invention. As describe in above, the volume, average of curvature for each section, and surface of the Hippocampus are obtained. These values are considered to be candidate parameters as inputs for the iterative neural network. As shown in FIG. 5, there're multiple input nodes, at least one output node and multiple layers of neuron nodes between the input and the output.

According to inventor's experiments, in an prefer embodiment, the values of Hippocampus volume, subiculum surface area, CA1 surface area, CA3 surface area, and the average RPCs of subiculum, CA1 and CA3 are selected to be the candidate parameters. In contrast, unlikely conventional studies only relied on the volume of the Hippocampus, the present invention uses curvatures to quantify the Hippocampus as features.

Besides neurological examinations, in order to enhance the accuracy of prediction, especially for predicting AD from MCI patients, the present invention further uses physical/cognitive function assessed using MMSE data to train the iterative neural network. The parameters both in MRI images and MMSE data can be used in a single machine learning model, or separately into two individual models. As a person skilled in the art will realize that for separating models, the results can be combined later using the majority voting.

The MMSE is a brief cognitive assessment tool commonly used to screen for dementia. The MMSE is one of the neuropsychological tests, which takes about 5 to 10 minutes. The MMSE is composed of 11 major items forming a 30-point questionnaire with five different domains of cognition analyses. The five domains are (1) Orientation, contributing a maximum of 10 points, (2) Registration, contributing a maximum of 3 points, (3) Attention and calculation, as a measure of working memory, contributing a maximum of 5 points, (4) Recall, contributing a maximum of 3 points, and (5) Language, contributing a maximum of 9 point. The 11 items are temporal orientation (5 points), spatial orientation (5 points), immediate memory (3 points), attention/ concentration (5 points), delayed recall (3 points), naming (2 points), verbal repetition (1 points), verbal comprehension (3 points), writing (1 points), reading a sentence (1 points), and constructional praxis (1 points). In general, the MMSE was administered and scored by a medical doctor certified in internal-medicine with extensive dementia experience.

Accordingly, the scores of MMSE data are used as candidate parameters for additional inputs. Based on inventor's experiment, orientation, attention, recall and language are the most effective features for accuracy.

Below three tables show the accuracy results of predicting AD with different inputs in iterative neural networks. In this embodiment, a basic Multilayer Perceptron (MLP) architecture is used with numerous of hidden layers. Table I uses only neuropsychological data (i.e., the MMSE score) as parameters. The accuracy is between 67.78% and 72.22%. Table II uses only neuroimaging features (i.e., the volume, surface area and RPC of the Hippocampus) as parameters. The accuracy is between 67.16% and 72.65%. Table III is combination of the neuropsychological data and neuroimaging feature data. The accuracy is between 75.12% and 75.86%.

TABLE I

| Input feature Basic MLP architecture | | | Neuropsychological data | | |
|---|---|---|---|---|---|
| | Neuro- | | 2 hidden layers with 4 neurons | | |
| Selection method | psycho-logical test | Number of Features | Accuracy | Sensitivity | Specificity |
| Univariate selection | MMSE | 4 | 72.22% | 70.37% | 74.07% |
| Feature importance | MMSE | 2 | 67.78% | 57.04% | 78.52% |

TABLE II

| Input feature Basic MLP architecture | | | Neuroimaging features | | |
|---|---|---|---|---|---|
| | | Number | 2 hidden layers with 12 neurons | | |
| Selection method | Criteria | of features | Accuracy | Sensitivity | Specificity |
| Univariate selection | p-value < 0.01 | 11 | 67.16% | 70.00% | 64.32% |
| Univariate selection | p-value < 0.05 | 19 | 71.17% | 69.38% | 72.96% |
| Univariate selection | p-value < 0.1 | 25 | 69.26% | 70.99% | 67.53% |
| Feature importance | Random forest Top 10 | 10 | 67.59% | 68.02% | 67.16% |
| Feature importance | Random forest Top 15 | 15 | 71.91% | 69.75% | 74.07% |
| Feature importance | Random forest Top 20 | 20 | 72.65% | 71.48% | 73.83% |
| Feature importance | Random forest Top 25 | 25 | 71.54% | 69.01% | 74.07% |

TABLE III

| Input feature Basic MLP architecture | | | | | |
|---|---|---|---|---|---|
| Criteria | Neuropsycho-logical test (Univariate selection | Number of feature | Neuroimaging + neuro-psychological data 2 hidden layers with 15 neurons | | |
| | | | Accuracy | Sensitivity | Specificity |
| Univariate selection method | | | | | |
| p-value < 0.05 | MMSE | 23 | 75.86% | 74.07% | 77.65% |
| p-value < 0.1 | MMSE | 29 | 73.95% | 72.10% | 75.80% |
| Feature importance method (Random forest classifier) | | | | | |
| Random forest Top 15 | MMSE | 19 | 75.12% | 76.05% | 74.20% |
| Random forest Top 20 | MMSE | 24 | 75.56% | 74.94% | 76.17% |

Next, we are going further through break down the MMSE total score into multiple MMSE sub-item scores, and also divide the entire hippocampus into several hippocampal sub-regions to find out the correlations between MMSE sub-item scores and hippocampal sub-regions, which is also the correlations between neuropsychological data and neuroimaging data. We expect to start from the MMSE sub-item scores to observe whether it is possible to map to the sub-regions of the hippocampus more precisely to assist medical doctors in diagnosing the status of patients at the early stage of Alzheimer's disease.

The original ADNI database was cleaned and pre-processed by Dr. Ke-Wei, Chen (Neuroimaging, Banner Alzheimer's Institute). The database can be mainly divided into three different types of data, which are subject's demographic data, neuropsychological data, and neuroimaging data, respectively. The Alzheimer's disease database provided by Dr. Chen contained 399 subjects including subject's demographic data, such as subject's age, gender, education level and so forth. Each subject would have twice diagnostic records during 2010 and 2012, which contained database from ADNI-1, ADNI-GO, and ADNI-2 three studies. Each diagnostic record separately contained the total scores of several different neuropsychological tests, e.g., MMSE (Mini-Mental State Examination), CDR (Clinical Dementia Rating), ADAS (Alzheimer's Disease Assessment Scale), and brain neuroimaging data like structural MRI (Magnetic Resonance Imaging) or FDG-PET (Fludeoxyglucose Positron Emission Tomography) images. In each diagnostic record, according to several medical doctor's evaluations of the neuropsychological data, neuroimaging data, and some other clinical situations, the diagnosis results of the subjects were classified into NL (Normal), MCI (Mild Cognitive Impairment), and AD (Alzheimer's Disease).

In the database provided by Dr. Chen, the subject diagnosed with MCI at the first time and then converted to AD at the second time during twice diagnostic records will be selected as the experimental group of experimental data. In addition, subjects diagnosed with MCI in both twice diagnostic records, which also called MCI non-converters, will be used as the control group of experimental data. The number of subjects in this experiment is listed in Table IV.

TABLE IV

| MCI converted to AD | MCI non-converter | Total |
|---|---|---|
| 31 | 31 | 62 |

31 subjects diagnosed with MCI then converted to AD were selected as the experimental group, and 31 MCI non-converters were used as the control group. Statistics on age, gender, and years of education of experimental data can be found in Table V. The average age of the subjects is over 65 years old, which is consistent with the past statistics. The average years of education are about 16 years, which is equivalent to general college graduates.

TABLE V

| | MCI converted to AD | MCI non-converter |
|---|---|---|
| No. of subjects | 31 | 31 |
| Age | 72.0 ± 7.8 | 76.7 ± 8.1 |
| Years of education | 16.4 ± 2.7 | 15.1 ± 2.9 |
| Gender (M/F) | 17/14 | 22/9 | where X±Y, X is the mean, and Y is the standard deviation.

The experimental data mainly divide into two groups, one is MCI converted to AD group, and the other is MCI non-converter group. Each group contains 31 subjects. The mean and standard deviation of the MMSE sub-item score for each group are listed in Table VI. We use p-value to determine whether the two sets of data have statistical significance with significance level $\alpha=5\%$. Reported significances (p-value) are two-tailed.

TABLE VI

| Visit | MMSE score | MCI converted to AD | MCI non-converter | p-value |
|---|---|---|---|---|
| 1 | Orientation (10) | 9.19 ± 0.95 | 9.74 ± 0.58 | 0.0077 |
| | Registration (3) | 3.00 ± 0.00 | 3.00 ± 0.00 | N/A |
| | Attention & Calculation (5) | 4.61 ± 0.84 | 4.71 ± 0.86 | 0.66 |
| | Recall (3) | 1.87 ± 1.02 | 2.03 ± 1.08 | 0.55 |
| | Language (9) | 8.55 ± 0.51 | 8.52 ± 0.63 | 0.82 |
| | Total (30) | 27.23 ± 1.50 | 28.0 ± 1.63 | 0.057 |
| 2 | Orientation (10) | 7.48 ± 1.46 | 9.58 ± 0.72 | $1.23 \times 10^{-9}$ |
| | Registration (3) | 2.97 ± 0.18 | 2.94 ± 0.25 | 0.56 |
| | Attention & Calculation (5) | 4.10 ± 1.49 | 4.84 ± 0.58 | 0.012 |
| | Recall (3) | 0.94 ± 1.09 | 1.74 ± 1.32 | 0.011 |
| | Language (9) | 8.39 ± 0.99 | 8.71 ± 0.64 | 0.13 |
| | Total (30) | 23.87 ± 3.51 | 27.81 ± 2.09 | $1.37 \times 10^{-6}$ | where X±Y, X is the mean, and Y is the standard deviation.

The experimental data at the first time of two groups are both the subjects diagnosed with MCI. It is inferred that the two sets of data have high similarity and small difference. Therefore, the p-value should be greater than 0.05. Among them, the difference of the mean in the orientation sub-item score is the largest, which makes the p-value less than 0.05 (0.0077) and can be inferred to have statistical significance, which is also reflected in the mean and the p-value of the total score. The difference of the mean of the total score is mainly from the difference of the mean of the orientation sub-item score.

The experimental data at the second time of two groups are subjects diagnosed with AD and MCI respectively. It is inferred that the two sets of data with lower similarity and larger difference. Their p-value should be less than 0.05. The p-values of the MMSE sub-item score registration and language are greater than 0.05, which means that although the diagnosis results of the two groups are different, it is not directly shown on these two sub-item scores. Or the magnitude of the difference is not obvious enough to have statistical significance. The p-values of the other three sub-items orientation, attention and calculation, and recall are all less than 0.05, which is the same as the initial inference. The sub-item score orientation has the most obvious statistical significance due to the lowest p-value, which can also be observed from the difference of mean between two groups.

The image pre-processing tools used is FreeSurfer, which is a suite of software tools for studying the cortical and subcortical anatomy as mentioned above. The original structural MRI image through the surface-based stream pipeline of FreeSurfer can calculate the local curvature and surface area, and the volume-based stream pipeline can label the volume and create a mask of the brain. After the pre-processing process, the hippocampal sub-regions of hippocampus in the brain can be segmented. A total number of 12 hippocampal sub-regions are used in the experiment. Their abbreviations and full names are shown in Table VII. Each sub-region would contain the following variables: surface area, volume, maximum curvature, minimum curvature, and the average ratio of principal curvature.

TABLE VII

| Abbr. | Full Name |
| --- | --- |
| PaS | Parasubiculum |
| PrS | Presubiculum |
| S | Subiculum |
| CA1 | Cornu Ammonis 1 |
| CA3 | Cornu Ammonis 3 |
| CA4 | Cornu Ammonis 4 |
| DG | Dentate Gyrus |
| HATA | Hippocampal Amygdala Transition Area |
| Fim. | Fimbria |
| ML | Molecular Layer |
| Fiss. | Hippocampal Fissure |
| Tail | Hippocampal Tail |

We would like to find out the correlations between the hippocampal sub-regions and MMSE sub-item scores, which is also the correlations between neuroimaging data and neuropsychological data. In terms of neuroimaging data, we obtain several variables of the hippocampus sub-regions through the pre-processing process by FreeSurfer. In terms of neuropsychological data, the total score of MMSE are divided into five sub-item scores depend on the function of the test, which are orientation, registration, attention and calculation, recall, and language respectively. We choose to subtract the two diagnostic scores and take the difference, which means the change between the two diagnoses, as random variables in the neuropsychological data. The same method is also applied to the neuroimaging data.

The most useful graph for displaying the relationship between two quantitative variables is a scatterplot, which is also one of the seven basic tools of quality. A scatterplot shows the relationship between two quantitative variables measured on the same individuals. The values of one variable appear on the horizontal axis, and the values of the other variable appear on the vertical axis. Each individual in the data appears as the point in the plot fixed by the values of both variables for that individual. In this embodiment, the variables of the hippocampal sub-regions are explanatory variables x on the horizontal axis of a scatterplot. The MMSE sub-item scores are response variables y on the vertical axis of a scatterplot.

In order to determine whether the established regression equation and the corresponding independent variables are statistically significant, a hypothesis testing is needed. The procedure for performing any hypothesis testing can be set out in terms of seven steps: 1. Decide on a null hypothesis, $H_0$. $H_0$:$\rho$=0. This implies that there is no correlation between the variables in the population. 2. Decide on an alternative hypothesis, $H_1$. $H_1\rho\approx0$. This implies that there is a correlation in the population, including positive or negative correlation. 3. Decide on a significance level $\alpha$: 5% significance level $\alpha$. 4. Calculate the appropriate test statistic, using the sample data. The calculated test statistic is $$Calct = r\sqrt{\frac{n-2}{1-r^2}}.$$

Notice that this formula contains n, the number of individuals as well as r. 5. Find from tables the appropriate tabulated test statistic. Find Tab t from Table VIII, for $\alpha$=0.05, two-sided $H_1$, and v=n−2, for this formula and these data, respectively. (The number of degrees of freedom, namely n−2 occurs in the formula for Calc t) 6. Compare the calculated and tabulated test statistics, and decide whether to reject the null hypothesis, $H_0$. 7. State a conclusion, after checking to see whether the assumptions required for the test in question are valid.

TABLE VIII

| v | 0.1000 | 0.0500 | 0.0250 | 0.0100 | 0.0050 | 0.0010 | 0.0005 |
| --- | --- | --- | --- | --- | --- | --- | --- |
| 1 | 3.078 | 6.314 | 12.706 | 31.821 | 63.657 | 318.309 | 636.619 |
| 2 | 1.886 | 2.920 | 4.303 | 6.965 | 9.925 | 22.327 | 31.599 |
| 3 | 1.638 | 2.353 | 3.182 | 4.541 | 5.841 | 10.215 | 12.924 |
| 4 | 1.533 | 2.132 | 2.776 | 3.747 | 4.604 | 7.173 | 8.610 |
| 5 | 1.476 | 2.015 | 2.571 | 3.365 | 4.032 | 5.893 | 6.869 |
| 6 | 1.440 | 1.943 | 2.447 | 3.143 | 3.707 | 5.208 | 5.959 |
| 7 | 1.415 | 1.895 | 2.365 | 2.998 | 3.499 | 4.785 | 5.408 |
| 8 | 1.397 | 1.860 | 2.306 | 2.896 | 3.355 | 4.501 | 5.041 |
| 9 | 1.383 | 1.833 | 2.262 | 2.821 | 3.250 | 4.297 | 4.781 |
| 10 | 1.372 | 1.812 | 2.228 | 2.764 | 3.169 | 4.144 | 4.587 |
| 11 | 1.363 | 1.796 | 2.201 | 2.718 | 3.106 | 4.025 | 4.437 |
| 12 | 1.356 | 1.782 | 2.179 | 2.681 | 3.055 | 3.930 | 4.318 |
| 13 | 1.350 | 1.771 | 2.160 | 2.650 | 3.012 | 3.852 | 4.221 |
| 14 | 1.345 | 1.761 | 2.145 | 2.624 | 2.977 | 3.787 | 4.140 |
| 15 | 1.341 | 1.753 | 2.131 | 2.602 | 2.947 | 3.733 | 4.073 |
| 16 | 1.337 | 1.746 | 2.120 | 2.583 | 2.921 | 3.686 | 4.015 |
| 17 | 1.333 | 1.740 | 2.110 | 2.567 | 2.898 | 3.646 | 3.965 |
| 18 | 1.330 | 1.734 | 2.101 | 2.552 | 2.878 | 3.610 | 3.922 |
| 19 | 1.328 | 1.729 | 2.093 | 2.539 | 2.861 | 3.579 | 3.883 |
| 20 | 1.325 | 1.725 | 2.086 | 2.528 | 2.845 | 3.552 | 3.850 |
| 21 | 1.323 | 1.721 | 2.080 | 2.518 | 2.831 | 3.527 | 3.819 |
| 22 | 1.321 | 1.717 | 2.074 | 2.508 | 2.819 | 3.505 | 3.792 |
| 23 | 1.319 | 1.714 | 2.069 | 2.500 | 2.807 | 3.485 | 3.768 |
| 24 | 1.318 | 1.711 | 2.064 | 2.492 | 2.797 | 3.467 | 3.745 |
| 25 | 1.316 | 1.708 | 2.060 | 2.485 | 2.787 | 3.450 | 3.725 |
| 26 | 1.315 | 1.706 | 2.056 | 2.479 | 2.779 | 3.435 | 3.707 |
| 27 | 1.314 | 1.703 | 2.052 | 2.473 | 2.771 | 3.421 | 3.690 |
| 28 | 1.313 | 1.701 | 2.048 | 2.467 | 2.763 | 3.408 | 3.674 |

TABLE VIII-continued

| v | 0.1000 | 0.0500 | 0.0250 | 0.0100 | 0.0050 | 0.0010 | 0.0005 |
|---|--------|--------|--------|--------|--------|--------|--------|
| 29 | 1.311 | 1.699 | 2.045 | 2.462 | 2.756 | 3.396 | 3.659 |
| 30 | 1.310 | 1.697 | 2.042 | 2.457 | 2.750 | 3.385 | 3.646 |
| 40 | 1.303 | 1.684 | 2.021 | 2.423 | 2.704 | 3.307 | 3.551 |
| 50 | 1.299 | 1.676 | 2.009 | 2.403 | 2.678 | 3.261 | 3.496 |
| 60 | 1.296 | 1.671 | 2.000 | 2.390 | 2.660 | 3.232 | 3.460 |
| 100 | 1.290 | 1.660 | 1.984 | 2.364 | 2.626 | 3.174 | 3.390 |
| 120 | 1.289 | 1.658 | 1.980 | 2.358 | 2.617 | 3.160 | 3.373 |
| ∞ | 1.282 | 1.645 | 1.960 | 2.326 | 2.576 | 3.090 | 3.291 |

Source: Retrieved Oct. 23, 2018, from https://home.ubalt.edu/ntsbarsh/Business-stat/StatistialTables.pdf The table shows the critical t-values for a given a level (one-tailed) and degrees of freedom. The degrees of freedom are the rows (denoted by v). Note: The probability levels represent the whole of $\alpha$ (you must divide $\alpha$ by 2 if you want the t-value for a two-tailed test).

There is a slightly shorter way of testing the null hypothesis if the population correlation coefficient is zero. Steps 1, 2, and 3 are the same as above; here are the other steps: 4. The calculated test statistic is simply $$Calcr: r = \frac{1}{n-1}\sum_{i=1}^{n}\left(\frac{x_i - \bar{x}}{s_x}\right)\left(\frac{y_i - \bar{y}}{s_y}\right), 5.$$

The tabulated test statistic is obtained from Table IX, Critical values of Pearson's r. 6. Compare the calculated and tabulated test statistics, and decide whether to reject the null hypothesis, $H_0$. 7. State a conclusion, after checking to see whether the assumptions required for the test in question are valid.

TABLE IX

| | One-tailed | | |
|---|---|---|---|
| | 0.05 | 0.025 | 0.005 |
| | Two-tailed (Degrees of freedom v = n − 2) | | |
| v | 0.1 | 0.05 | 0.01 |
| 1 | 0.988 | 0.997 | 0.999 |
| 2 | 0.900 | 0.950 | 0.990 |
| 3 | 0.805 | 0.878 | 0.959 |
| 4 | 0.729 | 0.811 | 0.917 |
| 5 | 0.669 | 0.754 | 0.875 |
| 6 | 0.621 | 0.707 | 0.834 |
| 7 | 0.584 | 0.666 | 0.798 |
| 8 | 0.549 | 0.632 | 0.765 |
| 9 | 0.521 | 0.602 | 0.735 |
| 10 | 0.497 | 0.576 | 0.708 |
| 11 | 0.476 | 0.553 | 0.684 |
| 12 | 0.458 | 0.532 | 0.661 |
| 13 | 0.441 | 0.514 | 0.641 |
| 14 | 0.426 | 0.497 | 0.623 |
| 15 | 0.412 | 0.482 | 0.606 |
| 16 | 0.400 | 0.468 | 0.590 |
| 17 | 0.389 | 0.456 | 0.575 |
| 18 | 0.378 | 0.444 | 0.561 |
| 19 | 0.369 | 0.433 | 0.549 |
| 20 | 0.360 | 0.423 | 0.537 |
| 21 | 0.352 | 0.413 | 0.526 |
| 22 | 0.344 | 0.404 | 0.515 |
| 23 | 0.337 | 0.396 | 0.505 |
| 24 | 0.330 | 0.388 | 0.496 |
| 25 | 0.323 | 0.381 | 0.487 |
| 26 | 0.317 | 0.374 | 0.479 |
| 27 | 0.311 | 0.367 | 0.471 |

TABLE IX-continued

| 28 | 0.306 | 0.361 | 0.463 |
|---|---|---|---|
| 29 | 0.301 | 0.355 | 0.456 |
| 30 | 0.296 | 0.349 | 0.449 |
| 40 | 0.257 | 0.304 | 0.393 |
| 50 | 0.231 | 0.273 | 0.354 |
| 60 | 0.211 | 0.250 | 0.325 |
| 100 | 0.164 | 0.195 | 0.254 |

Source: Retrieved Oct. 23, 2018, from https://www.statisticssolutions.com/table-of-critical-values-pearson-correlation/

As mentioned above, the original structural MRI image through the surface-based stream pipeline of FreeSurfer can calculate the local curvature and surface area, and the volume-based stream pipeline can label the volume and create a mask of the brain. After the pre-processing process, the hippocampal sub-regions of hippocampus in the brain can be segmented. A total number of 12 hippocampal sub-regions are used in the experiment. Each sub-region would contain the following variables: surface area, volume, maximum curvature, minimum curvature, and the average ratio of principal curvature.

FIG. 8A to FIG. 8L are exemplary scatterplots of hippocampal sub-regions' volume vs. orientation in accordance with some embodiments of the present invention. Please refer to FIG. 8A to FIG. 8L, scatterplots of several hippocampal sub-regions' volume vs. orientation are shown in FIG. 8A to FIG. 8L, including both left and right side of hippocampus. In FIG. 8A to FIG. 8L, the black dot represents the data point which the subject diagnosed with MCI then converted to AD, and the white dot represents subject diagnosed with MCI in both twice diagnostic records. The corresponding solid line and dashed line are the least-squares regression line of two groups respectively, which are drawn according to the scattered points.

31 subjects diagnosed with MCI then converted to AD were selected as the experimental group, and 31 MCI non-converters were used as the control group. Due to the lack of data points, it is not easy to observe the relationship between hippocampal sub-regions' volume and orientation score via scatterplot. Therefore, the following analysis is mainly based on the characteristics of the least-squares regression line.

Here, we mainly use the two characteristics of the least-squares regression line for analysis: 1. Observe the sign of the slope of the least-squares regression line to see if there is a positive association, negative association, or no association between the two data. 2. Observe the magnitude of the slope to determine the strength of the relationship between the two data.

According to the above description, we can find that the volume of hippocampal sub-region parasubiculum, presubiculum, and subiculum have a positive association with orientation. In addition, in terms of the magnitude of the slope, its value is larger than that of other sub-regions. This phenomenon is more obvious on the left side of the hippocampus than on the right side.

FIG. 9A to FIG. 9L are exemplary scatterplots of hippocampal sub-regions' surface area vs. orientation in accordance with some embodiments of the present invention. Please refer to FIG. 9A to FIG. 9L, scatterplots of several hippocampal sub-regions' surface area vs. orientation are shown in FIG. 9A to FIG. 9L, including both left and right side of hippocampus.

We can also find that the surface area of hippocampal sub-region parasubiculum, presubiculum, and subiculum have a positive association with orientation. And similar associations were observed in the volume and surface area of the hippocampal sub-regions.

Next, we will use hypothesis testing which is a more systematic way to summarize the experimental results.

In the hypothesis testing described above, we calculate the Pearson's r, t-statistic, and p-value of the two data, and compared with the tabulated value to determine whether to reject the null hypothesis ($H_0$) and have statistical significance. The parameters of hypothesis testing are shown in Table X.

TABLE X

| Null Hypothesis $H_0$ | $H_0$: $\rho = 0$ |
| Alternative Hypothesis $H_1$ | $H_1$: $\rho \neq 0$ |

TABLE X-continued

| Significance Level $\alpha$ | 5% |
| Number of Individuals n | 31 |
| Degrees of Freedom v | 29 |
| Tabulated t-statistic | 2.045 (Table VIII) |
| Tabulated Pearson's r | 0.355 (Table IX) |

The Pearson's r, t-statistic, and p-value between hippocampal sub-regions and MMSE sub-item scores are shown in Table XI to XV. Compared the calculated and tabulated test statistics, and mark the value as red if the experimental result rejects the null hypothesis.

TABLE XI

| Sub-region | | MCI converted to AD (Surface Area) (Left Side) | | | | | |
| --- | --- | --- | --- | --- | --- | --- | --- |
| | | Pas | PrS | S | CA1 | CA3 | CA4 |
| Orientation | r | 0.1268 | 0.3858 | 0.3324 | 0.1530 | 0.0503 | 0.1033 |
| | t | 0.6884 | 2.2520 | 1.8980 | 0.8339 | 0.2711 | 0.5595 |
| | p | 0.4967 | 0.0321 | 0.0677 | 0.4111 | 0.7882 | 0.5801 |
| Registration | r | −0.0449 | −0.1368 | −0.1267 | −0.1340 | −0.2501 | −0.2665 |
| | t | 0.2420 | 0.7437 | 0.6879 | 0.7283 | 1.3908 | 1.4888 |
| | p | 0.8105 | 0.4631 | 0.4970 | 0.4723 | 0.1749 | 0.1473 |
| Attention | r | 0.0676 | 0.2843 | 0.4149 | 0.2943 | −0.0418 | 0.1560 |
| | t | 0.3646 | 1.5972 | 2.4553 | 1.6580 | 0.2255 | 0.8504 |
| | p | 0.7180 | 0.1211 | 0.0203 | 0.1081 | 0.8232 | 0.4021 |
| Recall | r | 0.0176 | 0.1600 | 0.1522 | 0.0375 | 0.3781 | 0.2883 |
| | t | 0.0951 | 0.8728 | 0.8294 | 0.2019 | 2.1994 | 1.6215 |
| | p | 0.9249 | 0.3899 | 0.4137 | 0.8414 | 0.0360 | 0.1157 |
| Language | r | 0.0248 | 0.2790 | 0.3026 | 0.0589 | 0.0739 | 0.1250 |
| | t | 0.1338 | 1.5644 | 1.7095 | 0.3179 | 0.3988 | 0.6782 |
| | p | 0.8945 | 0.1286 | 0.0980 | 0.7529 | 0.6929 | 0.5030 |
| Sub-region | | DG | HATA | Fimbria | ML | Fissure | Tail |
| Orientation | r | 0.0088 | 0.1025 | 0.0014 | 0.1591 | 0.2683 | 0.4316 |
| | t | 0.0474 | 0.5551 | 0.0076 | 0.8677 | 1.5001 | 2.5766 |
| | p | 0.9626 | 0.5831 | 0.9940 | 0.3927 | 0.1444 | 0.0153 |
| Registration | r | −0.3554 | −0.1435 | −0.1350 | −0.0821 | −0.4378 | −0.0955 |
| | t | 2.0478 | 0.7807 | 0.7338 | 0.4436 | 2.6222 | 0.5167 |
| | p | 0.0497 | 0.4413 | 0.4690 | 0.6606 | 0.0138 | 0.6093 |
| Attention | r | 0.0986 | −0.1941 | −0.2416 | 0.1731 | 0.0984 | 0.5816 |
| | t | 0.5336 | 1.0653 | 1.3409 | 0.9465 | 0.5326 | 3.8504 |
| | p | 0.5977 | 0.2955 | 0.1904 | 0.3517 | 0.5983 | 0.0006 |
| Recall | r | 0.1930 | 0.2535 | 0.4303 | 0.2858 | 0.0889 | −0.0445 |
| | t | 1.0591 | 1.4113 | 2.5672 | 1.6061 | 0.4808 | 0.2401 |
| | p | 0.2983 | 0.1688 | 0.0157 | 0.1191 | 0.6343 | 0.8119 |
| Language | r | 0.0306 | −0.1774 | −0.0133 | 0.2107 | −0.0263 | 0.2672 |
| | t | 0.1650 | 0.9707 | 0.0714 | 1.1607 | 0.1416 | 1.4933 |
| | p | 0.8701 | 0.3397 | 0.9436 | 0.2552 | 0.8884 | 0.1462 |
| Sub-region | | MCI converted to AD (Surface Area) (Right Side) | | | | | |
| | | PaS | PrS | S | CA1 | CA3 | CA4 |
| Orientation | r | 0.0428 | 0.3494 | 0.3798 | 0.1976 | 0.1533 | 0.1943 |
| | t | 0.2305 | 2.0084 | 2.2112 | 1.0855 | 0.8357 | 1.0666 |
| | p | 0.8193 | 0.0540 | 0.0351 | 0.2866 | 0.4102 | 0.2950 |
| Registration | r | 0.0078 | −0.1730 | −0.1403 | −0.2922 | −0.4000 | −0.0332 |
| | t | 0.0423 | 0.9457 | 0.7629 | 1.6451 | 2.3500 | 0.1787 |
| | p | 0.9666 | 0.3521 | 0.4517 | 0.1107 | 0.0258 | 0.8594 |
| Attention | r | 0.1277 | 0.2009 | 0.0272 | 0.1037 | 0.1003 | 0.1116 |
| | t | 0.6936 | 1.1044 | 0.1464 | 0.5613 | 0.5431 | 0.6050 |
| | p | 0.4935 | 0.2785 | 0.8846 | 0.5789 | 0.5912 | 0.5499 |
| Recall | r | −0.0756 | −0.0356 | 0.0152 | −0.0136 | −0.0976 | −0.0520 |
| | t | 0.4084 | 0.1919 | 0.0821 | 0.0731 | 0.5282 | 0.2802 |
| | p | 0.6859 | 0.8492 | 0.9351 | 0.9423 | 0.6014 | 0.7813 |
| Language | r | 0.1366 | 0.1253 | 0.0540 | −0.0960 | −0.2181 | 0.0555 |
| | t | 0.7425 | 0.6800 | 0.2910 | 0.5195 | 1.2033 | 0.2992 |
| | p | 0.4637 | 0.5019 | 0.7731 | 0.6074 | 0.2386 | 0.7669 |

TABLE XI-continued

| Sub-region | | DG | HATA | Fimbria | ML | Fissure | Tail |
|---|---|---|---|---|---|---|---|
| Orientation | r | 0.0802 | 0.1793 | 0.2222 | 0.2099 | −0.1084 | 0.3607 |
| | t | 0.4331 | 0.9812 | 1.2273 | 1.1558 | 0.5873 | 2.0826 |
| | p | 0.6682 | 0.3346 | 0.2296 | 0.2572 | 0.5615 | 0.0462 |
| Registration | r | −0.1392 | −0.2613 | 0.0341 | −0.0901 | −0.0920 | −0.0877 |
| | t | 0.7571 | 1.4577 | 0.1837 | 0.4873 | 0.4975 | 0.4739 |
| | p | 0.4551 | 0.1557 | 0.8556 | 0.6297 | 0.6226 | 0.6391 |
| Attention | r | 0.0210 | −0.2008 | −0.1987 | −0.1128 | 0.1424 | 0.4312 |
| | t | 0.1129 | 1.1039 | 1.0921 | 0.6112 | 0.7749 | 2.5734 |
| | p | 0.9109 | 0.2787 | 0.2838 | 0.5458 | 0.4447 | 0.0155 |
| Recall | r | −0.1612 | 0.0311 | −0.0081 | 0.0487 | −0.1535 | −0.1825 |
| | t | 0.8797 | 0.1676 | 0.0437 | 0.2626 | 0.8367 | 0.9993 |
| | p | 0.3862 | 0.8681 | 0.9654 | 0.7947 | 0.4096 | 0.3259 |
| Language | r | −0.0721 | −0.1745 | −0.4823 | −0.1435 | 0.2192 | 0.3394 |
| | t | 0.3894 | 0.9542 | 2.9651 | 0.7808 | 1.2099 | 1.9428 |
| | p | 0.6998 | 0.3479 | 0.0060 | 0.4412 | 0.2361 | 0.0618 |

TABLE XII

| | MCI converted to AD (Volume) (Left Side) | | | | | |
|---|---|---|---|---|---|---|
| Sub-region | PaS | PrS | S | CA1 | CA3 | CA4 |
| Orientation r | 0.1616 | 0.3354 | 0.4860 | 0.2266 | −0.0078 | 0.0959 |
| t | 0.8817 | 1.9170 | 2.9944 | 1.2529 | 0.0420 | 0.5190 |
| p | 0.3852 | 0.0651 | 0.0056 | 0.2202 | 0.9668 | 0.6077 |
| Registration r | −0.0406 | −0.0420 | −0.0445 | −0.1316 | −0.2537 | −0.2340 |
| t | 0.2188 | 0.2265 | 0.2398 | 0.7149 | 1.4126 | 1.2963 |
| p | 0.8283 | 0.8224 | 0.8121 | 0.4804 | 0.1684 | 0.2051 |
| Attention r | 0.1046 | 0.2353 | 0.3681 | 0.3701 | −0.0952 | 0.1191 |
| t | 0.5664 | 1.3039 | 2.1319 | 2.1455 | 0.5151 | 0.6461 |
| p | 0.5755 | 0.2025 | 0.0416 | 0.0404 | 0.6104 | 0.5233 |
| Recall r | 0.0291 | 0.1407 | 0.1918 | 0.1135 | 0.2987 | 0.2283 |
| t | 0.1569 | 0.7654 | 1.0526 | 0.6149 | 1.6855 | 1.2626 |
| p | 0.8764 | 0.4502 | 0.3012 | 0.5434 | 0.1026 | 0.2168 |
| Language r | 0.0635 | 0.2918 | 0.3192 | 0.1285 | 0.0576 | 0.2404 |
| t | 0.3429 | 1.6429 | 1.8141 | 0.6975 | 0.3108 | 1.3335 |
| p | 0.7341 | 0.1112 | 0.0800 | 0.4910 | 0.7582 | 0.1928 |

| Sub-region | DG | HATA | Fimbria | ML | Fissure | Tail |
|---|---|---|---|---|---|---|
| Orientation r | 0.1250 | 0.0782 | −0.3499 | 0.3083 | 0.2720 | 0.2593 |
| t | 0.6786 | 0.4223 | 2.0112 | 1.7451 | 1.5220 | 1.4458 |
| p | 0.5028 | 0.6759 | 0.0537 | 0.0916 | 0.1388 | 0.1590 |
| Registration r | −0.3462 | −0.2663 | −0.0807 | −0.1452 | −0.3379 | 0.0163 |
| t | 1.9874 | 1.4878 | 0.4358 | 0.7901 | 1.9334 | 0.0880 |
| p | 0.0564 | 0.1476 | 0.6662 | 0.4359 | 0.0630 | 0.9305 |
| Attention r | 0.1302 | −0.1388 | −0.2626 | 0.3274 | 0.1746 | 0.3879 |
| t | 0.7072 | 0.7548 | 1.4656 | 1.8659 | 0.9549 | 2.2663 |
| p | 0.4851 | 0.4565 | 0.1535 | 0.0722 | 0.3475 | 0.0311 |
| Recall r | 0.2735 | 0.2021 | 0.3906 | 0.1946 | 0.1548 | −0.1286 |
| t | 1.5310 | 1.1114 | 2.2849 | 1.0685 | 0.8439 | 0.6981 |
| p | 0.1366 | 0.2755 | 0.0298 | 0.2941 | 0.4056 | 0.4907 |
| Language r | 0.1749 | −0.2326 | 0.1269 | 0.2685 | 0.0329 | −0.0239 |
| t | 0.9568 | 1.2880 | 0.6889 | 1.5011 | 0.1770 | 0.1286 |
| p | 0.3466 | 0.2079 | 0.4963 | 0.1441 | 0.8607 | 0.8986 |

| | MCI converted to AD (Volume) (Right Side) | | | | | |
|---|---|---|---|---|---|---|
| Sub-region | PaS | PrS | S | CA1 | CA3 | CA4 |
| Orientation r | 0.0204 | 0.2401 | 0.3547 | 0.0319 | 0.1018 | 0.1512 |
| t | 0.1101 | 1.3318 | 2.0427 | 0.1720 | 0.5510 | 0.8237 |
| p | 0.9131 | 0.1933 | 0.0503 | 0.8647 | 0.5858 | 0.4168 |
| Registration r | 0.0242 | −0.1353 | −0.1515 | −0.2499 | −0.4119 | −0.0983 |
| t | 0.1302 | 0.7356 | 0.8256 | 1.3901 | 2.4340 | 0.5319 |
| p | 0.8973 | 0.4679 | 0.4158 | 0.1751 | 0.0213 | 0.5988 |
| Attention r | 0.1283 | 0.1677 | −0.0357 | −0.0571 | 0.0194 | −0.0877 |
| t | 0.6966 | 0.9163 | 0.1921 | 0.3080 | 0.1045 | 0.4741 |
| p | 0.4916 | 0.3671 | 0.8490 | 0.7602 | 0.9175 | 0.6390 |

TABLE XII-continued

| Recall | r | −0.0525 | −0.0693 | 0.1045 | −0.1251 | −0.0601 | −0.1188 |
|---|---|---|---|---|---|---|---|
| | t | 0.2833 | 0.3739 | 0.5660 | 0.6789 | 0.3244 | 0.6443 |
| | p | 0.7790 | 0.7112 | 0.5757 | 0.5026 | 0.7480 | 0.5244 |
| Language | r | 0.1771 | 0.1181 | 0.0488 | −0.1662 | −0.2094 | −0.0619 |
| | t | 0.9688 | 0.6406 | 0.2631 | 0.9078 | 1.1530 | 0.3340 |
| | p | 0.3406 | 0.5268 | 0.7944 | 0.3715 | 0.2583 | 0.7407 |

| Sub-region | | DG | HATA | Fimbria | ML | Fissure | Tail |
|---|---|---|---|---|---|---|---|
| Orientation | r | 0.1317 | 0.0827 | 0.1293 | 0.1677 | −0.0563 | −0.0254 |
| | t | 0.7155 | 0.4471 | 0.7024 | 0.9159 | 0.3035 | 0.1369 |
| | p | 0.4800 | 0.6581 | 0.4880 | 0.3673 | 0.7637 | 0.8920 |
| Registration | r | −0.1305 | −0.4943 | 0.0387 | −0.2128 | −0.1219 | −0.0292 |
| | t | 0.7091 | 3.0625 | 0.2084 | 1.1730 | 0.6617 | 0.1575 |
| | p | 0.4839 | 0.0047 | 0.8364 | 0.2503 | 0.5134 | 0.8760 |
| Attention | r | −0.0560 | 0.0153 | −0.2714 | −0.0629 | 0.0841 | 0.2479 |
| | t | 0.3020 | 0.0823 | 1.5185 | 0.3395 | 0.4544 | 1.3780 |
| | p | 0.7648 | 0.9349 | 0.1397 | 0.7367 | 0.6529 | 0.1788 |
| Recall | r | −0.1179 | 0.0311 | 0.0196 | −0.0263 | −0.1895 | −0.1713 |
| | t | 0.6396 | 0.1677 | 0.1053 | 0.1416 | 1.0394 | 0.9363 |
| | p | 0.5275 | 0.8680 | 0.9169 | 0.8884 | 0.3072 | 0.3568 |
| Language | r | −0.0432 | −0.1003 | −0.5152 | −0.1290 | 0.2111 | 0.2135 |
| | t | 0.2329 | 0.5427 | 3.2369 | 0.7006 | 1.1630 | 1.1769 |
| | p | 0.8175 | 0.5915 | 0.0030 | 0.4892 | 0.2543 | 0.2488 |

TABLE XIII

| | MCI converted to AD (Maximum Curvature) (Left Side) | | | | | |
|---|---|---|---|---|---|---|
| Sub-region | PaS | PrS | S | CA1 | CA3 | CA4 |
| Orientation r | 0.0562 | 0.1666 | 0.0377 | −0.0370 | 0.2424 | −0.0120 |
| t | 0.3030 | 0.9100 | 0.2031 | 0.1991 | 1.3456 | 0.0648 |
| p | 0.7641 | 0.3703 | 0.8405 | 0.8435 | 0.1889 | 0.9488 |
| Registration r | −0.0652 | 0.0170 | −0.0919 | 0.0260 | −0.2359 | −0.0702 |
| t | 0.3517 | 0.0915 | 0.4968 | 0.1403 | 1.3071 | 0.3791 |
| p | 0.7276 | 0.9277 | 0.6231 | 0.8894 | 0.2014 | 0.7074 |
| Attention r | 0.1453 | 0.1052 | 0.2934 | 0.0886 | −0.0103 | 0.2347 |
| t | 0.7911 | 0.5696 | 1.6530 | 0.4792 | 0.0553 | 1.3004 |
| p | 0.4353 | 0.5733 | 0.1091 | 0.6354 | 0.9563 | 0.2037 |
| Recall r | 0.0177 | −0.0400 | −0.3626 | −0.0364 | 0.0238 | −0.0342 |
| t | 0.0954 | 0.2155 | 2.0950 | 0.1963 | 0.1281 | 0.1843 |
| p | 0.9246 | 0.8309 | 0.0450 | 0.8458 | 0.8990 | 0.8551 |
| Language r | 0.0195 | −0.0957 | −0.0291 | 0.0044 | −0.1907 | 0.0908 |
| t | 0.1052 | 0.5175 | 0.1568 | 0.0239 | 1.0460 | 0.4912 |
| p | 0.9169 | 0.6088 | 0.8765 | 0.9811 | 0.3042 | 0.6270 |

| Sub-region | DG | HATA | Fimbria | ML | Fissure | Tail |
|---|---|---|---|---|---|---|
| Orientation r | −0.1105 | −0.3264 | 0.1920 | −0.2119 | −0.0905 | −0.0153 |
| t | 0.5987 | 1.8596 | 1.0537 | 1.1676 | 0.4896 | 0.0825 |
| p | 0.5540 | 0.0731 | 0.3007 | 0.2525 | 0.6281 | 0.9348 |
| Registration r | 0.1271 | −0.0153 | −0.4370 | −0.0381 | 0.2291 | 0.1208 |
| t | 0.6900 | 0.0826 | 2.6167 | 0.2055 | 1.2676 | 0.6552 |
| p | 0.4957 | 0.9347 | 0.0140 | 0.8386 | 0.2150 | 0.5175 |
| Attention r | −0.0172 | −0.5528 | −0.0759 | −0.0951 | −0.0359 | −0.2079 |
| t | 0.0928 | 3.5724 | 0.4101 | 0.5143 | 0.1935 | 1.1446 |
| p | 0.9267 | 0.0013 | 0.6847 | 0.6109 | 0.8479 | 0.2617 |
| Recall r | −0.0887 | 0.0041 | −0.2154 | −0.0299 | 0.1095 | 0.1776 |
| t | 0.4797 | 0.0220 | 1.1878 | 0.1613 | 0.5933 | 0.9721 |
| p | 0.6351 | 0.9826 | 0.2445 | 0.8730 | 0.5576 | 0.3390 |
| Language r | −0.2099 | −0.4558 | −0.3898 | 0.0613 | 0.0307 | 0.0031 |
| t | 1.1562 | 2.7575 | 2.2795 | 0.3306 | 0.1655 | 0.0167 |
| p | 0.2570 | 0.0100 | 0.0302 | 0.7433 | 0.8697 | 0.9868 |

| Sub-region | PaS | PrS | S | CA1 | CA3 | CA4 |
|---|---|---|---|---|---|---|
| Orientation r | 0.1097 | −0.0376 | 0.1434 | −0.0189 | 0.2117 | −0.1820 |
| t | 0.5945 | 0.2026 | 0.7804 | 0.1016 | 1.1662 | 0.9968 |
| p | 0.5568 | 0.8408 | 0.4415 | 0.9198 | 0.2530 | 0.3271 |
| Registration r | 0.0747 | −0.2475 | −0.0191 | 0.1689 | 0.0464 | −0.0323 |
| t | 0.4036 | 1.3757 | 0.1030 | 0.9228 | 0.2499 | 0.1739 |
| p | 0.6895 | 0.1795 | 0.9187 | 0.3637 | 0.8044 | 0.8631 |

TABLE XIII-continued

| | | | | | | | |
|---|---|---|---|---|---|---|---|
| Attention | r | −0.4294 | −0.3066 | 0.0942 | −0.1088 | 0.0742 | −0.0984 |
| | t | 2.5607 | 1.7344 | 0.5098 | 0.5894 | 0.4009 | 0.5324 |
| | p | 0.0159 | 0.0935 | 0.6140 | 0.5602 | 0.6914 | 0.5985 |
| Recall | r | −0.0671 | −0.1698 | 0.1389 | 0.0743 | 0.1950 | −0.3372 |
| | t | 0.3621 | 0.9279 | 0.7553 | 0.4010 | 1.0709 | 1.9290 |
| | p | 0.7199 | 0.3611 | 0.4561 | 0.6914 | 0.2931 | 0.0636 |
| Language | r | −0.3857 | −0.4835 | 0.2298 | −0.2276 | 0.1263 | −0.1133 |
| | t | 2.2513 | 2.9748 | 1.2718 | 1.2589 | 0.6854 | 0.6139 |
| | p | 0.0321 | 0.0059 | 0.2135 | 0.2181 | 0.4985 | 0.5441 |

| Sub-region | | DG | HATA | Fimbria | ML | Fissure | Tail |
|---|---|---|---|---|---|---|---|
| Orientation | r | −0.1675 | −0.0809 | −0.2693 | 0.0037 | 0.0949 | 0.0818 |
| | t | 0.9152 | 0.4369 | 1.5060 | 0.0200 | 0.5131 | 0.4422 |
| | p | 0.3676 | 0.6654 | 0.1429 | 0.9841 | 0.6117 | 0.6616 |
| Registration | r | 0.0324 | 0.0653 | 0.2097 | −0.1489 | −0.0842 | −0.0967 |
| | t | 0.1746 | 0.3527 | 1.1549 | 0.8109 | 0.4553 | 0.5232 |
| | p | 0.8626 | 0.7269 | 0.2576 | 0.4240 | 0.6523 | 0.6048 |
| Attention | r | −0.1712 | −0.3523 | −0.0983 | 0.1977 | 0.0770 | 0.1924 |
| | t | 0.9360 | 2.0274 | 0.5322 | 1.0863 | 0.4156 | 1.0560 |
| | p | 0.3570 | 0.0519 | 0.5986 | 0.2863 | 0.6807 | 0.2997 |
| Recall | r | −0.1491 | 0.0865 | 0.0182 | −0.2727 | −0.0984 | 0.0423 |
| | t | 0.8119 | 0.4674 | 0.0980 | 1.5264 | 0.5324 | 0.2278 |
| | p | 0.4235 | 0.6437 | 0.9226 | 0.1377 | 0.5985 | 0.8214 |
| Language | r | −0.2448 | −0.2411 | 0.1770 | 0.1764 | −0.1586 | 0.1606 |
| | t | 1.3597 | 1.3380 | 0.9685 | 0.9651 | 0.8651 | 0.8765 |
| | p | 0.1844 | 0.1913 | 0.3408 | 0.3425 | 0.3941 | 0.3880 |

TABLE XIV

| MCI converted to AD (Minimum Curvature) (Left Side) | | | | | | | |
|---|---|---|---|---|---|---|---|
| Sub-region | | PaS | PrS | S | CA1 | CA3 | CA4 |
| Orientation | r | 0.0676 | 0.1002 | 0.0393 | −0.0336 | 0.2804 | −0.0039 |
| | t | 0.3650 | 0.5422 | 0.2118 | 0.1812 | 1.5730 | 0.0208 |
| | p | 0.7178 | 0.5918 | 0.8337 | 0.8575 | 0.1266 | 0.9836 |
| Registration | l | 0.0295 | 0.0337 | −0.1047 | −0.0037 | 0.2022 | −0.0835 |
| | t | 0.1591 | 0.1815 | 0.5670 | 0.0199 | 1.1117 | 0.4514 |
| | p | 0.8747 | 0.8572 | 0.5751 | 0.9843 | 0.2754 | 0.6550 |
| Attention | r | 0.1155 | 0.0692 | 0.3160 | 0.0679 | 0.0556 | 0.2490 |
| | t | 0.6263 | 0.3736 | 1.7938 | 0.3666 | 0.3000 | 1.3847 |
| | p | 0.5360 | 0.7115 | 0.0833 | 0.7165 | 0.7663 | 0.1767 |
| Recall | r | 0.0029 | −0.0112 | −0.3581 | −0.1148 | 0.0869 | 0.0046 |
| | t | 0.0155 | 0.0601 | 2.0657 | 0.6222 | 0.4696 | 0.0246 |
| | p | 0.9877 | 0.9525 | 0.0479 | 0.5387 | 0.6421 | 0.9806 |
| Language | r | 0.0732 | 0.0233 | −0.0205 | −0.0862 | 0.1292 | 0.1223 |
| | t | 0.3950 | 0.1257 | 0.1107 | 0.4661 | 0.7017 | 0.6638 |
| | p | 0.6957 | 0.9008 | 0.9126 | 0.6446 | 0.4884 | 0.5121 |

| Sub-region | | DG | HATA | Fimbria | ML | Fissure | Tail |
|---|---|---|---|---|---|---|---|
| Orientation | r | 0.0009 | −0.3187 | 0.0018 | −0.2593 | −0.0979 | 0.0054 |
| | t | 0.0050 | 1.8105 | 0.0096 | 1.4459 | 0.5295 | 0.0293 |
| | p | 0.9960 | 0.0806 | 0.9924 | 0.1589 | 0.6005 | 0.9768 |
| Registration | r | 0.0973 | 0.0217 | −0.2265 | −0.0094 | 0.2131 | 0.1244 |
| | t | 0.5265 | 0.1171 | 1.2520 | 0.0508 | 1.1744 | 0.6750 |
| | p | 0.6026 | 0.9076 | 0.2206 | 0.9599 | 0.2498 | 0.5050 |
| Attention | r | 0.0325 | −0.5703 | −0.4059 | −0.0867 | −0.0431 | −0.2020 |
| | t | 0.1752 | 3.7386 | 2.3920 | 0.4688 | 0.2321 | 1.1109 |
| | p | 0.8621 | 0.0008 | 0.0235 | 0.6427 | 0.8181 | 0.2757 |
| Recall | r | 0.0507 | −0.0113 | −0.1186 | 0.0263 | 0.0871 | 0.1870 |
| | t | 0.2734 | 0.0608 | 0.6431 | 0.1417 | 0.4707 | 1.0251 |
| | p | 0.7865 | 0.9520 | 0.5252 | 0.8883 | 0.6414 | 0.3138 |
| Language | r | 0.1986 | −0.4759 | −0.5163 | 0.1172 | 0.0046 | 0.0614 |
| | t | 1.0912 | 2.9140 | 3.2462 | 0.6356 | 0.0245 | 0.3313 |
| | p | 0.2842 | 0.0068 | 0.0029 | 0.5300 | 0.9806 | 0.7428 |

| MCI converted to AD (Minimum Curvature) (Right Side) | | | | | | | |
|---|---|---|---|---|---|---|---|
| Sub-region | | PaS | PrS | S | CA1 | CA3 | CA4 |
| Orientation | r | 0.1406 | 0.2952 | 0.1436 | 0.0692 | 0.2429 | −0.2028 |
| | t | 0.7646 | 1.6638 | 0.7816 | 0.3736 | 1.3482 | 1.1151 |
| | p | 0.4507 | 0.1069 | 0.4408 | 0.7114 | 0.1880 | 0.2739 |

TABLE XIV-continued

| | | | | | | | |
|---|---|---|---|---|---|---|---|
| Registration | r | 0.0589 | 0.0110 | 0.0261 | 0.1978 | 0.0376 | −0.0257 |
| | t | 0.3180 | 0.0591 | 0.1406 | 1.0868 | 0.2025 | 0.1385 |
| | p | 0.7528 | 0.9532 | 0.8892 | 0.2861 | 0.8409 | 0.8908 |
| Attention | r | −0.3415 | −0.5675 | −0.1161 | 0.0419 | 0.0541 | −0.0726 |
| | t | 1.9568 | 3.7119 | 0.6297 | 0.2261 | 0.2919 | 0.3920 |
| | p | 0.0601 | 0.0009 | 0.5338 | 0.8227 | 0.7724 | 0.6979 |
| Recall | r | −0.0494 | −0.0231 | 0.0255 | 0.1100 | 0.2964 | −0.3471 |
| | t | 0.2662 | 0.1247 | 0.1371 | 0.5958 | 1.6710 | 1.9933 |
| | p | 0.7920 | 0.9016 | 0.8919 | 0.5559 | 0.1055 | 0.0557 |
| Language | r | −0.1917 | −0.4940 | 0.1023 | −0.0628 | 0.1250 | −0.1071 |
| | t | 1.0521 | 3.0600 | 0.5537 | 0.3388 | 0.6787 | 0.5800 |
| | p | 0.3014 | 0.0047 | 0.5840 | 0.7372 | 0.5027 | 0.5664 |

| Sub-region | | DG | HATA | Fimbria | ML | Fissure | Tail |
|---|---|---|---|---|---|---|---|
| Orientation | r | −0.1147 | 0.2628 | −0.4315 | 0.0244 | 0.0426 | 0.0534 |
| | t | 0.6217 | 1.4667 | 2.5756 | 0.1317 | 0.2294 | 0.2882 |
| | p | 0.5390 | 0.1532 | 0.0154 | 0.8961 | 0.8202 | 0.7752 |
| Registration | r | 0.0222 | 0.0418 | 0.0799 | −0.0773 | −0.1054 | −0.1110 |
| | t | 0.1195 | 0.2252 | 0.4316 | 0.4173 | 0.5707 | 0.6016 |
| | p | 0.9057 | 0.8234 | 0.6692 | 0.6796 | 0.5726 | 0.5521 |
| Attention | r | −0.1512 | −0.5168 | −0.1799 | 0.1935 | 0.0716 | 0.1612 |
| | t | 0.8238 | 3.2507 | 0.9848 | 1.0621 | 0.3865 | 0.8796 |
| | p | 0.4168 | 0.0029 | 0.3329 | 0.2970 | 0.7020 | 0.3863 |
| Recall | r | −0.1771 | 0.0071 | 0.1390 | −0.2005 | −0.1066 | 0.0205 |
| | t | 0.9688 | 0.0382 | 0.7558 | 1.1018 | 0.5772 | 0.1102 |
| | p | 0.3406 | 0.9698 | 0.4558 | 0.2796 | 0.5683 | 0.9130 |
| Language | r | −0.2362 | −0.3794 | 0.1958 | 0.1449 | −0.1556 | 0.1429 |
| | t | 1.3093 | 2.2080 | 1.0750 | 0.7886 | 0.8483 | 0.7777 |
| | p | 0.2007 | 0.0353 | 0.2913 | 0.4368 | 0.4032 | 0.4431 |

TABLE XV

| MCI converted to AD (Average Ratio of Principal Curvature) (Left Side) | | | | | | | |
|---|---|---|---|---|---|---|---|
| Sub-region | | PaS | PrS | S | CA1 | CA3 | CA4 |
| Orientation | r | −0.1291 | 0.0886 | −0.0542 | 0.0778 | 0.2422 | −0.1921 |
| | t | 0.7010 | 0.4788 | 0.2921 | 0.4203 | 1.3445 | 1.0544 |
| | p | 0.4889 | 0.6357 | 0.7723 | 0.6774 | 0.1892 | 0.3004 |
| Registration | r | −0.0037 | −0.0112 | −0.0860 | 0.0448 | 0.2152 | 0.1990 |
| | t | 0.0199 | 0.0602 | 0.4651 | 0.2417 | 1.1869 | 1.0936 |
| | p | 0.9842 | 0.9524 | 0.6454 | 0.8107 | 0.2449 | 0.2832 |
| Attention | r | −0.2724 | 0.0367 | −0.0310 | 0.1514 | −0.1368 | 0.1396 |
| | t | 1.5246 | 0.1977 | 0.1669 | 0.8247 | 0.7437 | 0.7593 |
| | p | 0.1382 | 0.8447 | 0.8686 | 0.4163 | 0.4631 | 0.4538 |
| Recall | r | −0.2285 | −0.1802 | −0.1304 | 0.0054 | 0.0811 | −0.0715 |
| | t | 1.2642 | 0.9866 | 0.7081 | 0.0291 | 0.4381 | 0.3858 |
| | p | 0.2162 | 0.3320 | 0.4846 | 0.9770 | 0.6645 | 0.7025 |
| Language | r | −0.1191 | −0.1871 | −0.1841 | 0.1881 | 0.0787 | 0.1758 |
| | t | 0.6460 | 1.0256 | 1.0089 | 1.0313 | 0.4253 | 0.9617 |
| | p | 0.5234 | 0.3136 | 0.3214 | 0.3109 | 0.6737 | 0.3442 |

| Sub-region | | DG | HATA | Fimbria | ML | Fissure | Tail |
|---|---|---|---|---|---|---|---|
| Orientation | r | 0.0851 | −0.0783 | 0.0791 | 0.2617 | 0.1215 | −0.1648 |
| | t | 0.4597 | 0.4228 | 0.4272 | 1.4601 | 0.6591 | 0.8998 |
| | p | 0.6492 | 0.6755 | 0.6724 | 0.1550 | 0.5150 | 0.3756 |
| Registration | r | 0.2357 | −0.1843 | −0.0325 | −0.0045 | −0.2380 | −0.2766 |
| | t | 1.3059 | 1.0099 | 0.1751 | 0.0244 | 1.3199 | 1.5499 |
| | p | 0.2019 | 0.3209 | 0.8623 | 0.9807 | 0.1972 | 0.1320 |
| Attention | r | −0.2168 | 0.0215 | −0.0511 | −0.2030 | 0.1989 | −0.3142 |
| | t | 1.1960 | 0.1160 | 0.2756 | 1.1162 | 1.0929 | 1.7820 |
| | p | 0.2414 | 0.9084 | 0.7848 | 0.2735 | 0.2834 | 0.0852 |
| Recall | r | 0.1981 | −0.0760 | 0.0549 | 0.1772 | 0.1074 | 0.0797 |
| | t | 1.0882 | 0.4104 | 0.2963 | 0.9696 | 0.5820 | 0.4304 |
| | p | 0.2855 | 0.6845 | 0.7691 | 0.3403 | 0.5651 | 0.6701 |
| Language | r | 0.1999 | −0.0010 | 0.2397 | −0.3340 | 0.1724 | −0.1363 |
| | t | 1.0987 | 0.0056 | 1.3299 | 1.9080 | 0.9427 | 0.7406 |
| | p | 0.2809 | 0.9956 | 0.1939 | 0.0663 | 0.3536 | 0.4649 |

| Sub-region | | PaS | PrS | S | CA1 | CA3 | CA4 |
|---|---|---|---|---|---|---|---|
| Orientation | r | −0.1111 | 0.1666 | −0.3344 | −0.3074 | 0.0857 | 0.1164 |
| | t | 0.6020 | 0.9101 | 1.9107 | 1.7394 | 0.4633 | 0.6312 |
| | p | 0.5519 | 0.3703 | 0.0660 | 0.0926 | 0.6466 | 0.5329 |

TABLE XV-continued

| | | | | | | | |
|---|---|---|---|---|---|---|---|
| Registration | r | −0.0462 | 0.2675 | 0.0924 | 0.0876 | 0.1323 | 0.0781 |
| | t | 0.2490 | 1.4951 | 0.4997 | 0.4736 | 0.7189 | 0.4220 |
| | p | 0.8051 | 0.1457 | 0.6210 | 0.6394 | 0.4780 | 0.6761 |
| Attention | r | −0.3563 | 0.1256 | 0.0671 | −0.2666 | −0.2466 | 0.1803 |
| | t | 2.0533 | 0.6816 | 0.3624 | 1.4897 | 1.3702 | 0.9872 |
| | p | 0.0492 | 0.5009 | 0.7197 | 0.1471 | 0.1811 | 0.3317 |
| Recall | r | 0.2355 | 0.2364 | −0.1102 | 0.0050 | 0.0380 | 0.1787 |
| | t | 1.3049 | 1.3103 | 0.5971 | 0.0271 | 0.2049 | 0.9782 |
| | p | 0.2022 | 0.2004 | 0.5551 | 0.9786 | 0.8391 | 0.3361 |
| Language | r | −0.1270 | 0.1161 | 0.0492 | −0.2298 | 0.0640 | 0.1522 |
| | t | 0.6897 | 0.6294 | 0.2655 | 1.2716 | 0.3453 | 0.8295 |
| | p | 0.4959 | 0.5340 | 0.7925 | 0.2136 | 0.7324 | 0.4136 |

| Sub-region | | DG | HATA | Fimbria | ML | Fissure | Tail |
|---|---|---|---|---|---|---|---|
| Orientation | r | 0.1115 | 0.0717 | 0.0902 | 0.1002 | 0.1800 | −0.3468 |
| | t | 0.6041 | 0.3871 | 0.4880 | 0.5423 | 0.9852 | 1.9909 |
| | p | 0.5505 | 0.7015 | 0.6293 | 0.5918 | 0.3327 | 0.0560 |
| Registration | r | −0.1917 | −0.8234 | 0.0944 | 0.0490 | 0.1112 | −0.0757 |
| | t | 1.0516 | 7.8131 | 0.5106 | 0.2640 | 0.6027 | 0.4087 |
| | p | 0.3017 | 0.0000 | 0.6135 | 0.7936 | 0.5514 | 0.6858 |
| Attention | r | −0.2108 | 0.0858 | 0.0611 | −0.0013 | 0.0544 | −0.1721 |
| | t | 1.1615 | 0.4636 | 0.3297 | 0.0071 | 0.2932 | 0.9411 |
| | p | 0.2549 | 0.6464 | 0.7440 | 0.9944 | 0.7714 | 0.3544 |
| Recall | r | 0.0832 | 0.0370 | 0.0524 | 0.1359 | −0.1244 | −0.0571 |
| | t | 0.4498 | 0.1995 | 0.2825 | 0.7389 | 0.6753 | 0.3082 |
| | p | 0.6562 | 0.8433 | 0.7796 | 0.4659 | 0.5048 | 0.7601 |
| Language | r | −0.0269 | −0.3748 | −0.0442 | 0.1172 | 0.0826 | −0.1310 |
| | t | 0.1448 | 2.1772 | 0.2385 | 0.6354 | 0.4465 | 0.7117 |
| | p | 0.8859 | 0.0377 | 0.8132 | 0.5301 | 0.6585 | 0.4823 |

Since the correlation we found in the experimental group (MCI converted to AD) may not be caused by Alzheimer's disease, it might be simply a phenomenon of normal aging. Therefore, in addition to do the hypothesis testing to the experimental group (MCI converted to AD), we also performed on the control group (MCI non-converter). If the neuropsychological data and neuroimaging data are highly correlated in the experimental group but no correlated in the control group, this can indicate that the correlation we found is not just a normal aging phenomenon but a phenomenon unique to Alzheimer's disease. The experimental results satisfying the above restrictions are shown in Table XVI-Table XVIII.

TABLE XVI

| | | MCI converted to AD | | | |
|---|---|---|---|---|---|
| | | Left Side | | Right Side | |
| Surface Area | | Presubic-ulum | Subic-ulum | Presubic-ulum | Subic-ulum |
| Orientation | r | 0.3858 | 0.3324 | 0.3494 | 0.3798 |
| | t | 2.2520 | 1.8980 | 2.0084 | 2.2112 |
| | p | 0.0321 | 0.0677 | 0.0540 | 0.0351 |

| | | MCI non-converter | | | |
|---|---|---|---|---|---|
| | | Left Side | | Right Side | |
| Surface Area | | Presubic-ulum | Subic-ulum | Presubic-ulum | Subic-ulum |
| Orientation | r | −0.1506 | 0.1270 | 0.1597 | 0.2016 |
| | t | 0.8202 | 0.6893 | 0.8712 | 1.1082 |
| | p | 0.4188 | 0.4961 | 0.3908 | 0.2769 |

TABLE XVII

| | | MCI converted to AD | | | |
|---|---|---|---|---|---|
| | | Left Side | | Right Side | |
| Volume | | Presubic-ulum | Subic-ulum | Presubic-ulum | Subic-ulum |
| Orientation | r | 0.3354 | 0.4860 | 0.2401 | 0.3547 |
| | t | 1.9170 | 2.9944 | 1.3318 | 2.0427 |
| | p | 0.0651 | 0.0056 | 0.1933 | 0.0503 |

| | | MCI non-converter | | | |
|---|---|---|---|---|---|
| | | Left Side | | Right Side | |
| Volume | | Presubic-ulum | Subic-ulum | Presubic-ulum | Subic-ulum |
| Orientation | r | −0.1735 | 0.0219 | 0.0222 | 0.0386 |
| | t | 0.9486 | 0.1182 | 0.1198 | 0.2082 |
| | p | 0.3507 | 0.9067 | 0.9054 | 0.8365 |

TABLE XVIII

| | | MCI converted to AD | |
|---|---|---|---|
| Surface Area | | Left Side Hippocampal Tail | Right Side Hippocampal Tail |
| Orientation | r | 0.4316 | 0.3607 |
| | t | 2.5766 | 2.0826 |
| | p | 0.0153 | 0.0462 |
| Attention | r | 0.5816 | 0.4312 |
| | t | 3.8504 | 2.5734 |
| | p | 0.0006 | 0.0155 |

TABLE XVIII-continued

| | | MCI non-converter | |
|---|---|---|---|
| Surface Area | | Left Side Hippocampal Tail | Right Side Hippocampal Tail |
| Orientation | r | −0.0686 | 0.0237 |
| | t | 0.3705 | 0.1276 |
| | p | 0.7137 | 0.8993 |
| Attention | r | 0.1729 | 0.0190 |
| | t | 0.9453 | 0.1025 |
| | p | 0.3523 | 0.9190 |

In addition, the surface area on the left and right hippocampal tail were also found to be statistically significant between the MMSE orientation and attention score in this data.

Based on the results of the hypothesis testing, we can infer that the surface area of the left presubiculum and right subiculum is statistically significant with the MMSE sub-item orientation score (p<0.05). In addition, although the surface area of the left subiculum and right presubiculum did not satisfy the hypothesis testing, its p-value is also very close to the significance level α. We also performed the same hypothesis testing on the control group. However, this phenomenon did not be observed in the control group. Therefore, we can infer that this can be regarded as a phenomenon unique to Alzheimer's disease in this data. We also found the similar phenomenon in the volume of pre-subiculum and subiculum.

According to the foregoing results, upon using the neural network to predict the Alzheimer's disease, the surface area change data of presubiculum may be replaced by the change data of orientation scores of the two visits (in some embodiments, the change data of orientation scores of the two visits is the difference between the orientation score of the second visit and the orientation score of the first visit); or the volume change data of presubiculum may be replaced by the change data of orientation scores of the two visits; or the surface area change data of subiculum may be replaced by the change data of orientation scores of the two visits; or the volume change data of subiculum may be replaced by the change data of orientation scores of the two visits.

Figure 10:
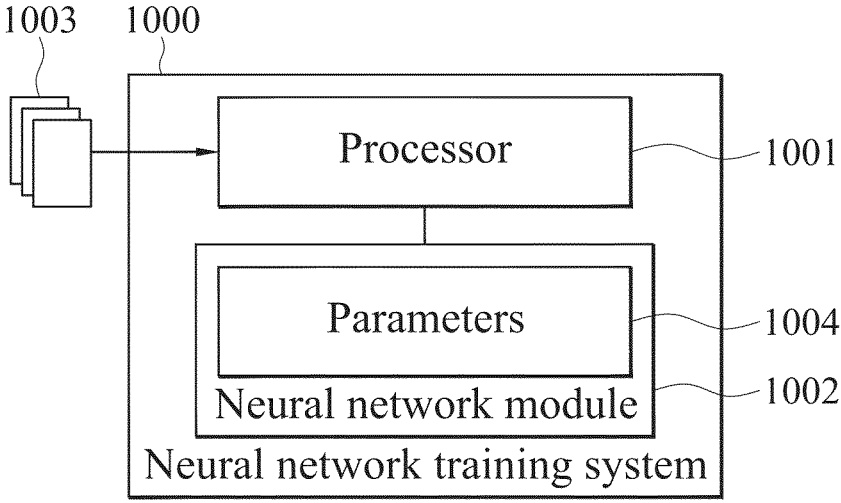
FIG. 10 is a block diagram of a neural network training system in accordance with an embodiment of the present invention.

FIG. 10 is a block diagram of a neural network training system in accordance with an embodiment of the present invention. Please refer to FIG. 10, the neural network training system 1000 comprises a processor 1001 and a neural network module 1002. The neural network module 1002 comprises a plurality of parameters 1004. The processor 1001 can receive data 1003 from the outside. The data 1003 may contain the foregoing MRI images. By calling the function of FreeSurfer, the processor 1001 can obtain each of the sections of the Hippocampus and the volume, the surface area, the maximum principal curvature, the minimum principal curvature, and the ratio of principal curvatures of each of the sections of the Hippocampus. The sections of the Hippocampus comprise alveus, parasubiculum, Cornu Ammonis 1 (CA1), Cornu Ammonis 2/3 (CA2/3), Cornu Ammonis 4 (CA4), GC-DG, HATA, Fimbria, Molecular layer, Hippocampal fissure, and Hippocampal tail.

FIG. 12 is a flowchart of a neural network training method in accordance with an embodiment of the present invention. Please refer to FIG. 10 and FIG. 12 at the same time, the neural network training method includes steps S1201 to S1204. In the step S1201, the processor 1001 obtains a plurality of historical data from the outside. Each of the plurality of historical data includes a first MMSE score, a second MMSE score, and an Alzheimer's marker, wherein the first MMSE score indicates the MMSE score of a subject in a first visit to see a doctor in which the subject is diagnosed with MCI, the second MMSE score indicates the MMSE score of the subject in a second visit after a specific period of time of the first visit, and the Alzheimer's marker for determining whether the subject has the Alzheimer's disease in the second visit. The first time marker is the time when the subject is diagnosed with MCI in the first visit, and the second time marker is the time of the second visit of the subject.

In the step S1202, the processor 1001 obtains a plurality of historical orientation change data $O_k$ according to the orientation score of the first MMSE score (for the sake of convenience, also referred to as the first orientation score) and the orientation score of the second MMSE score (for the sake of convenience, also referred to as the second orientation score) of each of the plurality of historical data, wherein each of the plurality of historical orientation change data corresponds to a corresponding one of the plurality of historical data. The historical orientation change data $O_k$ can be calculated through the following equation:

$$O_k = \frac{k_{second\ visit} - k_{first\ visit}}{k_{first\ visit}},$$

wherein, $k_{second\ visit}$ indicates the second orientation score of the subject, and $k_{first\ visit}$ indicates the first orientation score of the subject.

It is noted that, in some embodiments of the present invention, $O_k$ is calculated through the following equation: $O_k = k_{second\ visit} - k_{first\ visit}$.

In the step S1203, the processor 1001 obtains a plurality of historical MMSE change data H g according to the first MMSE score and the second MMSE score of each of plurality of historical data, wherein each of plurality of historical MMSE change data corresponds to a corresponding one of the plurality of historical data. The historical MMSE change data H g can be calculated through the following equation:

$$H_g = \frac{g_{second\ visit} - g_{first\ visit}}{g_{first\ visit}},$$

wherein, $g_{second\ visit}$ indicates the second MMSE score of the subject, and $g_{first\ visit}$ indicates the first MMSE score of the subject.

It is noted that, in some embodiments of the present invention, $H_g$ is calculated through the following equation: $H_g = g_{second\ visit} - g_{first\ visit}$.

In the step S1204, the processor 1001 trains the neural network module 1002 to obtain the parameters which have been trained by using a training set comprising the plurality of historical orientation change data $O_k$, the plurality of historical MMSE change data $H_g$, and the Alzheimer's marker of each of the plurality of historical data.

FIG. 13 is a flowchart of a neural network training method in accordance with an embodiment of the present invention. Please refer to FIG. 10 and FIG. 13 at the same time, in some embodiments, each of the plurality of historical data includes a first brain MRI data and a second brain MRI data, wherein the first brain MRI data indicates the brain MRI data of a subject in a first visit in which the subject is diagnosed with MCI, and the second brain MRI data indicates the brain MRI of the subject in a second visit after a specific period of time of the first visit. Therefore, the first brain MRI data corresponds to the first time marker, and the second brain MRI data corresponds to the second time marker.

In this embodiment, the neural network training method further comprises steps S1301 and S1302. In the step S1301, the processor 1001 extracts a plurality of corresponding data corresponding to the first time marker (the first visit) from the first brain MRI data of the plurality of historical data of all the subjects and extracts a plurality of second corresponding data corresponding to the second time marker (the second visit) from the second brain MRI data of the plurality of historical data of all the subjects. The plurality of first corresponding data of each of the biomarkers corresponds to a corresponding one of the subjects in a one-to-one correspondence, and the plurality of second corresponding data of each of the biomarkers corresponds to a corresponding one of the subjects in a one-to-one correspondence. Each of the biomarkers is selected from the group consisting of a volume, a surface area, a maximum principal curvature, a minimum principal curvature, and a ratio of principal curvatures of alveus; a volume, a surface, a maximum principal curvature, a minimum principal curvature, and a ratio of principal curvatures of parasubiculum; a volume, a surface area, a maximum principal curvature, a minimum principal curvature, and a ratio of principal curvatures of Cornu Ammonis 1 (CA1); a volume, a surface area, a maximum principal curvature, a minimum principal curvature, and a ratio of principal curvatures of Cornu Ammonis 2/3 (CA2/3); a volume, a surface area, a maximum principal curvature, a minimum principal curvature, and a ratio of principal curvatures of Cornu Ammonis 4 (CA4); a volume, a surface area, a maximum principal curvature, a minimum principal curvature, and a ratio of principal curvatures of GC-DG; a volume, a surface area, a maximum principal curvature, a minimum principal curvature, and a ratio of principal curvatures of HATA; a volume, a surface area, a maximum principal curvature, a minimum principal curvature, and a ratio of principal curvatures of Fimbria; a volume, a surface area, a maximum principal curvature, a minimum principal curvature, and a ratio of principal curvatures of Molecular layer; a volume, a surface area, a maximum principal curvature, a minimum principal curvature, and a ratio of principal curvatures of Hippocampal fissure; a volume, a surface area, a maximum principal curvature, a minimum principal curvature, and a ratio of principal curvatures of Hippocampal tail; a maximum principal curvature, a minimum principal curvature, and a ratio of principal curvatures of presubiculum; and a maximum principal curvature, a minimum principal curvature, and a ratio of principal curvatures of subiculum. It is noted that, as mentioned above, upon using the neural network to predict the Alzheimer's disease, the surface area change data of presubiculum may be replaced by the change data of orientation scores of the two visits; or the volume change data of presubiculum may be replaced by the change data of orientation scores of the two visits; or the surface area change data of subiculum may be replaced by the change data of orientation scores of the two visits; or the volume change data of subiculum may be replaced by the change data of orientation scores of the two visits. Therefore, the volume and the surface area of the presubiculum and the volume and the surface area of the subiculum are not contained in the group.

For example, the biomarkers are chosen as the volume of CA1 and the maximum principal curvature of CAL The processor 1001 extracts the volume of CA1 of all the subjects in the first visit as the plurality of first corresponding data of the volume of CA1, and the processor 1001 extracts the maximum principal curvature of CA1 of all the subjects in the first visit as the plurality of first corresponding data of the maximum principal curvature of CA1. The processor 1001 extracts the volume of CA1 of all the subjects in the second visit as the plurality of second corresponding data of the volume of CA1, and the processor 1001 extracts the maximum principal curvature of CA1 of all the subjects in the second visit as the plurality of second corresponding data of the maximum principal curvature of CA1. The plurality of first corresponding data of the volume of CA1, the plurality of second corresponding data of the volume of CA1, the plurality of first corresponding data of the maximum principal curvature of CA1, and the plurality of second corresponding data of the maximum principal curvature of CA1 correspond to the subjects in a one-to-one correspondence, respectively.

In the step S1301, the processor 1001 obtains a plurality of biomarker change data according to the plurality of first corresponding data and the plurality of second corresponding data of each of the biomarkers. In this embodiment, for each of the biomarkers, the processor 1001 calculates the biomarker change data $B_f$ for a corresponding one of the subjects according to the following equation:

$$ B_f = \frac{f_{second\ visit} - f_{first\ visit}}{f_{first\ visit}}, $$

wherein, $f_{second\ visit}$ indicates the biomarker data in the second visit of the subject, $f_{first}$ visit indicates the biomarker data in the first visit of the subject. For example, if the biomarker is the maximum principal curvature of CA1, the change data of the maximum principal curvature of CA1 is (the data of the maximum principal curvature of CA1 in the second visit—the data of the maximum principal curvature of CA1 in the first visit)/the data of the maximum principal curvature of CA1 in the first visit. Through the calculation of the biomarker change data $B_f$ of each of the subjects, the plurality of biomarker change data of each of the biomarkers can be obtained.

It is noted that, in some embodiments of the present invention, $B_f$ is calculated through the following equation: $H_g = f_{second\ visit} - f_{first\ visit}$.

In this embodiment, the training set further comprises the plurality of biomarker change data. In other words, in this embodiment, the processor 1001 trains the neural network module 1002 to obtain a plurality of parameters which have been trained by using the training set comprising the plurality of biomarker change data in the step S1204.

In some embodiments of the present disclosure, the neural network module 1002 adopts the neural network architecture shown in FIG. 5. In some embodiments, the neural network module 1002 adopts a neural network architecture constructed by a convolutional neural network layer and a fully connected sublayer with a plurality of hidden layers, but the present disclosure is not limited thereto.

Figure 11:
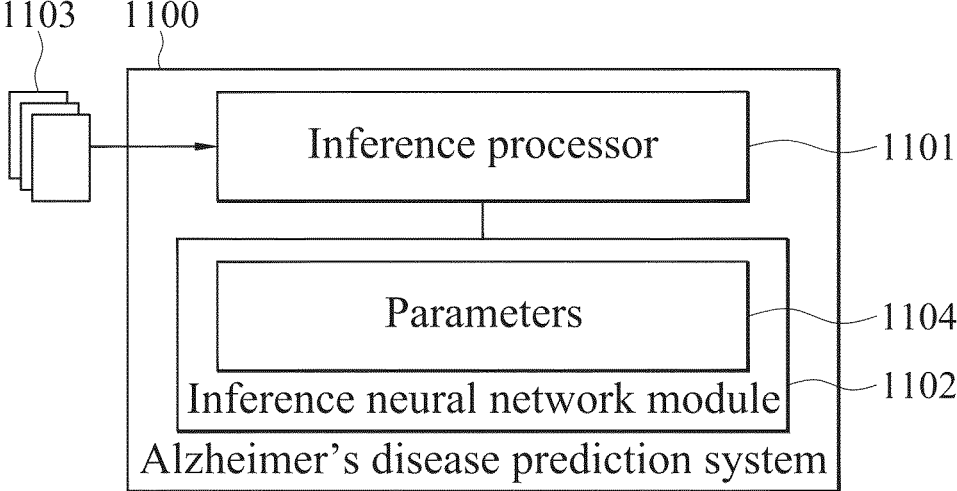
FIG. 11 is a block diagram of an Alzheimer's disease prediction system in accordance with an embodiment of the present invention.

FIG. 11 is a block diagram of an Alzheimer's disease prediction system according to an embodiment of the present invention. Please refer to FIG. 11, the Alzheimer's disease prediction system 1100 includes an inference processor 1101 and an inference neural network module 1102. The inference neural network module 1102 further includes a plurality of parameters which have been trained 1103. The processor 1101 may receive data 1104 from the outside. The data 1104 may comprise a third brain MRI data, a third MMSE score, a fourth brain MRI data, and a fourth MMSE score, wherein the third brain MRI data and the third MMSE score are the brain MRI data and the MMSE score of a patient to be predicted in a first visit in which the patient to be predicted is diagnosed with MCI, and the fourth brain MRI data and the fourth MMSE score are the brain MRI data and the MMSE score of the patient to be predicted in a second visit after a specific period of time of the first visit. The time when the subject is diagnosed with MCI in the first visit is a third time marker, and the time of the second visit of the subject is a fourth time marker. The parameters which have been trained 1103 of the inference neural network module 1102 may adopt the parameters which have been trained obtained from the neural network training system 1000.

FIG. 14 is a flowchart of an Alzheimer's disease prediction method in accordance with an embodiment of the present invention. Please refer to FIG. 11, FIG. 12, and FIG. 14, in the embodiment shown in FIG. 14, the parameters which have been trained 1103 of the inference neural network module 1102 adopt the parameters which have been trained obtained from the neural network training method shown in FIG. 12. In the embodiment shown in FIG. 14, the Alzheimer's disease prediction method includes steps S1401 to S1404.

In the step S1401, the inference processor 1101 obtains a third MMSE score and a fourth MMSE score of a patient to be predicted from the outside, wherein the third MMSE score has the third time marker, and the fourth MMSE score has the fourth time marker. In the step S1402, the inference processor 1101 obtains an orientation change data according to the orientation score of the third MMSE score (for the sake of convenience, also referred to as the third orientation score) and the orientation score of the fourth MMSE score (for the sake of convenience, also referred to as the fourth orientation score). The orientation change data $Q_l$ can be calculated through the following equation:

$$Q_l = \frac{l_{second\ visit} - l_{first\ visit}}{l_{first\ visit}},$$

wherein, $l_{second\ visit}$ indicates the fourth orientation score of the subject, $l_{first\ visit}$ indicates the third orientation score of the subject.

It is noted that, in some embodiments of the present invention, $Q_l$ is calculated through the following equation: $H_g = l_{second\ visit} - l_{first\ visit}$.

In the step S1403, the inference processor 1101 obtains an MMSE change data $P_h$ according to the third MMSE score and the fourth MMSE score, wherein the MMSE change data $P_h$ can be calculated through the following equation:

$$P_h = \frac{h_{second\ visit} - h_{first\ visit}}{h_{first\ visit}},$$

Wherein, $h_{second}$ visit indicates the second MMSE score of the subject, and $h_{first}$ visit indicates the first MMSE score of the subject.

It is noted that, in some embodiments of the present invention, $P_h$ is calculated through the following equation: $H_g = h_{second\ visit} - h_{first\ visit}$.

In the step S1404, the inference processor 1101 inputs the orientation change data $Q_l$ and the MMSE change data $P_h$ to the inference neural network module 1102 so as to obtain an Alzheimer's disease prediction result according to the inference neural network module 1102, the orientation change data $Q_l$, and the MMSE change data $P_h$, wherein the inference neural network module 1102 further includes a plurality of parameters which have been trained.

FIG. 15 is a flowchart of an Alzheimer's disease prediction method in accordance with an embodiment of the present invention. Please refer to FIG. 11, FIG. 13, and FIG. 15, in the embodiment shown in FIG. 15, the parameters which have been trained 1103 of the inference neural network module 1102 adopt the parameters which have been trained obtained from the neural network training method shown in FIG. 13. In the embodiment shown in FIG. 15, the Alzheimer's disease prediction method includes steps S1501 to S1505.

As compared with the embodiment shown in FIG. 14, the step S1502 and the step S1503 are respectively identical with the step S1402 and the step S1403, and the details are not iterated again. In the step S1501, the inference processor 1101 obtains a third brain MRI data, a fourth brain MRI data, a third MMSE score, and a fourth MMSE score of a patient to be predicted from the outside, wherein the third MMSE score has a third time marker, the fourth MMSE score has a fourth time marker, the third brain MRI data corresponds to the third time marker, and the fourth brain MRI data corresponds to the fourth time marker.

In the step S1504, for each of the biomarkers, the inference processor 1101 obtains a plurality of image feature change data corresponding to the biomarkers according to the third brain MRI data and the fourth brain MRI data. In this embodiment, the inference processor 1101 calculates the image feature change data $C_k$ corresponding to each of the biomarkers through the following equation:

$$C_k = \frac{k_{second\ visit} - k_{first\ visit}}{k_{first\ visit}}.$$

Wherein, $k_{second\ visit}$ indicates the biomarker data of the patient to be predicted in the second visit, and $k_{first\ visit}$ indicates the biomarker data of the patient to be predicted in the first visit. For example, if the biomarker is the maximum principal curvature of CA1, the change data of the maximum principal curvature of CA1 is (the data of the maximum principal curvature of CA1 in the second visit—the data of the maximum principal curvature of CA1 in the first visit)/ the data of the maximum principal curvature of CA1 in the first visit. Through the calculation of all the biomarkers $C_k$ of each of the patients to be predicted (for example, the volume of CA1, the maximum principal curvature of CA1, or the like), the plurality of image feature change data corresponding to each of the biomarkers can be obtained.

It is noted that, in some embodiments of the present invention, $C_k$ is calculated through the following equation: $H_g = k_{second\ visit} - k_{first\ visit}$.

In the step S1505, the inference processor 1101 inputs the orientation change data $Q_l$, the MMSE change data $P_h$, and the image feature change data $C_k$ corresponding to each of the biomarkers to the inference neural network module 1102 so as to obtain an Alzheimer's disease prediction result according to the inference neural network module 1102, the orientation change data $Q_1$, the MMSE change data $P_h$, and the image feature change data $C_k$ corresponding to each of the biomarkers, wherein the inference neural network module 1102 further includes a plurality of parameters which have been trained.

Please refer to FIG. 10 and FIG. 11 again, in some embodiments of the present invention, the processor 1001 and the inference processor 1101 may be an integrated circuit chip with signal processing capability. During implementation, the methods and steps disclosed in the foregoing embodiments may be achieved by the integrated logic circuit of the hardware in the processors 1201-1 through 1201-R or software instructions. The processors 1201-1 through 1201-R may be general purpose processors, such as central processing units (CPUs), tensor processing units, digital signal processors (DSPs), application specific integrated circuits (ASICs), field-programmable gate arrays (FPGAs,) or other programmable logic devices which can implement or perform the methods and steps disclosed in the foregoing embodiments. For the implementation of the embodiments, the methods and steps disclosed in the embodiments can be achieved through the integrated logic circuits of the hardware in the processors 1201-1 to 1201R. The neural network module 1002 and the inference neural network module 1102 may be implemented in the form of hardware or software and stored in the memory of a computer system.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. A neural network training system comprising:
a neural network module having a plurality of parameters; and
a processor configured to:
obtain a plurality of historical data, wherein each of the plurality of historical data comprises a first Mini-Mental State Examination (MMSE) score, a second MMSE score, and an Alzheimer's marker, wherein the first MMSE score has a first time marker, and the second MMSE score has a second time marker;
obtain a plurality of historical orientation change data according to a first orientation score of the first MMSE score and a second orientation score of the second MMSE score of each of the plurality of historical data;
obtain a plurality of historical change data according to the first MMSE score and the second MMSE score of each of the plurality of historical data; and
train the neural network module to obtain the parameters which have been trained by using a training set comprising the plurality of historical orientation change data, the plurality of historical MMSE change data, and the Alzheimer's marker of each of the plurality of historical data;
wherein each of the plurality of historical data comprises a first brain magnetic resonance imaging (MRI) data and a second brain MRI data, the first brain MRI data corresponds to the first time marker, and the second brain MRI data corresponds to the second time marker; and wherein the processor is further configured to:
extract a plurality of first corresponding data corresponding to the first time marker from the first brain MRI data of the plurality of historical data and extract a plurality of second corresponding data corresponding to the second time marker from the second brain MRI data of the plurality of historical data for each of biomarkers among a plurality of the biomarkers; and
obtain a plurality of biomarker change data according to the plurality of first corresponding data and the plurality of second corresponding data of each of the biomarkers;
wherein the training set comprises the plurality of biomarker change data; wherein each of the biomarkers is selected from the group consisting of a volume, a surface area, a maximum principal curvature, a minimum principal curvature, and a ratio of principal curvatures of alveus; a volume, a surface, a maximum principal curvature, a minimum principal curvature, and a ratio of principal curvatures of parasubiculum; a volume, a surface area, a maximum principal curvature, a minimum principal curvature, and a ratio of principal curvatures of Cornu Ammonis 1 (CA1); a volume, a surface area, a maximum principal curvature, a minimum principal curvature, and a ratio of principal curvatures of Cornu Ammonis 2/3 (CA2/3); a volume, a surface area, a maximum principal curvature, a minimum principal curvature, and a ratio of principal curvatures of Cornu Ammonis 4 (CA4); a volume, a surface area, a maximum principal curvature, a minimum principal curvature, and a ratio of principal curvatures of GC-DG; a volume, a surface area, a maximum principal curvature, a minimum principal curvature, and a ratio of principal curvatures of HATA; a volume, a surface area, a maximum principal curvature, a minimum principal curvature, and a ratio of principal curvatures of Fimbria; a volume, a surface area, a maximum principal curvature, a minimum principal curvature, and a ratio of principal curvatures of Molecular layer; a volume, a surface area, a maximum principal curvature, a minimum principal curvature, and a ratio of principal curvatures of Hippocampal fissure; a volume, a surface area, a maximum principal curvature, a minimum principal curvature, and a ratio of principal curvatures of Hippocampal tail; a maximum principal curvature, a minimum principal curvature, and a ratio of principal curvatures of presubiculum; and a maximum principal curvature, a minimum principal curvature, and a ratio of principal curvatures of subiculum.

2. An Alzheimer's disease prediction system using the parameters which have been trained and obtained from the neural network training system according to claim 1, wherein the Alzheimer's disease prediction system comprises:
an inference processor configured to obtain a third MMSE score and a fourth MMSE score, wherein the third MMSE score has a third time marker, and the fourth MMSE score has a fourth time marker; and
an inference neural network module comprising the parameters which have been trained;
wherein the inference processor is configured to:
obtain an orientation change data according to a third orientation score of the third MMSE score and a fourth orientation score of the fourth MMSE score;
obtain an MMSE change score according to the third MMSE score and the fourth MMSE score; and obtain an Alzheimer's disease prediction result according to the inference neural network module, the orientation change data, and the MMSE change data.

3. An Alzheimer's disease prediction system using the parameters which have been trained and obtained from the neural network training system according to claim 1, wherein the Alzheimer's disease prediction system comprises:

an inference processor configured to obtain a third brain MRI data, a fourth MRI data, a third MMSE score, and a fourth MMSE score, wherein the third MMSE score has a third time marker, the fourth MMSE score has a fourth time marker, the third brain MRI data corresponds to the third time marker, and the fourth brain MRI data corresponds to the fourth time marker; and an inference neural network module comprising the parameters which have been trained;

wherein the inference processor is configured to:

obtain an orientation change data according to a third orientation score of the third MMSE score and a fourth orientation score of the fourth MMSE score;

obtain an MMSE change score according to the third MMSE score and the fourth MMSE score;

obtain a plurality of image feature change data corresponding to the biomarkers according to the third brain MRI data and the fourth brain MRI data; and obtain an Alzheimer's disease prediction result according to the inference neural network module, the orientation change data, the MMSE change data, and the plurality of image feature change data.

4. A neural network training method performed by a processor, wherein the neural network training method comprises:

obtaining a plurality of historical data, wherein each of the plurality of historical data comprises a first Mini-Mental State Examination (MMSE) score, a second MMSE score, and an Alzheimer's marker, wherein the first MMSE score has a first time marker, and the second MMSE score has a second time marker;

obtaining a plurality of historical orientation change data according to a first orientation score of the first MMSE score and a second orientation score of the second MMSE score of each of the plurality of historical data;

obtaining a plurality of historical change data according to the first MMSE score and the second MMSE score of each of the plurality of historical data; and training a neural network module to obtain parameters which have been trained by using a training set comprising the plurality of historical orientation change data, the plurality of historical MMSE change data, and the Alzheimer's marker of each of the plurality of historical data;

wherein each of the plurality of historical data comprises a first brain magnetic resonance imaging (MRI) data and a second brain MRI data, the first brain MRI data corresponds to the first time marker, and the second brain MRI data corresponds to the second time marker; and wherein the neural network training method further comprises:

extracting a plurality of first corresponding data corresponding to the first time marker from the first brain MRI data of the plurality of historical data and extracting a plurality of second corresponding data corresponding to the second time marker from the second brain MRI data of the plurality of historical data for each of biomarkers among a plurality of the biomarkers; and obtaining a plurality of biomarker change data according to the plurality of first corresponding data and the plurality of second corresponding data of each of the biomarkers;

wherein the training set comprises the plurality of biomarker change data; wherein each of the biomarkers is selected from the group consisting of a volume, a surface area, a maximum principal curvature, a minimum principal curvature, and a ratio of principal curvatures of alveus; a volume, a surface, a maximum principal curvature, a minimum principal curvature, and a ratio of principal curvatures of parasubiculum; a volume, a surface area, a maximum principal curvature, a minimum principal curvature, and a ratio of principal curvatures of Cornu Ammonis 1 (CA1); a volume, a surface area, a maximum principal curvature, a minimum principal curvature, and a ratio of principal curvatures of Cornu Ammonis 2/3 (CA2/3); a volume, a surface area, a maximum principal curvature, a minimum principal curvature, and a ratio of principal curvatures of Cornu Ammonis 4 (CA4); a volume, a surface area, a maximum principal curvature, a minimum principal curvature, and a ratio of principal curvatures of GC-DG; a volume, a surface area, a maximum principal curvature, a minimum principal curvature, and a ratio of principal curvatures of HATA; a volume, a surface area, a maximum principal curvature, a minimum principal curvature, and a ratio of principal curvatures of Fimbria; a volume, a surface area, a maximum principal curvature, a minimum principal curvature, and a ratio of principal curvatures of Molecular layer; a volume, a surface area, a maximum principal curvature, a minimum principal curvature, and a ratio of principal curvatures of Hippocampal fissure; a volume, a surface area, a maximum principal curvature, a minimum principal curvature, and a ratio of principal curvatures of Hippocampal tail; a maximum principal curvature, a minimum principal curvature, and a ratio of principal curvatures of presubiculum; and a maximum principal curvature, a minimum principal curvature, and a ratio of principal curvatures of subiculum.

5. An Alzheimer's disease prediction method using the parameters which have been trained and obtained from the neural network training method according to claim 4, wherein the Alzheimer's disease prediction method is performed by an inference processor and comprises:

obtaining a third MMSE score and a fourth MMSE score, wherein the third MMSE score has a third time marker, and the fourth MMSE score has a fourth time marker;

obtaining an orientation change data according to a third orientation score of the third MMSE score and a fourth orientation score of the fourth MMSE score;

obtaining an MMSE change score according to the third MMSE score and the fourth MMSE score; and obtaining an Alzheimer's disease prediction result according to an inference neural network module, the orientation change data, and the MMSE change data, wherein the inference neural network module comprises the parameters which have been trained.

6. An Alzheimer's disease prediction method using the parameters which have been trained and obtained from the neural network training system according to claim 4, wherein the Alzheimer's disease prediction method is performed by an inference processor and comprises:

obtaining a third brain MRI data, a fourth MRI data, a third MMSE score, and a fourth MMSE score, wherein the third MMSE score has a third time marker, the fourth MMSE score has a fourth time marker, the third brain MRI data corresponds to the third time marker, and the fourth brain MRI data corresponds to the fourth time marker; and obtaining an orientation change data according to a third orientation score of the third MMSE score and a fourth orientation score of the fourth MMSE score;

obtaining an MMSE change score according to the third MMSE score and the fourth MMSE score;

obtaining a plurality of image feature change data corresponding to the biomarkers according to the third brain MRI data and the fourth brain MRI data; and obtaining an Alzheimer's disease prediction result according to an inference neural network module, the orientation change data, the MMSE change data, and the plurality of image feature change data, wherein the inference neural network module comprises the parameters which have been trained.

* * * * *